US010829796B2

(12) United States Patent
Bork

(10) Patent No.: US 10,829,796 B2
(45) Date of Patent: Nov. 10, 2020

(54) BACTERIA IDENTIFICATION AND ANTIMICROBIAL SUSCEPTIBILITY TEST

(71) Applicant: MASTAPLEX LIMITED, North Dunedin (NZ)

(72) Inventor: Olaf Bork, Dunedin (NZ)

(73) Assignee: MASTAPLEX LIMITED, North Dunedin (NZ)

( * ) Notice: Subject to any disclaimer, the term of this patent is extended or adjusted under 35 U.S.C. 154(b) by 24 days.

(21) Appl. No.: 15/553,817

(22) PCT Filed: Feb. 26, 2016

(86) PCT No.: PCT/NZ2016/050027
§ 371 (c)(1),
(2) Date: Aug. 25, 2017

(87) PCT Pub. No.: WO2016/137341
PCT Pub. Date: Sep. 1, 2016

(65) Prior Publication Data
US 2018/0245124 A1    Aug. 30, 2018

(30) Foreign Application Priority Data

Feb. 27, 2015    (AU) .............................. 2015900695

(51) Int. Cl.
G01N 33/04    (2006.01)
C12Q 1/14    (2006.01)
C12Q 1/18    (2006.01)
C12Q 1/04    (2006.01)

(52) U.S. Cl.
CPC .............. *C12Q 1/14* (2013.01); *C12Q 1/04* (2013.01); *C12Q 1/18* (2013.01); *G01N 33/04* (2013.01); *G01N 2800/365* (2013.01)

(58) Field of Classification Search
CPC combination set(s) only.
See application file for complete search history.

(56) References Cited

U.S. PATENT DOCUMENTS 5,464,755 A * 11/1995 Bochner .................. C12Q 1/04
435/34
7,262,021 B1    8/2007 Taintor

FOREIGN PATENT DOCUMENTS

| WO | WO-1994/026926 A1 | 11/1994 |
| WO | WO-1999/018439 A1 | 4/1999 |
| WO | WO-2007/032691 A1 | 3/2007 |
| WO | WO-2008/002156 A1 | 1/2008 |
| WO | WO-2011/139263 A1 | 11/2011 |

OTHER PUBLICATIONS

HIMEDIA Labs Technical Data Sheet M391, as available on the internet Feb. 11, 2014. Accessed via the Wayback Machine Internet Archive on Jun. 16, 2019.*
Murray, P. et al., Medical Microbiology Elsevier Saunders 2013 p. 23.*
MASTiK for Animal Use—Drugs.com internet archive, Jun. 24, 2012.*
Baird-Parker RPF Agar [retrieved from the internet on Oct. 21, 2015]<URL:http://www.solabia.com/solabia/produitsDiagnostic.nsf/0/16C2DB9AC,27A14E0C12574 DE004DDB3D/$file/TDS BT005 010%20 vl.pdf> published on Mar. 8, 2011.
Da Silva et al., Biochemical Characterisitics of Typical and Atypical *Staphylococcus aureus* in Mastitic Milk and Environmental Samples of Brazilian Dairy Farms, *Br. J. Microbiol.*, 31(2):103-6 (2000).
Detecting Bovine Mastitis Contamination in the Milk Chain [retrieved from the internet Oct. 21, 2015. Published 2010, Retrieved from the Internet <URL:http://www.himedialabs.com/HML/images/literature/pdf/100000027/5.pdf>.
International Preliminary Report on Patentability, PCT/NZ2016/050027, Australian Patent Office, dated Aug. 29, 2017.
International Search Report and Written Opinion of the International Search Authority, PCT/NZ2016/050027, dated May 4, 2016.
Mastik (Canada) for Animal Use—Drugs.com, Nac No. 12700031 (retrieved from the internet Oct. 21, 2015, dated Jun. 24, 2012.).
Mastic for Animal Use—Drugs.com, Nac No. 11200063 (retrieved from the internet Jun. 6, 2018, dated Jun. 24, 2012.).
Nam et al., Antimicrobial Susceptibility of Coagulase-Negative Staphylococci Isolated from Bovine Mastitis Between 2003 and 2008 in Korea, *J. Microbiol. Biotechnol.*, 20(10):1446-9. (2010).
Ollis et al., Detection of *Staphylococcus aureus* in bulk tank milk usingmodified Baird-Parker culture media, *Canadian Veterinary J.*, 10:619-23 (1995).
Parisi, Coagulase-negative staphylococci and the epidemiological typing of *Staphylococcus epidermidis*, *Microbiological Rev.*, 49(2):126-39 (1985).
Raemy et al., Phenotypic and genotypic identification of streptococci and related bacteria isolated from bovine intramammary infections, Acta. *Veterinaria Scandinavica*, 55(53):1-9 (2013).
Rapid Test Kit for Esculin Hydrolysis [retrieved from the internet Oct. 21, 2015] <URL: https://www.tody.ro/document/20470010-Esculin-Hidrolisis-Rapid-Test-Kit>.
Watts et al., Performance Standards for Antimicrobial Disk and Dilution Susceptibility Tests for Bacteria Isolated from Animals; Approved Standard. Third Edition, Clinical and Laboratory Standards Institute, 28(8) (2008).

(Continued)

*Primary Examiner* — Heidi Reese

(74) *Attorney, Agent, or Firm* — Marshall, Gerstein & Borun LLP

(57) ABSTRACT

The present invention provides compositions, methods and kits for bacteria identification and anti-microbial susceptibility testing for the treatment of, for example, acute and chronic infections including infectious disease. The present invention is particularly useful in the identification of bacteria causing mastitis, and to antibiotic susceptibility testing to facilitate in the identification of an appropriate treatment for mastitis.

11 Claims, 3 Drawing Sheets

(56) References Cited

OTHER PUBLICATIONS

Extended European Search Report dated Sep. 28, 2018 for European Patent No. 3262183 (Application No. 16755973.1).
Mastik (Canada) for Animal Use—Drugs.com (retrieved from the internet Jun. 6, 2018.).

* cited by examiner 16h culture 24h culture

BACTERIA IDENTIFICATION AND ANTIMICROBIAL SUSCEPTIBILITY TEST

TECHNICAL FIELD

The present invention relates to bacteria identification and anti-microbial susceptibility testing for the treatment of, for example, acute and chronic infections including infectious disease. The present invention is particularly useful in the identification of bacteria causing mastitis, and to antibiotic susceptibility testing to facilitate in the identification of an appropriate treatment for mastitis.

BACKGROUND OF THE INVENTION

There have been significant advances in the field of clinical microbiology and in the treatment and management of infectious diseases in recent decades. However, life threatening and debilitating systemic and localized microbial infections remain a major problem for both human and animal healthcare. Moreover, the emergence of multidrug resistance organisms has increased the challenges facing human and veterinarian healthcare practices.

Inadequately or improperly treated microbial infections are largely responsible for the rise of multidrug resistant strains of bacteria that cause many hospital and on-farm originating infections. Drug resistance, specifically antibiotic resistance, often occurs when the antibiotic used to treat an infection is either improperly selected, prescribed in a fashion that does not effectively eradicate the infectious agent, or as a result of poor patient compliance or farming practices. Furthermore, when ineffective or unnecessary antibiotics are prescribed any infecting bacteria present continues to multiply unabated often resulting in life threatening complications necessitating expensive, aggressive treatments including otherwise needless hospitalization. Therefore, the accurate and rapid diagnosis of a potential infectious agent is critical to improved patient care, reduced healthcare costs and the preservation of antimicrobial efficacy.

Infection of humans or animals may be caused by, among other pathogens, bacteria. Antimicrobial agents, including antibiotics, are employed in an attempt to either kill a bacterial population or inhibit its growth as a means to combat the infection. A short list of disease causing bacteria and the first and second choice of antimicrobials against common or important bacteria are listed in, for example, "Pharmacology", Rang & Dale 1987, Churchchill Livingstone. Typical antimicrobial agents used in human and veterinary medicine include antibiotics. For example benzylpenicillin (or penicillin G) is the drug of choice for infections caused by *streptococci*, pneumococci, menigococci, gonococci and non-penicillinase-producing *staphylococci*. In the case of beta-lactamase producing staphyolococci the use of cloxacillin among others is recommended. On the other hand, benzylpenicillin is often almost ineffective against gram negative bacteria such as coliform bacteria such as, for example, *Escherichia coli*. Broad spectrum antibiotics are often active against coliform bacteria. Typical broad spectrum antibiotics are ampicillin, amoxicillin or cephalosporins such as cefotaxime or ceftiofur.

Commonly used antibiotics can be classified as aminoglycosides, carbapenems and monobactams, cephalosporins, chloramphenicol, lincosamides, macrolides, pleuromutilins, glycopeptides, polypeptides, penicillins, polymixins, quinolones, sulfonamides and tetracyclines, among others.

Other type of antimicrobial agents include, for example, nisin, silver, or desinfectives among many others.

Interestingly, the majority of antimicrobials administered worldwide are not administerd to human patients, but rather to animals, including cattle, sheep, pig, chicken, and fish, for purposes of food production. Antibiotics are administered to these animals to treat disease in infected animals, among other reasons.

The use of large quantities of antimicrobials in food production and the unintended wide release of antimicrobials into the environment through animal and human sewage and runoff water from agricultural sites has public health consequences, most clearly seen in resistant zoonotic bacteria associated with foodborne disease in humans. Furthermore, of unknown qualitative and quantitative significance is the potential passage of resistance genes from bacteria of animal origin to human pathogens.

Prompt antimicrobial treatment of an infected patient can make the difference between successful therapy, long-term disability or even death. Unfortunately, the use and misuse of antimicrobials has driven the relentless expansion of resistant microbes leading to a loss of efficacy by traditional treatment regimes. Indeed, antibiotic resistance and the evolution multi-drug resistant bacteria or 'super bugs' has been identified by the World Health Organisation as a significant threat to the long term survival of the human population.

Antimicrobial treatments typically commence soon after detection of infection or disease. Treatment selection is usually based on first or second choice of antimicrobial recommendation from specialised institutions for a specific bacterial infection in humans and animals (e.g. ear, throat, udder or uterus etc).

It would be advantageous if identification of infection or infectious disease causing bacteria occurs prior to treatment so that an appropriate antimicrobial for treatment may be selected for administration. However, knowing the type of bacteria is not always sufficient to select an appropriate antimicrobial treatment. For example in the case of Staphylococci, benzylpenicillin is the first choice of drug if it is a non-penicillinase producing Staphylococci. However, this type of information is not usually known prior to treatment or necessarily after selective and/or differential bacterial enrichment testing has occurred.

Ideally, it would be desirable to perform antimicrobial susceptibility testing prior to treatment which not only supports the selection of an antimicrobial treatment regime, but also supports the selection of an appropriate dose. There are, however, several limitations with this approach since testing must be performed in established laboratories with >days turnaround time. In the meantime, the infection remains untreated or it has been treated with (e.g.) a broad spectrum antimicrobial agent in an attempt to combat the infection. Not surprisingly, this practice that has led to the overuse of antibiotics and consequently the development of drug resistance (e.g. antibiotic resistance) in many bacterial species.

Mastitis

Mastitis is an inflammatory disease of the mammalian mammary gland. In veterinary medicine the most important and the most frequently encountered mastitis is that of bovine animals, and in particular dairy cows.

Dairy herds are typically bred for milk production. The convention of milking up to two to three times during a 24 hour period predisposes the mammary glands of cows to infection. In addition, the involvement of mechanical apparatus in automated milking practices, which apparatus passes from cow to cow, means infection can easily be transmitted from one animal to another.

The mammary gland has a number of natural defense mechanisms against bacterial pathogens. However, these defense mechanisms can be overcome by high levels of bacterial challenge, through poor animal husbandry or through physiological changes at certain times in the lactation cycle. For example, the period around drying off and calving is associated with a relatively high incidence of mastitis.

Mastitis can be caused by many different species of gram positive and negative bacteria. Those bacterial species most commonly implicated in bovine mastitis fall into two categories. The first category includes host pathogens such as *Staphylococcus aureus* and *Streptococcus agalactiae*. These bacteria live on the skin of the udder or in the udder per se and are a source of infection to other cows in the herd. The second category includes environmental pathogens such as *Streptococcus uberis* and *Escherichia coll*. These pathogens are found in the immediate environment of the dairy cow and therefore present a constant risk to infection.

Mastitis caused by the bacteria characterized above can manifest as either clinical or subclinical disease.

Clinical mastitis is an inflammatory response to infection causing visibly abnormal milk (e.g. color, fibrin clots). As the extent of the inflammation increases, changes in the udder (swelling, heat, pain, redness) may also become apparent. Clinical cases that include only local signs are referred to as mild or moderate. If the inflammatory response includes systemic involvement (fever, anorexia, shock), the case is termed severe. If the onset is very rapid, as often occurs with severe clinical cases, it is termed an acute case of severe mastitis. More severely affected cows tend to have more serous secretions in the affected quarter. That said, milder presentations of clinical mastitis are most typical.

Subclinical mastitis is the presence of an infection without apparent signs of local inflammation or systemic involvement. Although transient episodes of abnormal milk or udder inflammation may appear, these infections are for the most part asymptomatic and, if the infection persists for at least 2 months, are termed chronic. Once established, many of these infections persist for entire lactations or the life of the cow. Detection is best done by examination of milk for somatic cell counts (SCCs) (predominantly neutrophils).

Mastitis continues to be a major cause of economic loss in the dairy industry despite the availability of various treatment options. Currently, the primary method of treating mastitis in cows (inflammation of the udder) as well as treating metritis (inflammation of the uterus) is antibiotic therapy.

A recommendation as to first and second choice antimicrobial agents is often given by governmental bodies or specialised disease institutions. Bovine mastitis can be caused by gram positive and negative bacteria. The most common and important bacteria are *Strep uberis*, *Staph aureus*, coagulase negative *Staph*, *Strep agalactiae*, *Strep dysagalactiae* and *E-Coli*. Mastitis milk changes the consistency compared to milk from healthy cows. Mastitis milk can have clots and the texture can be watery and thin or thick. The colour of mastitis milk can be described as between yellow to brownish.

In addition, usually mastitis milk will have a high somatic cell count which can be up to several millions per millilitre which is different to health cow's milk.

There are a number of bacteria test kits for bovine mastitis on the market and can be used to identify the type of bacteria causing infection on farm. For example 'The Overnighter' (WO 2007/032691) describes a microbiological growth device and receptacle. The growth media is based on agar media (gel type) and bacteria identification is shown by colorimetric change. Bacteria identification occurs within 24 to 48 h.

WO 1999/18439 and WO 2011/139263 describe rapid film based aerobic and *E. coli*/coliform count tests. The rapid aerobic count film detects all aerobic bacteria found in a milk sample, while the *E. coli*/coliform film will only support growth of Gram-negative bacteria. Once it has been determined whether the mastitis infection is caused by Gram-positive or Gram-negative bacteria, a treatment decision could be made to resolve the infection."

CHECK-UP Mastitis Diagnostic Tool, On Farm Mastitis Testing, Farm Medix, www.farmmedix.com/ is an agar plate comprising four zones to identify *Streptococcus uberis*, *Staphylococcus aureus*, Staphylococci SPP and *E. Coli*. The detection time is 15 to 24 h.

However, none of these tests offer antimicrobial susceptibility testing.

Bovine mastitis is only one typical example of infection. Mastitis can also occur in humans or other milk producing animals. Metritis is another typical infection among many other bacterial infection. The treatment of these bacterial infection suffer often from not knowing the type of bacteria or the antimicrobial susceptibility which can lead to the selection of inappropriate antimicrobial to treat the infection which as a consequence leads to another antimicrobial treatment.

Applicant has now developed novel approaches to bacteria identification, particularly with respect to bacteria known to cause infections such as mastitis and metritis. Further, Applicant has surprisingly developed new approaches to colorimetric based antimicrobial susceptibility testing which can be performed directly on biological samples obtained from human and non-human animals. This approach provides 'real time' information with respect to the susceptibility of (e.g.) bacteria to antimicrobial agents for the purpose of informing treatment options. These features and other advantages will become apparent from the description which follows.

SUMMARY OF THE INVENTION

The inventions described and claimed herein have many attributes and embodiments including, but not limited to, those set forth or described or referenced in this Summary of the Invention. It is not intended to be all inclusive and the inventions described and claimed herein are not limited to or by the features or embodiments identified in this Summary of the Invention, which is included for purposes of illustration only and not restriction.

In one aspect of the present invention there is provided a method for performing an antimicrobial susceptibility test on a biological sample obtained from a human or non-human animal, wherein the human or non-human animal may be infected by, or at risk of infection by, one or more infection causing bacteria, the method comprising,
  (i) providing a reaction mix comprising a biological sample obtained from a human or non-human animal and susceptibility media comprising media for growth, an antimicrobial agent, a colour based pH indicator and a stabilizing agent; and
  (ii) determining the susceptibility of the one or more bacteria in the sample to the antimicrobial agent by observing a colour change when the sample is added to the susceptibility media, wherein, the pH indicator is present in the reaction mix in an amount sufficient to inhibit growth of the one or more infection causing bacteria if not for the presence of the stabilizing agent.

In another aspect of the present invention there is provided a method for performing antimicrobial susceptibility test on a biological sample comprising milk obtained from a human or non-human animal, wherein the human or non-human animal may be infected by, or at risk of infection by, one or more infection causing bacteria, the method comprising,
  (i) providing a reaction mix comprising a biological sample obtained from a human or non-human animal and susceptibility media comprising an antimicrobial agent and a colour based pH indicator; and
  (ii) determining the susceptibility of the one or more bacteria in the sample to the antimicrobial agent by observing a colour change when the sample is added to the susceptibility media,
wherein, the pH indicator is present in the reaction mix in an amount sufficient to inhibit growth of the one or more infection causing bacteria if not for the presence of the stabilizing agent In yet another aspect of the present invention there is provided a method for identifying Group D Streptococci in a human or non-human animal, wherein the human or non-human animal may be infected by, or at risk to infection by, Group D Streptococci, the method comprising:
  (i) providing a reaction mix comprising a biological sample obtained from a human or non-human animal and identification media comprising esculin, ferric citrate and a stabilizing agent; and
  (ii) identifying if Group D Streptococci are present in the sample,
wherein, the esculin and ferric citrate is present in the reaction mix in an amount sufficient to inhibit growth of the Group D Streptococci if not for the presence of the stabilizing agent
and wherein, identification of Group D Streptococci in the sample is confirmed by blackening of the reaction mix,
where identification of Group D Streptococci in the sample indicates that the human or non-human animal is infected by, or at risk to infection by, the Group D Streptococci.

In another aspect of the present invention there is provided a method for identifying Group D Streptococci in a human or non-human animal, wherein the human or non-human animal may be infected by, or at risk to infection by, Group D *Streptococci*, the method comprising:
  (i) providing a reaction mix comprising a milk containing biological sample obtained from a human or non-human animal and identification media comprising esculin and ferric citrate; and
  (ii) identifying if Group D *Streptococci* are present in the sample,
wherein, the esculin and ferric citrate is present in the reaction mix in an amount sufficient to inhibit growth of the Group D *Streptococci* if not for the presence of the stabilizing agent in the milk sample,
and wherein, identification of Group D *Streptococci* in the sample is confirmed by blackening of the reaction mix,
where identification of Group D *Streptococci* in the sample indicates that the human or non-human animal is infected by, or at risk to infection by, the Group D *Streptococci*.

In a further aspect of the present invention there is provided a method for identifying coagulase positive *Staphylococci* in a human or non-human animal, wherein the human or non-human animal may be infected by, or at risk to infection by, coagulase positive *Staphylococci*, the method comprising:
  (i) providing a reaction mix comprising a biological sample obtained from a human or non-human animal and identification media comprising tellurite and a stabilizing agent; and
  (ii) identifying if coagulase positive *Staphylococci* is present in the sample,
wherein, the tellurite is present in the reaction mix in an amount sufficient to inhibit growth of the coagulase positive Staphylococci if not for the presence of the stabilizing agent
and wherein, identification of coagulase positive Staphylococci in the sample is confirmed by the appearance of a black sediment in the reaction mix,
where identification of coagulase positive Staphylococci in the sample indicates that the human or non-human animal is infected by, or at risk to infection by, coagulase positive Staphylococci.

In yet a further aspect of the present invention there is provided a method for identifying coagulase negative Staphylococci in a human or a non-human animal, wherein the human or non-human animal is infected by, or is at risk of infection by, coagulase negative Staphylococci, the method comprising;
  (i) establishing that coagulase positive Staphylococci is not present in the sample according to the methods described herein;
  (ii) providing a reaction mix comprising a biological sample obtained from the same human or non-human animal with an identification media comprising high salt concentration, a carbohydrate source and a colour based pH indicator; and
  (iii) identifying if coagulase negative Staphylococci are present in the sample,
wherein, the pH indicator in the reaction mix is present in an amount sufficient to inhibit growth of the coagulase negative Staphylococci if not for the presence of the stabilizing agent,
and wherein, the carbohydrate source in the second reaction mix is selected from one or more of the group consisting of glucose fructose, maltose, sucrose, glycerol, galactose, mannose and lactose,
and wherein, identification of coagulase negative Staphylococci is confirmed by a colour change in the reaction mix caused by a change in pH,
where identification of coagulase negative Staphylococci in the sample indicates that the human or non-human animal is infected by, or at risk to infection by, coagulase negative Staphylococci.

In yet another aspect of the present invention there is provided a method of identifying one or more bacteria causing mastitis in a human or non-human animal, the method comprising:
  (i) providing a reaction mix comprising a milk sample obtained from a human or non-human animal and identification media; and
  (ii) identifying if one or more bacteria causing mastitis are present in the milk sample according to any of the methods described herein, the modification being that the reaction mix does not require a stabilizing agent.

In yet a further aspect of the present invention there is provided a test kit for:
  (i) identifying one or more infection causing bacteria in a human or non-human animal, and/or (ii) for performing antimicrobial susceptibility testing on bacteria causing infection in a human or a non-human animal, the test kit comprising reagents for performing bacteria identification and/or antimicrobial susceptibility testing on a test sample from the human or non-human animal according to any method described herein, together with instructions for use.

GENERAL DEFINITIONS

Figure 1:
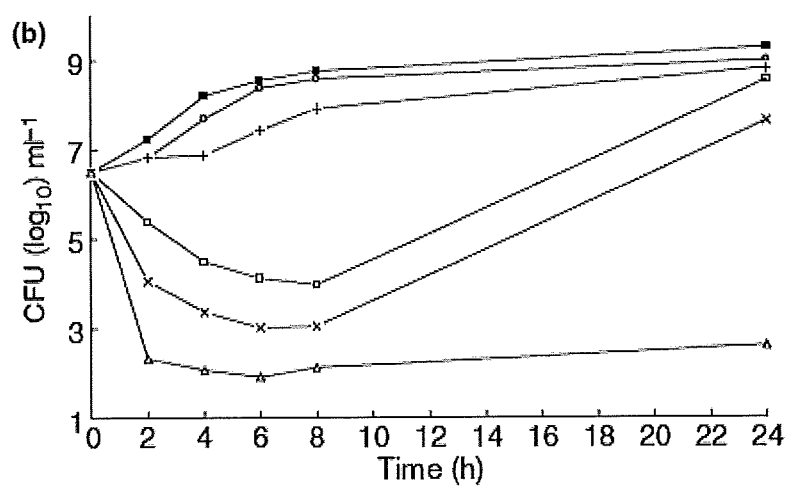
FIG. 1 shows inhibition of growth of *Staphylococcus aureus* exposed to varying levels of kanamycin as a function of time. Control (closed square), 0.5 ug/mL kanamycin (circle), 1.0 ug/mL kanamycin (plus symbol), 2.0 ug/mL kanamycin (open square), 4.0 ug/mL kanamycin (cross) and 8 ug/mL kanamycin (triangle).

Unless specifically defined otherwise, all technical and scientific terms used herein shall be taken to have the same meaning as commonly understood by one of ordinary skill in the art (for example, in microbiology, immunology, immunohistochemistry, protein chemistry, and biochemistry).

It is intended that reference to a range of numbers disclosed herein (e.g. 1 to 10) also incorporates reference to all related numbers within that range (e.g. 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Selected Definitions

The term "microorganism" will be used herein to describe any eukaryotic or prokaryotic microorganism including, for example, bacteria, yeast, fungi, virus and the like.

The term "infection" will be used herein to describe invasion by and multiplication of pathogenic microorganisms in a bodily part or tissue, which may produce subsequent tissue injury and progress to overt disease through a variety of cellular or toxic mechanisms.

The term "*Streptococci*" will be used herein to mean one *Streptococcus* or a population of *Streptococci*.

The term "Group D *Streptococci*" will be used herein to mean one Group D *Streptococcus* or a population of Group D *Streptococci*. Examples of Group D *Streptococci* include, but are not limited to, *Streptococcus uberis*, *Streptococcus bovis* and *Streptococcus equinis*.

The term "coagulase negative Staphylococci" or "coagulase negative *Staphylococcus*" will be used herein to describe those Staphylococci which do not have the protein enzyme coagulase which enables the conversion of fibrinogen to fibrin. Examples of coagulase negative Staphylococci include, but are not limited to, *Staphylococcus chromogenes, Staphylococcus simulans, Staphylococcus xylosus, Staphylococcus epidermidis, Staphylococcus hyicus, Staphylococcus hemolyticus, Staphylococcus arlettae, Staphylococcus aureusd, Staphylococcus gallinarum, Staphylococcus lentus, Staphylococcus pseudintermedius, Staphylococcus saprophyticus, Staphylococcus warneri/pasteuri, Staphylococcus aureus* (some strains are coagulase negative).

The term "coagulase positive Staphylococci" or "coagulase positive *Staphylococcus*" will be used herein to describe those Staphylococci which do have the protein enzyme coagulase which enables the conversion of fibrinogen to fibrin. Examples of coagulase positive Staphylococci include, but are not limited to, *Staphylococcus aureus, Staphylococcus delphini, Staphylococcus hyicus, Staphylococcus intermedius, Staphylococcus lutrae, Staphylococcus pseudintermedius* and *Staphylococcus schleiferi* subsp.

The term "coliform bacteria" will be used herein to describe rod shaped, gram negative bacteria which ferment lactose with the production of acid and gas.

The term "indicator" or "indicator composition" will be used herein to describe specific compounds or molecules which include, but are not limited to, one or more of phenol red, bromocresol purple, bromothymol blue, bromocresol green, methyl red, methyl purple, azolitmin, neutral red, naphtholphthalein, cresol red, cresolphthalein, phenolphthalein, 2,4-dimitrophenol, erythrosine disodium salt, benzopurpurine 4B, N,N-dimtehyl-p-(m-tolylazo)amiline, p-Dimethylaminoazobenzene, 4,4'-Bis(2-amino-1-naphthylazo)-2,2'-stilbenedisulfonic acid, tetrabromophenolphthalein ethyl ester potassium salt, bromphenol blue, congo red, methyl orange, ethyl orange, 4-(4-dimethylamino-1-naphylazo)-3-methoxybenzenesulfonic acid, resazurin, 4-phneylazo-1-naphthylanine, ethyl red 2-(p-dimethylaminophenylazo) pyridine, 4-(p-ethoxyphenylazo)-m-phenylene-diamine monohydrochloride, resorcin blue, alizarin red S, propyl red, chlorophenol red, p-nitrophenol, alizarin 2-(2,4-dinitrophenylazo) 1-naphtol-3,6-disulfonic acid disodium salt, 6,8-dinitro-2,4-(1H) quinazolinedione, brilliant yellow, m-nitrophenol, turmeric (curcumin), metracresol purple, 4,4'-Bis(4-amino-1-naphthylazo)-2,2'-stilbenedisulfonic acid, thymol blue, p-naphtholbenzein, phenolphthalein, o-cresolphthalein, ethyl bis(2,4-dimethylphenyl) ethanoate. For avoidance of doubt, the term indicator includes pH indicators.

The term "subject" will be used herein to describe human and non-human mammals. Examples of non-human animals include, but are not limited to, cows, sheep, deer, horses, pigs, chickens, fish, dogs, cats, mice, rats, primates (including gorillas, rhesus monkeys and chimpanzees), possums and other domestic farm or zoo animals. Thus, the assays, methods and kits described herein have application to both human and non-human animals, in particular, and without limitation, humans, primates, farm animals including cattle, sheep, goats, pigs, deer, alpacas, llamas, buffalo, companion and/or pure bred animals including cats, dogs and horses. Further, while a subject is preferably a living organism, the invention described herein may be used in post-mortem analysis as well.

The term "sample" or "biological sample" will be used herein to mean any sample taken or derived from a subject. Such a sample may be obtained from a subject, or may be obtained from biological materials intended to be provided to the subject. For example, a sample may be obtained from blood or milk being assessed which may be derived from a human or non-human animal. Included are samples taken or derived from any subjects such as from normal healthy subjects and/or healthy subjects for whom it is useful to understand the level of infectious microorganism(s). Preferred samples are body fluid samples. The term "body fluid sample" as used herein refers to a sample of bodily fluid obtained for the purpose of, for example, diagnosis, prognosis, classification or evaluation of a subject of interest. In certain embodiments, such a sample may be obtained for the purpose of determining the severity of infection. The sample may be any sample known in the art in which one or more microorganisms may be detected. Included are any body fluids such as a whole blood sample, plasma, serum, milk, ovarian follicular fluid sample, seminal fluid sample, cerebrospinal fluid, fluid sample from the uterus, saliva, sputum, urine, pleural effusions, interstitial fluid, synovial fluid, lymph, tears, for example, although whole blood sample, plasma, serum, and milk are particularly suited for use in this invention. In addition, one of skill in the art would realise that certain body fluid samples would be more readily analysed following a fractionation or purification procedure, for example, separation of whole blood into serum or plasma components.

The term "test strip" will be used herein to mean any configuration of test plates, wells, vials or receptacles in which the assays and methods of the present invention may be performed. For example, bacteria identification and/or antimicrobial susceptibility testing run simultaneously, separately or sequentially, as described herein.

The term "qualitative susceptibility" testing will be used herein to describe apparatus and methods which produce test results that generally indicate whether a microorganism or cellular specimen is sensitive or resistant to a particular antimicrobial product. Depending on the method involved only one or two concentrations of antimicrobial product are usually utilized. The degree of sensitivity or resistance is not reported in qualitative susceptibility testing.

The term "quantitative susceptibility testing" will be used herein to describe testing apparatus and methods which produce test results that provide data on the concentration of the antimicrobial product that will be sufficient to inhibit growth of the microorganism. Typically, for microorganism specimens, multiple different dilutions of the antimicrobial product are utilized covering the therapeutic range of concentrations of the antimicrobial product. The term Minimum Inhibitory Concentration (MIC) is often used to refer to the result provided by quantitative susceptibility testing of microorganism and is defined as the minimum concentration of the antimicrobial product which will produce inhibition of the growth of the microorganism.

The term "antimicrobial agent" will be used herein to describe an agent which kills or inhibits the growth of a microorganism, including for example bacteria, yeast, fungi, viruses, parasites, etc. An antimicrobial agent which inhibits growth of a microorganism or population of microorganism is said to be microbiostatic (e.g. bacteriostatic in the case of an antibacterial agent which inhibits the growth of bacteria). Similarly, an antimicrobial agent which kills a microorganism or population of microorganism is said to be microbiocidal (e.g. bacteriocidal in the case of an antibacterial agent which kills bacteria). Examples of suitable antimicrobial agents are listed below.

As used herein, the terms "treating" and "treatment" refer to both therapeutic treatment and prophylactic or preventative measures.

DETAILED DESCRIPTION

The present invention is concerned with the identification of bacteria known to cause infection or infectious disease in human and non-human animals. The present invention is also concerned with antibiotic susceptibility testing to determine to which antibiotic(s) infection causing bacteria and specific strains thereof are susceptible.

1. Bacteria Identification

It would be advantageous if identification of infection or infectious disease causing bacteria guides treatment decisions so that an appropriate antimicrobial may be selected for therapy. That is, identification of infection or infectious disease causing bacteria in a biological sample obtained from a human or non-human animal may be used to inform treatment options for follow-on therapies. Identification of infection or infectious disease causing bacteria may also be used to map the prevalence of bacteria associated with infectious disease outbreaks and/or within defined geographical parameters. Further, information concerning identification of infection or infectious disease causing bacteria associated with certain disease states such as, for example, mastitis and metritis, may be used to build a database of information useful for monitoring historical and seasonal changes and geographical outbreaks associated with certain infectious diseases.

Applicant has discovered novel approaches to identification of bacteria in biological samples including, but not limited to, identification of *Streptococci* and Staphylococci.

Surprisingly, Applicant has discovered that *Streptococci*, and in particular Group D *Streptococci* comprising (e.g.) *Streptococcus uberis*, may be identified in a biological sample obtained from a human or non-human animal by enriching in identification media comprising esculin, ferric citrate and a stabilizing agent. Group D *Streptococci*, including *Streptococcus uberis* for example, hydrolyse esculin to esculetin and dextrose. Esculetin reacts with ferric citrate producing a blackening of the culture media, thereby providing a detectable change unique to Group D *Streptococci*. The presence of a stabilizing agent such as (e.g.) milk, is used to suppress the inhibitory activity of esculin and ferric citrate on bacteria growth (refer to (e.g.) Tables 2a-2e in Example 2, where the inhibitory effect of these analytes is demonstrated using standard enrichment media). This means that increased concentrations of esculin and ferric citrate may be used in the methods according to the present invention to enhance the identification of Group D *Streptococci*. This is particularly important for use on clinical samples where there is background colour associated with infection causing microorganisms. This point is discussed in further detail below.

For clarity, the term "enriching" is intended to mean any art known technique that increases the number of bacteria in the sample for the purpose of detection and identification. This includes not only enrichment, but also culturing as well as positive or negative growth selection techniques.

Accordingly, one aspect of the present invention there is provided a method for identifying Group D *Streptococci* in a human or non-human animal, wherein the human or non-human animal may be infected by, or at risk to infection by, Group D *Streptococci*, the method comprising:
(i) providing a reaction mix comprising a biological sample obtained from a human or non-human animal and identification media comprising esculin, ferric citrate and a stabilizing agent; and
(ii) identifying if Group D *Streptococci* are present in the sample, wherein, the esculin and ferric citrate is present in the reaction mix in an amount sufficient to inhibit growth of the Group D *Streptococci* if not for the presence of the stabilizing agent and wherein, identification of Group D *Streptococci* in the sample is confirmed by blackening of the reaction mix, where identification of Group D *Streptococci* in the sample indicates that the human or non-human animal is infected by, or at risk to infection by, the Group D *Streptococci*.

In one example, the stabilizing agent comprises a milk derived protein or milk derived protein extract. Examples of milk derived proteins or milk derived protein extracts include, but are not limited to, α-casein, β-casein (including one or more of A1, A2, A3, B, C, D, E and F variants), casein sodium (e.g. comprising α-casein, β-casein and κ-casein), κ-casein, β-lactoglobulin, whey protein, lactalbumin, lactoferrin and milk or milk powder, as well as combinations thereof.

The milk proteins and extracts may be derived from any genetic source including, but not limited to, those described at:

ansci.illinois.edu/static/ansc438/Milkcompsynth/milk-comp_table.html

Casein sodium may be obtained from Sigma Chemicals (Cat # C8654).

In one example, the Group D *Streptococci* are selected from the group consisting of *Streptococcus uberis, Streptococcus bovine* and *Streptococcus equinis*.

In yet another example according to the first aspect of the present invention, the identification media further comprises components selected from one or more of the group consisting of enrichment, growth and selection media. The terms "enrichment", "growth" and "selection" would be well known to a person skilled in the relevant art. Further, examples of suitable enrichment, growth and selection media for use in the methods of the present invention would also be known to a person skilled in the relevant art. Further, non-limiting examples of enrichment, growth and selection media are described in the Examples which follow.

In another example according to the first aspect of the present invention, the step of combining the sample with the identification media further comprises enriching the bacteria for a period of time sufficient to identify if one or more bacteria is present in the sample.

In yet another example, the step of enriching the bacteria comprises culturing at between 25° C. and 45° C. for between 6 and 48 h. For the avoidance of doubt and by way of illustration, culturing at between 25 and 45° C. includes culturing at 25, 26, 27, 28, 29, 30, 31, 32, 33, 34, 35, 36, 37, 38, 39, 40, 41, 42, 43, 44 or 45° C. Similarly, for the avoidance of doubt and by way of illustration only, culturing for between 6 and 48 h includes culturing for 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 h.

The identification media may comprise any enrichment, growth and/or selection media sufficient to enrich for bacteria present in the sample for the purpose of identification. At minimum, the identification media must support growth and selection of bacteria for the purpose of identifying bacteria of interest. Examples of enrichment media sufficient to support growth of bacteria growth are recited in Example 1. However, by way of illustration, non-limiting examples include Tryptic Soy Broth, Mueller Hinton Broth, MacConkey Broth, Mannitol Salt Broth, Esculin Azide Broth, Giolitti Cantoni Broth, depending on the bacteria to be enriched. The skilled person will understand that the present invention is not limited to liquid enrichment media and associated culturing techniques, and if necessary or desirable, other culturing media and techniques may be used. For example, culturing samples on agar gel comprising the desired enrichment, growth and/or selection media.

In one example according to the first aspect of the present invention, the identification media for identifying Group D *Streptococci* comprises Tryptic Soy Broth.

In addition to the identification media supporting bacteria growth, the identification media further comprises at least one selection media to facilitate identification of the bacteria of interest. For selection of Group D *Streptococci*, the selection media comprises esculin, ferric citrate and a stabilizing agent. The esculin and ferric citrate is present in the selection media in amounts that would normally inhibit the growth of bacteria, if not for the presence of the stabilizing agent which supports growth.

Esculin combined with ferric citrate is used as a selective medium for identification of *Streptococcus* group D. Esculin and ferric citrate are typically used in low concentration since increased compound concentrations could inhibit the growth of bacteria within the sample. Refer to Example 1 and Table 5, Example 3. Typically, up to 100 uL of samples in mixed with 10 mL of esculin broth or spread on an esculin agar. This is a volume ratio of about 1:100. This or similar volume ratios have the advantage to make the positive reaction (blackening of the culture media) visible and are feasible in a specialized laboratory. To provide a lay person a feasible method volume ratios between 1:10 and 10:1 are more applicable. Example 3, Table 6 shows that typical used esculin concentration 0.1% and ferric citrate concentration of 0.05% lead to weak colorimetric detection of *Streptococcus uberis* in milk. The problem is associated with the background colour of the clinical sample. The Applicant surprisingly found that higher concentrations of esculin and ferric citrate will not inhibit growth of Group D *Streptococci* in presence of a stabilizing agent (e.g.) milk derived protein or milk derived protein extract, and the presence of Group D *Streptococci* in the test sample may be conveniently identified by the naked eye (positive reaction=formation of a blackening of the culture media).

Accordingly, in one example according to the first aspect of the present invention, the identification media further comprises at between 0.1% and 2.0% esculin, and in particular 0.50% esculin. Between 0.1 and 2.0% esculin includes, but is not limited to, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 and 2.0% esculin, and comprises any and all values there between, including (e.g.) 0.25% esculin.

In a related example, the identification media comprises at between 0.05% and 1.0% ferric citrate, and in particular 0.25% ferric citrate. Between 0.05 and 1.0% ferric citrate includes, but is not limited to, 0.05, 0.1, 0.2, 0.3, 0.4, 0.5, 0.6, 0.7, 0.8, 0.9 and 1.0% ferric citrate, and comprises any and all values there between, including (e.g.) 0.125% ferric citrate. It would be known to the skilled person that ferric citrate may exist in various forms, including, but not limited to, ammonium ferric citrate as well as other free or salt forms.

In a further related example, the identification media comprises 0.50% esculin and 0.25% ferric citrate, and the step of combining the biological sample with the identification media comprises culturing the bacteria for a period of 16 to 24 h at 37° C.

According to this aspect of the present invention, the biological sample may be selected from the group consisting of milk, fluid sample from the uterus, whole blood sample, plasma, serum, ovarian follicular fluid sample, seminal fluid sample, cerebrospinal fluid, saliva, sputum, urine, pleural effusions, interstitial fluid, synovial fluid, lymph and tears.

Further, where the biological sample is milk (e.g. from a human or non-human animal such as a bovine animal) there is no requirement for a stabilizing agent in the reaction mix.

Accordingly, in another aspect of the present invention there is provided a method for identifying Group D *Streptococci* in a human or non-human animal, wherein the human or non-human animal may be infected by, or at risk to infection by, Group D *Streptococci*, the method comprising:
(i) providing a reaction mix comprising a milk containing biological sample obtained from a human or non-human animal and identification media comprising esculin and ferric citrate; and
(ii) identifying if Group D *Streptococci* are present in the sample,
wherein, the esculin and ferric citrate is present in the reaction mix in an amount sufficient to inhibit growth of the Group D *Streptococci* if not for the presence of the stabilizing agent in the milk sample,
and wherein, identification of Group D *Streptococci* in the sample is confirmed by blackening of the reaction mix,
where identification of Group D *Streptococci* in the sample indicates that the human or non-human animal is infected by, or at risk to infection by, the Group D *Streptococci*.

Since *Streptococci* are gram-positive bacteria, the identification media may further comprise one or more gram-negative antimicrobial agents, for example an antibiotic against gram-negative bacteria. Importantly, the presence of an antimicrobial agent against gram-negative bacteria will not affect enrichment of gram positive *Streptococci*. The inclusion of an antimicrobial against gram-negative bacteria will facilitate enrichment of Group D *Streptococci* for the purpose of identification.

Accordingly, in yet another related example, the identification media for identification of Group D *Streptococci* further comprises an antimicrobial agent against gram-negative bacteria.

Examples of gram negative antibiotics comprise monobactams which includes, but is not limited to, Aztreonam.

The specific identification of, and/or differentiation between, coagulase positive and coagulase negative Staphylococci is often desired. Knowing the type of Staphylococci causing infection can influence treatment decisions.

Surprisingly, Applicant has also discovered a novel approach to identify and differentiate between coagulase positive and coagulase negative Staphylococci.

Firstly, coagulase positive Staphylococci (e.g. *Staphylococcus aureus*) may be identified in a biological sample obtained from a human or non-human animal by enriching in identification media comprising tellurite. Applicant has surprisingly discovered that tellurite will selectively inhibit growth of coagulase negative bacteria.

Figure 2:
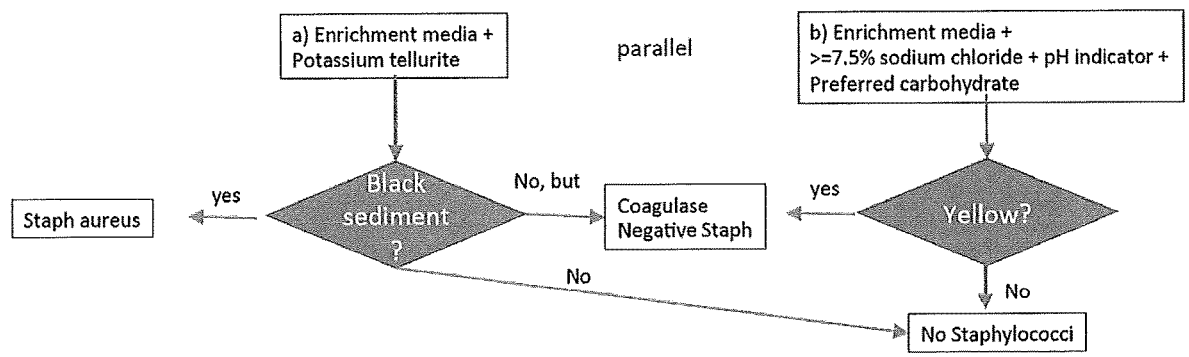
FIG. 2 shows bacteria identification/differentiation between *Staphylococcus aureus* and coagulase negative Staphylococci according to the methods of the present invention.
Figure 3:
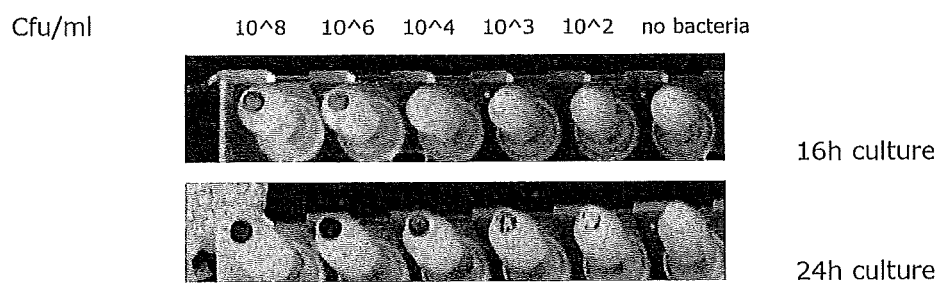
FIG. 3 shows visual identification of *Staphylococcus aureus* via appearance of black sediment according to methods of the present invention.

Secondly, if no enrichment for coagulase positive Staphylococci is detected then parallel identification of coagulase negative bacteria from the same biological sample may be achieved by enriching in identification media comprising high levels of salt (e.g. sodium chloride), a selective carbohydrate source and a pH indicator. The high salt concentration will only support growth of coagulase positive and coagulase negative Staphylococci. The absence of a black sediment in the tellurite enrichment media and growth of bacteria in identification media comprising high salt combined with a desired carbohydrate source allows indirect identification of coagulase negative Staphylococci, interrogated through a change in the pH. That is, in the presence of a desired carbohydrate source, coagulase negative bacteria will convert carbohydrate to acidification products resulting in a pH change that can be measured. This is shown in FIG. 2.

Accordingly, in a further aspect of the present invention there is provided a method for identifying coagulase positive Staphylococci in a human or non-human animal, wherein the human or non-human animal may be infected by, or at risk to infection by, coagulase positive Staphylococci, the method comprising:
(i) providing a reaction mix comprising a biological sample obtained from a human or non-human animal and identification media comprising tellurite and a stabilizing agent; and
(ii) identifying if coagulase positive Staphylococci is present in the sample,
wherein, the tellurite is present in the reaction mix in an amount sufficient to inhibit growth of the coagulase positive Staphylococci if not for the presence of the stabilizing agent
and wherein, identification of coagulase positive Staphylococci in the sample is confirmed by the appearance of a black sediment in the reaction mix,
where identification of coagulase positive Staphylococci in the sample indicates that the human or non-human animal is infected by, or at risk to infection by, coagulase positive Staphylococci.

In an example according to this aspect of the present invention, the coagulase positive Staphylococci is *Staphylococcus aureus*.

In another example according to the this aspect of the present invention, the identification media comprises between 0.5% and 30% of a 1% tellurite solution, and in particular between 10% and 22% of a 1% tellurite solution. In a related example, the tellurite is potassium tellurite.

In a related example, the identification media comprises 10% of a 1% potassium tellurite solution and the step of providing a reaction mix comprising the biological sample and identification media comprises culturing the bacteria for a period of between 7 and 48 h at 25 to 45° C.

In the event that the method according to this aspect of the present invention fails to identify coagulase positive Staphylococci in a biological sample obtained from the human or non-human animal, the sample may be further interrogated to indirectly determine for the presence of coagulase negative Staphylococci.

Accordingly, in yet a further aspect of the present invention there is provided a method for identifying coagulase negative Staphylococci in a human or a non-human animal, wherein the human or non-human animal is infected by, or is at risk of infection by, coagulase negative Staphylococci, the method comprising;
  (i) establishing that coagulase positive Staphylococci is not present in the sample according to the methods described herein;
  (ii) providing a reaction mix comprising a biological sample obtained from the same human or non-human animal with an identification media comprising high salt concentration, a carbohydrate source and a colour based pH indicator; and
  (iii) identifying if coagulase negative Staphylococci is present in the sample,
and wherein, the pH indicator in the reaction mix is present in an amount sufficient to inhibit growth of the coagulase negative Staphylococci if not for the presence of the stabilizing agent,
and wherein, the carbohydrate source in the reaction mix is selected from one or more of the group consisting of glucose fructose, maltose, sucrose, glycerol, galactose, mannose and lactose,
and wherein, identification of coagulase negative Staphylococci is confirmed by a colour change in the reaction mix caused by a change in pH, where identification of coagulase negative Staphylococci in the sample indicates that the human or non-human animal is infected by, or at risk to infection by, coagulase negative Staphylococci.

In an example, the high salt concentration comprises ≥7.5% (w/v) sodium chloride. Alternatively, the high salt concentration comprises ≥7.5% (w/v) potassium chloride or other salts as would be known to a person skilled in the relevant art.

The carbohydrate source is selected from the group consisting of glucose fructose, maltose, sucrose, glycerol, galactose, mannose and, lactose. Importantly, the carbohydrate source does not include mannitol, trehalose, rhamnose, xylose or arabinose.

In a further related example, the pH indicator is selected from the group consisting of phenol red, bromocresol purple, and bromothymol blue. In yet a further example, the pH indicator is phenol red and acidification of the media resulting from bacteria growth causes a colour change from red to yellow.

In yet a further example, the coagulase negative Staphylococci is selected from the group consisting of *Staphylococcus chromogenes, Staphylococcus simulans, Staphylococcus xylosus, Staphylococcus epidermidis, Staphylococcus hemolyticus, Staphylococcus arlettae, Staphylococcus gallinarum, Staphylococcus lentus, Staphylococcus saprophyticus, Staphylococcus warneri/pasteuri, Staphylococcus lugdunensis, Staphylococci schleiferi*, and *Staphylococci caprae*. In one example, the coagulase negative Staphylococci is selected from the group *Staphylococcus epidermidis, Staphylococcus lugdunensis, Staphylococci schleiferi*, and *Staphylococci caprae*.

In one example, the stabilizing agent comprises a milk derived protein or a milk derived protein extract. Examples of milk derived proteins or milk derived protein extracts include, but are not limited to, α-casein, β-casein (including one or more of A1, A2, A3, B, C, D, E and F variants), casein sodium (e.g. comprising α-casein, β-casein and κ-casein), κ-casein, β-lactoglobulin, whey protein, lactalbumin, lactoferrin and milk or milk powder, as well as combinations thereof.

In further examples according to the methods of the present invention, the biological sample is selected from the group consisting of milk, urine, serum, plasma, sputum and faeces.

Importantly, methods according to the present invention are particularly useful, for example, in the identification of bacteria causing mastitis or metritis in humans and non-human animals. In particular, methods of the present invention are useful in the identification of bacteria causing mastitis in bovine animals. For example, in dairy cows.

Accordingly, in yet another aspect of the present invention there is provided a method of identifying one or more bacteria causing mastitis in a human or non-human animal, the method comprising:
  (i) providing a reaction mix comprising a milk sample obtained from a human or non-human animal and identification media; and
  (ii) identifying if one or more bacteria causing mastitis are present in the milk sample according to any of the methods described herein, the modification being that the reaction mix does not require a stabilizing agent.

In a related example, the method according to this aspect of the present invention further comprises identifying other mastitis causing bacteria including, for example, coliform bacteria. An example of a mastitis causing coliform bacteria is *Escherichia coli*.

Accordingly, in yet a further related example, when it is desired to determine if coliform bacteria may be present in a biological sample, including but not limited to milk, the identification media comprises oxbile and a pH indicator, and identification of coliform bacteria in the sample is confirmed by a colour change from red to yellow when the sample is combined with the identification media.

In related example, the identification media comprises MacConkey Broth as a source of oxbile.

In a further related example, the colour based pH indicator is selected from the group consisting of phenol red, bromocresol purple and bromothymol blue.

In yet a further example, the bacteria causing mastitis is selected from the group consisting of *Staphylococcus aureus, Streptococcus uberis, Streptococcus alagactiae, Streptococcus dysagalactiae, Escherichia coli* and coagulase negative *Staphylococci* including *Staphylococcus chromogenes, Staphylococcus simulans, Staphylococcus xylosus, Staphylococcus epidermidis, Staphylococcus hyicus, Staphylococcus hemolyticus, Staphylococcus arlettae, Staphylococcus aureusd, Staphylococcus gallinarum, Staphylococcus lentus, Staphylococcus pseudintermedius, Staphylococcus saprophyticus, Staphylococcus warneri/pasteuri, Corynebacterium bovis, Enterococcus faecalis, Entercoccis faecium, Aerococcus viridans, Enterobacter cloacae, Nocardia* species, *Klebsiella oxttoca, Arcanobacterium pyogenes, Bacillus* species and *Proteus* SPP.

With respect to metritis, the methods according to the first, third and fourth aspects of the present invention may be performed using a fluid sample obtained from the uterus on order to identify the bacteria causing infection.

It is likely that infection of the human or non-human animal is caused by more than one bacterial species. Accordingly, the methods of the present invention may be performed on the same sample in parallel so as to interrogate, on different levels, the nature of the infection. For example, the identification methods described herein may be performed in parallel test strips such that simultaneous, separate or sequential identification of bacteria causing infection may be investigated. Refer to Example 4 for non-limiting examples related to mastitis.

In an example of the bacteria identification methods according to the present invention, the infection is mastitis, and the bacteria causing infection are Group D *Streptococci*. In a related example, the Group D Streptocci includes, but is not limited to, *Streptococcus uberis*.

In another example of the bacteria identification methods according to the present invention, the infection is mastitis, and the bacteria causing infection are Staphylococci. In a related example, the Staphylococci includes, but is not limited to, *Staphylococcus aureus* and coagulase negative Staphylococci.

In yet another example of the bacteria identification methods according to the present invention, the infection is mastitis, and the bacteria causing infection are Group D *Streptococci* and *E. coli* or gram negative bacteria. In a related example, the Group D *Streptococci* includes, but is not limited to, *Streptococcus uberis*.

In a further example of the bacteria identification methods according to the present invention, the infection is mastitis, and the bacteria causing infection are Staphylococci and *E. coli* or gram negative bacteria. In a related example, the Staphylococci includes, but is not limited to, *Staphylococcus aureus* and coagulase negative Staphylococci.

In yet a further example of the bacteria identification methods according to the present invention, the infection is mastitis, and the bacteria causing infection are Group D *Streptococci*, Staphylococci and *E. coli* or gram negative bacteria. In a related example, the Group D *Streptococci* includes, but is not limited to, *Streptococcus uberis*. In a further related example, the Staphylococci includes, but is not limited to, *Staphylococcus aureus* and coagulase negative Staphylococci.

As previously defined, the test strips according to the present invention comprise any configuration of plates, wells, vials or receptacles sufficient to perform the assays and methods of the present invention. This includes for the purpose of identifying bacteria, as well in the performance of antimicrobial susceptibility testing (refer below).

In certain examples according to the present invention, the test strips comprise prefabricated plates (e.g. 96 well microarray plates) comprising test wells, or test wells prefabricated in different configurations such as (e.g.) 1×10, 1×8, 1×6, 1×4, 2×3, 2×5, 3×3, 3×4, 3×8, 4×8, 4×12 etc. In other examples, the test wells, vials or receptacles are pre-filled with the bacteria identification media according to the present invention. This allows the biological sample to be added directly to the test strip and/or test wells for the purpose of enrichment and subsequent identification of bacteria in the sample.

Known bacteria identification test reagents may also be included within separate test wells, vials or receptacles for the purpose of identifying bacteria in the biological sample to be tested. For example, a test well, vial or receptacle may be filled with tryptic soy broth and phenol red to simply establish identification of gram positive and gram negative bacteria in the sample.

2. Antimicrobial Susceptibility Testing

Although it may be advantageous to know information concerning the identity of infection or infectious disease causing bacteria for the purpose of selecting an appropriate antimicrobial for follow on treatment, information concerning the type of bacteria present within a sample obtained from a human or non-human animal is not always sufficient. For example, it is possible that a particular strain of bacteria causing infection has developed drug resistance to conventional antimicrobial agents (e.g. antibiotics) previously known to kill or inhibit the growth of the same bacteria.

Further, certain strains of bacteria may be more susceptible to certain antimicrobials or class(es) of antimicrobials. Accordingly, it would be advantageous to perform real time antibiotic susceptibility testing in an attempt to understand to what extent the bacteria causing infection is/are susceptible to treatment with certain antimicrobial agents. This information may also be used to document effective treatments against historical, seasonal and geographical outbreaks associated with infectious disease, for the purpose of constructing database(s) of information. Moreover, by performing quantitative susceptibility testing, for example through serial dilution analyses, information can be derived with respect to dose optimisation for a follow-on treatment of the infected human or non-human animal.

While the concept of antimicrobial susceptibility testing is known (e.g. Watts et al. (2008) Performance Standards for Antimicrobial Disk and Dilution Susceptibility Tests for Bacteria Isolated from Animals; Approved Standard. Third Edition, 28(8) Clinical and Laboratory Standards Institute, Wayne, Pa., USA), there are limitations associated with existing techniques. For example, conventional laboratory based testing is time consuming (i.e. up to several days) and involves isolation and subsequent culturing of bacteria prior to testing. This is because each test requires a specific inoculum of bacteria. This means that bacteria cultures must be grown to exponential log phase for the reason that a number of antimicrobial agents are only effective against dividing bacteria (e.g. penicillins). Not only is conventional laboratory based testing time consuming, but it also requires expertise in the field of bacteria culturing, isolation and general microbiology. Meanwhile, a patient is either waiting for a result without treatment or is being treated without specific knowledge regarding the bacterial infection. In either situation, there can be negative and even life-threatening consequences for the patient, not to mention contributing to issues associated with drug resistance.

It would be desirable to perform antimicrobial susceptibility testing directly on a biological sample obtained from a human or non-human animal. This approach could be based on a colorimetric test in liquid cultures which can be easily detected and used by a lay person. However, a problem often associated with use of clinical bacterial samples is the background colour due to the infection. In the case of mastitis, for example, this colour can be described as yellow to brown depending on the severity of the infection. Similarly, biological samples comprising urine may contain traces of blood meaning clinical samples may have a red background colour. Faecal samples can be yellow, brown or even contain blood. Such background colour can create difficulties for colorimetric test readings.

Further, there are limitations with using colour indicators at concentrations sufficient to mask any background colour of the sample associated with infection. For example, Tables 2a-2c in Example 2 demonstrate the inhibitory effect of a commonly used colour indicator, phenol red, on bacteria growth. That is, in order to mask any background colour associated with the sample, phenol red may need to be added at concentrations which actually inhibit bacteria growth and therefore enrichment. The result being little if any useful information concerning the potential effectiveness of antimicrobials when colorimetric techniques are applied to antimicrobial susceptibility testing. Accordingly, colorimetric detections are difficult and often require bacteria isolation prior to the application of selective or differential enrichment media. One approach to overcome this issue is to dilute clinical samples e.g. 100 times, 1,000 times or 10,000 times in order to reduce background colour and/or remove inhibitor effects. However, these dilutions are often undesired since it compromises the sensitivity of the susceptibility test. Alternatively, several samples at desired time points are taken and then plated on agar gels for bacteria cell counting. However, this procedure is even more time consuming and difficult for the lay person to achieve.

Applicant has surprisingly discovered that the inhibitory effect of colour based pH indicators against bacteria growth can be effectively suppressed using one or more stabilizing agents, meaning that increased concentrations of pH indicators, such as (e.g.) phenol red, may be used not only in bacteria identification assays but also in antimicrobial susceptibility testing. The advantage of using increased concentrations of colour based indicators means that colorimetric testing may be performed using clinical samples thereby eliminating potential problems associated with (i) having to perform pre-isolation techniques and (ii) background colour contamination caused by infection of samples to be tested.

As such, the present invention provides bacterial antibiotic susceptibility testing that may be performed using growth inhibition assays based on colorimetric change. Further still, the present invention conveniently provides methods and kits that may be used by the lay person in performing antibiotic susceptibility testing for the purpose of selecting an appropriate treatment.

Accordingly, in one aspect of the present invention there is provided a method for performing an antimicrobial susceptibility test on a biological sample obtained from a human or non-human animal, wherein the human or non-human animal may be infected by, or at risk of infection by, one or more infection causing bacteria, the method comprising,
  (i) providing a reaction mix comprising a biological sample obtained from a human or non-human animal and susceptibility media comprising media for growth, an antimicrobial agent, a colour based pH indicator and a stabilizing agent; and
  (ii) determining the susceptibility of the one or more bacteria in the sample to the antimicrobial agent by observing a colour change when the sample is added to the susceptibility media,
wherein, the pH indicator is present in the reaction mix in an amount sufficient to inhibit growth of the one or more infection causing bacteria if not for the presence of the stabilizing agent.

In one example according to this aspect of the present invention, where the bacteria is a gram positive bacteria, the stabilizing agent comprises a milk derived protein or a milk derived protein extract. Examples of milk derived proteins or milk derived protein extracts include, but are not limited to, α-casein, β-casein (including one or more of A1, A2, A3, B, C, D, E and F variants), casein sodium (e.g. comprising α-casein, β-casein and κ-casein), κ-casein, β-lactoglobulin, whey protein, lactalbumin, lactoferrin and milk or milk powder, as well as combinations thereof.

In another example according to this aspect of the present invention, where the bacteria a gram negative bacteria, the stabilizing agent comprises a carbohydrate. Examples of carbohydrates according to this aspect of the present invention include, but are not limited to, dextrose, mannitol, lactose, trehalose and sucrose.

Importantly, the selectivity media must perform two functions, namely (i) support bacteria growth for the purpose of bacteria enrichment, and (ii) include component(s) sufficient to identify susceptibility of bacteria to growth inhibition in the presence of an antimicrobial agent.

In an example of the present invention the colour based pH indicator is selected from the group consisting of phenol red, bromocresol purple, bromothymol blue, bromocresol green, methyl red, methyl purple, azolitmin, neutral red, naphtholphthalein, cresol red, cresolphthalein, phenolphthalein, 2,4-dimitrophenol, erythrosine disodium salt, benzopurpurine 4B, N,N-dimtehyl-p-(m-tolylazo)amiline, p-Dimethylaminoazobenzene, 4,4'-Bis(2-amino-1-naphthylazo)-2, 2'-stilbenedisulfonic acid, tetrabromophenolphthalein ethyl ester potassium salt, bromphenol blue, congo red, methyl orange, ethyl orange, 4-(4-dimethylamino-1-naphylazo)-3-methoxybenzenesulfonic acid, resazurin, 4-phneylazo-1-naphthylamine, ethyl red 2-(p-dimethylaminophenylazo) pyridine, 4-(p-ethoxyphenylazo)-m-phenylene-diamine monohydrochloride, resorcin blue, alizarin red S, propyl red, chlorophenol red, p-nitrophenol, alizarin 2-(2,4-dinitrophenylazo) 1-naphthol-3,6-disulfonic acid disodium salt, 6,8-dinitro-2,4-(1H) quinazolinedione, brilliant yellow, m-nitrophenol, turmeric (curcumin), metacresol purple, 4,4'-Bis(4-amino-1-naphthylazo)-2,2'-stilbenedisulfonic acid, thymol blue, p-naphtholbenzein, phenolphthalein, o-cresolphthalein, ethyl bis(2,4-dimethylphenyl) ethanoate.

In a related example, the colour based pH indicator is selected from the group consisting of phenol red, bromocresol purple and bromothymol blue.

In a further related example of the present invention, the colour based pH indicator is phenol red.

In yet another example, the phenol red is added at between 0.0035 and 0.30%, between 0.005 and 0.1% and 0.01 and 0.1%. In particular, the phenol red is added at a concentration of between 0.0125% and 0.03%. At concentrations of between 0.0035 and 0.30%, the colour of the phenol red is sufficient to mask any background colour associated with the sample to be tested.

Further, the present invention contemplates the use of pH adjusting agents (i.e. acids and bases) sufficient to adjust the pH of the reaction mix to a desired pH immediately prior to addition of the sample to be tested. For example, where it is desired to have a starting pH of 7.2, and the reaction mix sits at 7.0, addition of (e.g.) sodium hydroxide may be made in order to bring the pH to 7.2. These type of pH adjusting modifications would be known to a person skilled in the art.

As previously discussed, the purpose of the stabilizing agent is to suppress the inhibitory effect of the colour based pH indicator on bacteria growth. An example of a suitable stabilizing agent when testing antimicrobial susceptibility against gram positive bacteria is a milk derived protein or a milk derived protein extract, such as (e.g.) α-casein, β-casein (including one or more of A1, A2, A3, B, C, D, E and F variants), casein sodium (e.g. comprising α-casein, β-casein and κ-casein), κ-casein, β-lactoglobulin, whey protein, lactalbumin, lactoferrin and milk or milk powder, as well as combinations thereof. An example of a suitable stabilizing agent when testing antimicrobial susceptibility against gram negative bacteria is a carbohydrate, such as (e.g.) dextrose, mannitol, lactose, trehalose and sucrose. The effect of the stabilizing agent on suppressing the growth inhibitory effect of (e.g.) increased concentrations of phenol red is apparent from the results listed in Tables 4a to 4d, when compared to Tables 2a to 2c.

In addition, it may be desirable to test the effectiveness of the antimicrobial agent, or combination of antimicrobial agents, at different concentrations so as to determine what an effective dose may be in a follow-on treatment.

Accordingly, in one example according to the sixth aspect of the present invention, the step of combining the biological sample with susceptibility media comprising an antimicrobial agent comprises quantitative susceptibility testing. Quantative susceptibility testing is specifically defined herein, and may be achieved using, for example, serial dilution of the antimicrobial agent to be tested or by using pre-selected concentrations of the antimicrobial agent to be tested. Examples of quantitative susceptibility testing according to the present invention are provided in Example 6.

In certain examples according to the sixth aspect of the present invention, the antimicrobial agent is an antibiotic or combination of antibiotics.

In a related example, the antibiotic or combination of antibiotics is selected from the group consisting of penicillins, cephalosporins, macrolides, lincosamides, florfenicol, quinolines, monobactams, tetracyclines, aminoglycosides, sulphonsmides, polymixins and glycopeptides.

In other examples according to the sixth aspect of the present invention, the step of combining the biological sample with the susceptibility media comprises culturing the bacteria for a period of between 7 and 48 h at 25 to 45° C.

The antimicrobial susceptibility methods according to the present invention are performed in less than 24 h, although time periods of less than 12 h, and less than 7 h are desirable. While time to identification ultimately depends on bacteria inoculum in the clinical or biological sample tested, reference is also made to FIG. 1 which shows inhibition of bacterial growth as a function of time. These data indicate that a susceptibility reading at <7 h may provide misleading information, hence the importance of assessing antimicrobial susceptibility over time.

In other examples of the present invention, the antimicrobial susceptibility testing is used to determine the susceptibility of bacteria to antibiotics for the purpose of treating mastitis or metritis. This involves obtaining a milk sample from a human or non-human animal suspected of infection by mastitis or metritis and performing antibiotic susceptibility testing according to the methods of the present. By performing 'real time' antibiotic susceptibility testing on a milk sample obtained from a human or non-human animal, the susceptibility of the infection causing bacteria to certain antibiotics or antibiotic combinations, in addition to any other antimicrobial agents, may be achieved. This approach also eliminates potential problems created by drug resistant bacteria when the antibiotic has been selected exclusively on the basis of bacteria identification analyses. The likelihood of a successful treatment outcome for the human or non-human animal is therefore increased.

Notwithstanding the advantages conferred by antimicrobial susceptibility testing using samples obtained from a human or non-human animal, it might also be useful to determine the identity of bacteria causing infection in parallel to antimicrobial susceptibility testing. For example, in investigating mastitis or metritis. Accordingly, the present invention also contemplates dual methods and test kits to achieve bacteria identification and antibiotic susceptibility testing. Refer to Example 7, which provides examples of combined bacteria identification and susceptibility testing according to the present invention.

As described herein, the purpose of the stabilizing agent is to suppress the inhibitory effect of the colour based pH indicator. An example of a stabilizing agent according to the present invention is milk. Accordingly, in the event that the sample to be tested is milk, for example in the case of susceptibility testing related to mastitis or metritis, then there is no need to include a stabilizing agent.

Accordingly, in another aspect of the present invention there is provided a method for performing antimicrobial susceptibility test on a biological sample comprising milk obtained from a human or non-human animal, wherein the human or non-human animal may be infected by, or at risk of infection by, one or more infection causing bacteria, the method comprising,
  (i) providing a reaction mix comprising a biological sample obtained from a human or non-human animal and susceptibility media comprising an antimicrobial agent and a colour based pH indicator; and
  (ii) determining the susceptibility of the one or more bacteria in the sample to the antimicrobial agent by observing a colour change when the sample is added to the susceptibility media,
wherein, the pH indicator is present in the reaction mix in an amount sufficient to inhibit growth of the one or more infection causing bacteria if not for the presence of the stabilizing agent.

In a related example, the antibiotic selected for antimicrobial susceptibility testing on a sample obtained from a human or non-human animal suspected of being infected by mastitis comprises an antibiotic selected from the group consisting of amoxicillin, ampicillin, benzyl penicillin or penicillin G, carbenicillin, clavulanate, cloxacillin, dicloxacillin, flucloxacillin, methicillin, nafcillin, oxacillin, penethamate, phenoxymethylpenicillin or penicillin V, sulbactam, tazobactam, cefracetrile, cephalexin, cefalotin, cefapirin, cefuroxime, ceftiofur, cefquinome, eyrthromycin, oleandomycin, tylosin, clindamycin, lincomycin, pirlimycin, florfenicol, danofloxacin, difloxacin, enrofloxacin, ibafloxacin, marbofloxacin, orbifloxacin, sarafloxacin, ciprofloxacin, aztreonam, oxytetracycline, tetracycline, dihydrostreptomycin, neomycin, kanamycin, streptomycin, gentamycin, sulfadiazine, sulfamethoxazole, sulfadoxine, and vancomycin.

The basic method of the susceptibility testing according to the present invention involves testing the susceptibility of a microorganism to growth inhibition by a preselected concentration of an antimicrobial product utilizing a test panel with a negative growth control well or receptacle, a positive growth control well or receptacle, and a test well or test receptacle. The term "well" or "receptacle" will be used interchangeably in this specification with the understanding that the term "receptacle" is general to any appropriate structure for holding test analytes. The methods according to the present invention are not dependent upon use of a multiwell panel or a multiwell plate, and separate individual receptacles could be used. The panel or plate approach is preferred for simplicity of handling in and out of incubators and for other reasons that are well known to the skilled person.

An example of how the susceptibility testing could be carried out in accordance with the present invention is described in Examples 2 and 6 which follow. Suitable media for microbial culture includes Tryptic Soy Broth, Mueller Hinton Broth, MacConkey Broth and Esculin Broth among other culture media known in the art. Examples of common enrichment media for the culture of microorganisms according to the present invention are listed in Example 1.

The concentration of the selected growth medium may be in the standard range of concentrations currently used in the susceptibility testing industry.

It is also desirable to provide ready to use antimicrobial susceptibility and/or bacteria identification test kits comprising analytes that have a shelf life adequate to survive shipping and storage over short to medium term periods. Some antimicrobials (e.g.) penicillin or cephalosporin antibiotics degrade in aqueous media when stored at room temperature over time. If degradation of the drug occurs on shelf then the actual drug concentration at the time of testing would be unknown creating potential to provide incorrect information (e.g.) false negative test results.

One approach to circumvent this limitation, being particularly useful in the case of antibiotics, is to provide dried or lyophilised antimicrobial agents, including antibiotics. Another approach is to freeze antimicrobial agents, including antibiotics.

To provide the end-user with a convenient ready to use antimicrobial susceptibility test, antimicrobials must be chemically stabilised for storage. This can be achieved if the antimicrobial of choice (e.g. antibiotic) is included in the test kit together with susceptibility media and stored in the freezer, or if the drug of choice is dried or lyophilised. For example, the susceptibility media comprising a desired antimicrobial may be added to a well of the test kit at the desired concentration, and then dried at 75° C. for 30 min. The susceptibility media, including the antibiotic(s) of choice, are now provided as a dry thin film inside the well or receptacle which can be stored at room temperature for longer periods of time (for example months or years). At the desired time point sampling device can be filled for example with a volume of a clinical sample. The thin film comprising the susceptibility media including antibiotic(s) then reconstitute when susceptibility media is added.

The susceptibility media comprising a desired antimicrobial may be added to a well of the test kit at the desired concentration and then lyophilized (freeze sample to −20° C. at atmospheric pressure, then reduce pressure to (e.g.) 0.001 bar at −20° C. for 24 hours, then increase temperature to 25° C. and hold for 24 hours, then increase pressure to atmospheric pressure). The susceptibility media, including the antibiotic(s) of choice, are now provided as a powder cake inside the well or receptacle which can be stored at room temperature for longer periods of time (for example months or years). At the desired time point sampling device can be filled for example with a volume of a clinical sample. The powder cake comprising the susceptibility media including antibiotic(s) then immediately reconstitutes when the clinical sample is combined with the powder cake.

Accordingly, in an example of the present invention, the selectivity media comprising selected antimicrobial agent(s) exists as a freeze dried or lyophilized form in a test well or receptacle prior to addition of the sample to be tested. This approach enables antibiotics to retain activity over a prolonged shelf life (>months) prior to testing.

By way of non-limiting illustration, it was found that if a general enrichment media such tryptic soy broth containing 0.0125% phenol red forms a relative lose powder/cake after freeze drying which can be easily reconstituted. In this case 20 ul of this medium was freeze dried and then a predetermined volume of milk containing *Streptococcus uberis* 10/\6 cfu/ml was added for reconstitution. The freeze dried enrichment media was reconstituted within minutes and one or two tapping of the vial led to a homogenous mixture by naked eye. This sample was then incubated for ~16 hours. Growth of *Streptococcus uberis* bacteria turned the enrichment media yellow.

As previously defined, the test strips according to the present invention comprise any configuration of plates, wells, vials or receptacles sufficient to perform the assays and methods of the present invention. This includes for the purpose of identifying bacteria, as well in the performance of antimicrobial susceptibility testing (refer below).

In certain examples according to the present invention, the test strips comprise prefabricated plates (e.g. 96 well microarray plates) comprising test wells, or test wells prefabricated in different configurations such as (e.g.) 1×10, 1×8, 1×6, 1×4, 2×3, 2×5, 3×3, 3×4, 3×8, 4×8, 4×12 etc. In other examples, the test wells, vials or receptacles are pre-filled with the bacteria identification media according to the present invention. This allows the biological sample to be added directly to the test strip and/or test wells for the purpose of enrichment and subsequent identification of bacteria in the sample.

3. Antimicrobial Agents

As previously defined, the term "antimicrobial agent" is intended to mean an agent which kills or inhibits the growth of a microorganism, including for example bacteria, yeast, fungi, viruses, parasites, etc.

Examples of antimicrobial agents include, but are not limited to, antibiotics, anti-virals, silver containing compositions, extracts from plants comprising natural antimicrobial agents (e.g.) aloe vera, cranberry, grapefruit peel, green tea, tarragon etc.

Further, examples of suitable antibiotic classes include, but are not limited to, Penicillins, Cephalosporins, Macrolides, Lincosamides, Florfenicol, Quinolones, Monobactams, Tetracyclines, Aminoglycosides, Sulphonamides, Polymixins and Glycopeptides. Examples of specific antibiotics within these classes are listed as follows.

Penicillins including, but not limited to, amoxicillin, ampicillin, azlocillin, benzylpenicillin/penicillin G, carbenicillin, clavulanate, cloxacillin, cyclacillin, dicloxacillin, flucloxacillin, hetacillin, mecillinam, methicillin, mezlocillin, nafcillin, oxacillin, penethamate, phenoxymethylpenicillin/penicillin V, piperacillin, sulbactam, ticarcillin, tazobactam.

Cephalosporins including, but not limited to, cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefclidine, cefepime, cefluprenam, cefoselis, cefozopran, cefpirome, cefquinome, ceftobiprole, ceftaroline, ceftolozane.

Macrolides including, but not limited to, azithromycin, clarithromycin, erythromycin, telithromycin, carbomycin A, josamycin, kitasamycin, midecamycin/midecamycin acetate, oleandomycin, solithromycin, spiramycin, troleandomycin, tylosin, roxithromycin.

Lincosamides including, but not limited to, clindamycin, lincomycin, pirlimycin.

Quinolones including, but not limited to, danofloxacin, difloxacin, enrofloxacin, ibafloxacin, marbofloxacin, orbifloxacin, sarafloxacin, ciprofloxacin.

Monobactams including, but not limited to, aztreonam.

Tetracyclines including, but not limited to, doxycycline, chlortetracycline, clomocycline, demeclocycline, lymecycline, meclocycline, metacycline, minocycline, oxytetracycline, penimepicycline, rolitetracycline, tetracycline.

Aminoglycosides including, but not limited to, dihydrostreptomycin, neomycin, kanamycin, streptomycin, gentamycin.

Sulphonamides including, but not limited to, sulfadiazine, sulfamethoxazole, sulfadoxine.

Polymixins including, but not limited to, polymixin B, colistin.

Glycopeptides including, but not limited to, vancomycin, teicoplanin, avoparcin.

Other Antibiotics including, but not limited to, carbapenems, chloramphenicol, pleuromutilins, polypeptides.

According to the methods and kits of the present invention, antibiotics are used in free form or in various salt forms. For example, benzylpenicillin may be used as a potassium, sodium or procaine salt, cloxacillin as sodium or benzathine salt, ceftiofur as an acid, hydrochloride or sodium salt, cephapirin as a sodium or benzathine salt, cefazolin may be used in free form or as a sodium salt, oxytetracycline as a hydrochloride salt, Neomycin as a trisulfate salt, cephalexin as monohydrate and dihydrostreptomycin as a sulfate salt. Depending on the antibiotic to be used, (e.g.) in susceptibility testing or in a follow-on treatment regime, for example in the treatment of mastitis, the skilled person will know the appropriate form of antibiotic (i.e. free form or particular salt) to use.

In one example according to the present invention, the antibiotics used in susceptibility testing on mastitis milk samples include, but are not limited to, benzylpenicillin as a procaine salt, oxytetracycline as a hydrochloride salt, cephalexin as monohydrate, neomycin as a trisulfate salt, dihydrostreptomycin as a sulfate salt, aztreonam in free form, ceftiofur as hydrochloride and cloxacillin as sodium salt. Further, combinations of antibiotics for use in the methods of the present invention are envisaged. Examples include, but are not limited to, benzylpenicillin as procaine in combination with cloxacillin as sodium, as well as oxytetracycline as hydrochloride in combination with neomycin as trisulfate salt.

4. Test Kits/Articles of Manufacture

The present invention also contemplates kits and test kits comprising test analytes for performing the bacteria identification and antimicrobial susceptibility testing according to the present invention.

Accordingly, the present invention provides a test kit for:
(i) identifying one or more infection causing bacteria in a human or non-human animal, and/or
(ii) for performing antimicrobial susceptibility testing on bacteria causing infection in a human or a non-human animal, the test kit comprising reagents for performing bacteria identification and/or antimicrobial susceptibility testing on a test sample from the human or non-human animal according to any method described herein, together with instructions for use.

The test kits may contain reagents for performing the antimicrobial susceptibility testing and/or bacteria identification in liquid or freeze-dried forms. However, reagents that have been freeze-dried, and which may be rapidly resuspended into solution immediately prior to use, are preferred. This enhances the shelf life of the products. In addition, the freeze-dried reagents and media may further include a moisture scavenging agent such as hydrophilic colloidal silica in order to remove excess moisture/water content. Again, inclusion of a moisture scavenging agent further enhances the shelf life of the test kits according to the present invention.

Typical freeze-drying or lyophilisation methodology comprises the following steps:

Step 1: Solidification
(i) Fill preferred sample container with liquid culture media
(ii) Take sample container filled with media and freeze i.e. at −40 C under atmospheric pressure (this can be done within the freeze drier or in a separate freezer)—step is called solidification (step 1)
(iii) Transfer sample container with frozen media into freeze drier Step 2: Sublimation Drying (Primary Drying)
Pressure lowered, typically less than 100 Pa
Starting temperature −40 C, temperature is continuously increasing to i.e. −10 C, ramp 0.06 C/min then at −10 C temperature is hold for i.e. 8 h Step 3: Desorption Drying (Secondary Drying)
Pressure lowered, typically less than 100 Pa
Starting temperature i.e. −10 C, temperature is continuously increasing to i.e. 40 C, ramp 1.5 C/min then at 40 C temperature is hold for i.e. 6 h Step 4: Sealing (Optional)
Rubber lid is pushed into sample container under lowered pressure to protect freeze dried media Step 5: Increase Pressure to Atmospheric Pressure and Take Out Samples In certain examples according to the present invention, test strips comprising freeze-dried/lyophilised identification media and/or susceptibility testing media (separate tubes) may be prepared in accordance with the methodology described above. The test strips may then be shipped to the point of use (e.g. on farm), where biological samples (e.g. milk) may be added to create the reaction mix for phenotypic screening.

In accordance with the teaching of this specification, the skilled person will recognise that the test strips comprise different reagents (identification/susceptibility media) depending on the nature of the application and the bacteria to be (i) potentially identified and/or (ii) screened for susceptibility to antimicrobial agent(s).

For example, and by way of illustration only, antibiotic susceptibility test strips are packaged to contain freeze-dried growth media (e.g. tryptic soy broth), antibiotic(s) (e.g. benzylpenicillin; in serial dilutions), pH indicator (e.g. phenol red) and optionally a stabilising agent (e.g. one or more caseins). The test strips are then sealed in aluminium pouches or plastic pouches or plastic pouches under vacuum and/or containing silica gel sachets (moisture scavengers) and shipped to a desired test site. Addition of a test sample (e.g. biological sample; refer above) will result in resuspension of the susceptibility media providing a reaction mix in accordance with the methods described herein.

EXAMPLES

Example 1: Materials and Methods

1. Common Enrichment Media for Bacteria Culture

| Tryptic Soy Broth (pH~7.3) (% w/v) | |
| --- | --- |
| Tryptone (Pancreatic Digest of Casein) | 1.7% |
| Soytone (Pancreatic diagest of soybean meal) | 0.3% |
| Glucose (=Dextrose) | 0.25% |
| Sodium Chloride | 0.5% |
| Dipotassium hydrogen phosphate | 0.25% |
| Water | 97.0% |
| MacConkey Broth (pH ~7.3) (% w/v) | |
| Enzymatic digest of gelatine | 2.0% |
| Lactose | 1.0% |
| Oxbile | 0.5% |
| Bromocresol Purple | 0.001% |
| Water | 96.499% |

| Esculin Agar (% w/v) | |
| --- | --- |
| Agar | 1.5% |
| Pacreatic digest of casein | 1.3% |
| NaCl | 0.5% |
| Yeast Extract | 0.5% |
| Heart muscle, solids from infusion | 0.2% |
| Esculin | 0.1% |
| Ferric citrate | 0.05% |
| Water | 95.85% |

| Esculin Azide Broth (pH ~7.2) (% w/v) | |
| --- | --- |
| Peptic digest of animal tissue | 2.0% |
| Yeast Extract | 0.5% |
| Bile salts | 1.0% |
| Sodium citrate | 0.1% |
| Esculin | 0.1% |
| Ferric ammonium citrate | 0.05% |
| Sodium Azide | 0.025% |
| Water | 96.225% |

| Mannitol Salt Agar (% w/v) | |
| --- | --- |
| Agar | 1.5% |
| Enzymatic digest of casein | 0.5% |
| Enzymatic digest of animal tissue | 0.5% |
| Beef Extract | 0.1% |
| D-Mannitol | 1.0% |
| Sodium Chloride | 7.5% |
| Phenol red | 0.0025% |
| Water | 88.8975% |

| Mannitol Salt Broth (pH ~7.3) (% w/v) | |
| --- | --- |
| Mannitol | 0.25% |
| Sodium Chloride | 10% |
| Soy peptone | 0.3% |
| Casein peptone | 1.275% |
| Gelatine peptone | 0.425% |
| Phenol red | 0.0025% |
| Dipotassium phosphate | 0.25% |
| Water | 87.4975% |

| Baird Parker Agar (% w/v) | |
| --- | --- |
| Tryptone | 1% |
| Beef extract | 0.5% |
| Yeast extract | 0.1% |
| Glycine | 1.2% |
| Sodium pyruvate | 1.0% |
| Lithium Chloride | 0.5% |
| Agar | 1.5% |
| Water | 94.2% |

+50 mL egg yolk tellurite emulsion per liter

| Giolitti Cantoni broth base (% w/v) pH ~6.9 | |
| --- | --- |
| Tryptone | 1% |
| Beef extract | 0.5% |
| Yeast extract | 0.5% |
| D-Mannitol | 2% |
| Sodium chloride | 0.5% |
| Lithium chloride | 0.5% |
| Glycine | 0.12% |
| Sodium pyruvate | 0.3% |
| Water | 94.58% |

Add 1.05 mL (~5.24%) or when tested for meat add 0.105 mL (~0.55%) Tellurite solution 1% in 19 mL Giolitti Cantoni broth base

| Mueller Hinton Broth (% w/v) | |
| --- | --- |
| Acid Hydrolysate of Casein | 1.75% |
| Beef Extract | 0.3% |
| Starch | 0.15% |
| Water | 97.9% |

2. Bacteria Samples

Bacteria Sample 1:
  *Escherichia coli* in tryptic soy broth/cfu/mL
  a) ~$10^8$; b) ~$10^7$; c) ~$10^6$; d) ~$10^5$; e) ~$10^4$; f) ~$10^3$; g) ~$10^2$ Bacteria Sample 2:
  *Staphylococcus aureus* in tryptic soy broth/cfu/mL
  a) ~$10^8$; b) ~$10^7$; c) ~$10^6$; d) ~$10^5$; e) ~$10^4$; f) ~$10^3$; g) ~10~2

Bacteria Sample 3:
  *Streptococcus uberis* in tryptic soy broth/cfu/mL
  a) ~$10^8$; b) ~$10^7$; c) ~$10^6$; d) ~$10^5$; e) ~$10^4$; f) ~$10^3$; g) ~$10^2$ Bacteria Sample 4:
  *Escherichia coli* in full fat processed milk/cfu/mL
  a) ~$10^8$; b) ~$10^7$; c) ~$10^6$; d) ~$10^5$; e) ~$10^4$; f) ~$10^3$; g) ~$10^2$ Bacteria Sample 5:
  *Staphylococcus aureus* in full fat processed milk/cfu/mL
  a) ~$10^8$; b) ~$10^7$; c) ~$10^6$; d) ~$10^5$; e) ~$10^4$; f) ~$10^3$; g) ~$10^2$; h) ~$10^{6.5}$ Bacteria Sample 6:
  *Streptococcus uberis* in full fat processed milk/cfu/mL
  a) ~$10^8$; b) ~$10^7$; c) ~$10^6$; d) ~$10^5$; e) ~$10^4$; f) ~$10^3$; g)

Bacteria Sample 7:
  *Staphylococcus epidermidis* (coagulase negative) in full fat processed milk/cfu/mL
  a) ~$10^8$; b) ~$10^7$; c) ~$10^6$; d) ~$10^5$; e) ~$10^4$; f) ~$10^3$; g) ~$10^2$; h) ~$10^{6.5}$ Bacteria Sample 8 (% v/v) (no bacteria)
  Full fat processed milk 100%

Bacteria Sample 9:
  *Streptococcus Agalactiae* in full fat processed milk/cfu/mL
  a) ~$10^6$; b) ~$10^3$;

Bacteria Sample 10:
  *Escherichia coli* in urine/cfu/mL
  a) $10^7$; b) $10^5$; c) $10^3$ Bacteria Sample 11:
  *Streptococcus uberis* in urine/cfu/mL
  a) $10^7$; b) $10^5$; c) $10^3$ Bacteria Sample 12:
  *Staphylococcus epidermidis* in tryptic soy broth/cfu/mL
  a) $10^7$; b) $10^5$ 3. Clinical Bacteria Samples from Bovine Mastitis
  Sample ID: 1 to 8 obtained from a farm in South Island, New Zealand.

4. Compositions

| Composition 1: (% w/v) | |
| --- | --- |
| MacConkey broth single strength | 99.9875% |
| Phenol red | 0.0125% |

| Composition 2 (% w/v) | (a) | (b) | (c) | (d) | (e) |
| --- | --- | --- | --- | --- | --- |
| Tryptic soy broth | 99.9985% | 99.995% | 99.9875% | 99.975% | 99.95% |
| Phenol red | 0.0015% | 0.005% | 0.0125% | 0.025% | 0.05% |

-continued

| Composition 3 (% w/v) | | | | |
|---|---|---|---|---|
| Tryptic soy broth | 99.96% | | | |
| Bromocresol Purple | 0.04% | | | |
| Composition 4 (% w/v) | (a) | (b) | (c) | (d) |
| Tryptic soy broth | 99.85% | 98.5% | 97% | 92.5% |
| Esculin | 0.1% | 1.0% | 2.0% | 5.0% |
| Ammonium ferric citrate | 0.05% | 0.5% | 1% | 2.5% |
| Composition 5 (% v/v) | | | | |
| Giolitti Cantoni broth | 98.77% | | | |
| 1% w/v potassium tellurite solution | 1.23% | | | |
| Composition 6 (% v/v) | | | | |
| Giolitti Cantoni broth | 98.0% | | | |
| 1% w/v potassium tellurite solution | 2.0% | | | |
| Composition 7 (% v/v) | | | | |
| Giolitti Cantoni broth | 83.33% | | | |
| 1% w/v potassium tellurite solution | 16.67% | | | |
| Composition 8 (% v/v) | | | | |
| Giolitti Cantoni broth | 88.89% | | | |
| 1% w/v potassium tellurite solution | 11.11% | | | |
| Composition 9 (% v/v) | | | | |
| Mannitol Salt broth | 98.77% | | | |
| 1% w/v potassium tellurite solution | 1.23% | | | |
| Composition 10 (% v/v) | | | | |
| Mannitol Salt broth | 93.02% | | | |
| 0.1% w/v potassium tellurite solution | 6.98% | | | |
| Composition 11 (% v/v) | | | | |
| Mannitol Salt broth | 100% | | | |
| Composition 12 (% v/v) | | | | |
| Mannitol Salt broth | 49.385% | | | |
| Distilled water | 49.385% | | | |
| 1% w/v potassium tellurite solution | 1.23% | | | |
| Composition 13 (% v/v) | | | | |
| Mannitol Salt broth | 50% | | | |
| Distilled water | 50% | | | |
| Composition 14 (% w/v) | | | | |
| Mannitol Salt broth | 98.75% | | | |
| Lactose | 1.25% | | | |
| Composition 15 (% w/v) | | | | |
| Tryptic soy broth | 96.362% | | | |
| Phenol Red | 0.025% | | | |
| 1% w/v potassium tellurite solution | 3.614% | | | |
| Composition 16 (% w/v) | | | | |
| Tryptic soy broth | 96.374% | | | |
| Phenol Red | 0.0125% | | | |
| 1% w/v potassium tellurite solution | 3.614% | | | |
| Composition 17 (% w/v) | | | | |
| Tryptic soy broth | 93.0% | | | |
| Phenol Red | 0.023% | | | |
| 1% w/v potassium tellurite solution | 6.977% | | | |
| Composition 18 (% w/v) | | | | |
| Tryptic soy broth | 99.625% | | | |
| Esculin | 0.25% | | | |
| Ammonium ferric citrate | 0.125% | | | |
| Composition 19 (% w/v) | | | | |
| MacConkey broth | 99.975% | | | |
| Phenol Red | 0.025% | | | |
| Composition 20 (% v/v) | | | | |
| Giolitti Cantoni broth base | 93.82% | | | |
| 1% w/v potassium tellurite solution | 6.18% | | | |

| Composition 21 (% v/v) | |
|---|---|
| Mannitol salt broth | 75.0% |
| 0.1% w/v potassium tellurite solution | 6.56% |
| 10% w/v Lithium Chloride solution | 6.25% |
| 10% w/v Glycine solution | 1.5% |
| Distilled water | 10.69% |

| Composition 22 (% w/v) | |
|---|---|
| Tryptic soy broth | 99.625% |
| Esculin | 0.5% |
| Ammonium ferric citrate | 0.25% |

| Composition 23 (% w/v) | |
|---|---|
| MacConkey broth | 98.98% |
| Phenol Red | 0.02% |
| Cloxacillin sodium | 1.0% |

| Composition 24 (% w/v) | |
|---|---|
| Tryptic soy broth | 99.98% |
| Phenol Red | 0.02% |

| Composition 25 (% w/v) | |
|---|---|
| Tryptic soy broth | 98.56% |
| Esculin | 0.22% |
| Ammonium ferric citrate | 0.11% |
| 1% w/v Gentamycin | 1.11% |

| Composition 26 (% w/v) | |
|---|---|
| Mueller Hinton broth | 99.9875% |
| Phenol red | 0.0125% |

| Composition 27 (% w/v) | |
|---|---|
| Tryptic soy broth | 99.2375% |
| Esculin | 0.5% |
| Ammonium ferric citrate | 0.25% |
| Phenol red | 0.0125% |

| Composition 28 (% w/v) | (a) | (b) | (c) | (d) |
|---|---|---|---|---|
| Tryptic soy broth | 99.85% | 99.85% | 99.94% | 99.95% |
| Phenol red | 0.05% | 0.05% | 0.05% | 0.05% |
| Triton x 100 | 1.0% | 0.1% | 0.01% | 0% |

Compositions 29-54 are listed in Table 90.

| Composition 55 | g | g |
|---|---|---|
| Phenol Red | 0.0125% | 0.001 |
| Mannitol Salt Broth | 8.0% | 0.800 |
| water (sterile) | 91.9875% | 9.199 |
| Total volume | 100.0% | 10.000 |

| Composition 56 | % |
|---|---|
| Mannitol | 3.39% |
| Glycine | 0.21% |
| Lithium chloride | 0.17% |
| sodium pyruvate | 0.51% |
| Tryptic soy broth | 95.72% |
| Total | 100.00% |

| Composition 57 | |
|---|---|
| Compsoition 56 | 90.0% |
| 1% Potassium tellurite solution | 10.0% |

| Composition 58 | |
|---|---|
| Mannitol | 3.39% |
| Glycine | 0.21% |
| Lithium chloride | 0.17% |
| sodium pyruvate | 0.51% |
| Hydrophilic colloidal silica | 5.00% |
| Tryptic soy broth | 90.72% |
| Total | 100.00% |

| Composition 59 | |
|---|---|
| Compsoition 60 | 78.1% |
| 1% Potassium tellurite solution | 21.9% |

Example 2: Antibiotic Susceptibility Testing

1. Preliminary Experiments Based on Test Development and Validation

In this example, the following abbreviations are used: McC=MacConkey broth; TSB=tryptic soy broth Gram negative bacteria including *E. coli* in MacConkey broth plus addition phenol red (enrichment media for coliform bacteria); MacConkey Broth is used for the detection of coliform bacteria in milk and water.

| Formula for MacConkey broth g/L | |
|---|---|
| Enzymatic Digest of Gelatin | 20 g |
| Lactose | 10 g |

| Formula for MacConkey broth g/L | |
| --- | --- |
| Oxbile | 5 g |
| Bromocresol Purple | 0.01 g |

If gram negative bacteria including *E. coli* is grown in MacConkey broth plus excess of phenol red then as expected the colour is initially red and turns yellow with the growth of bacteria. Importantly, the yellow colour remains for up to 48 h. Refer to Table 1, below.

Table 2a shows *E. coli* grown in a general enrichment media, which is required for antibiotic susceptibility testing. The results demonstrate that with increasing phenol red concentration the intensity of red increases and so does the response colour yellow (data not shown). For the sake of simplicity, the results described herein simply indicate red or yellow. However, the kinetics associated with colour change can be measured. Refer later.

As expected, when *E. coli* is grown in general enrichment media, a colour change from red to yellow occurs. However, the colour change to is not stable, degrading from yellow back to orange/red after ~11.5 h. While there may be some discernable difference between the shades of red at T=0 and T=24, this is not desirable. Further, given the bacteria growth inhibitory effect of many colour based pH indicators, it is also not desirable to simply add more (e.g.) phenol red to the test for the reason that. This is illustrated in Tables 2b and 2c where the growth of *Staphylococcus aureus* and *Streptococcus uberis* was investigated as a function of increasing concentration of phenol red.

Importantly, the success of a colorimetric test relies on a stable colour change that remains throughout the sampling window. In the case of bacterial identification and/or antibiotic susceptibility testing a sampling window of ~24 h is desired.

The present invention overcomes these limitations through inclusion of one or more stabilizing agents which suppresses the potential inhibitory effect of the colour based pH indicator. As such, increased concentrations of the colour based pH indicator (e.g. phenol red) may be used in the test, thereby achieving stability in the colour change associated with bacteria growth. An example of a stabilizing agent according to the present invention is milk.

2. Antibiotic Susceptibility Testing

In this Example, liquid culture media is used which allows early and easy identification of susceptible antimicrobials to support decision of antimicrobial selection to treat bacterial infections. It also allows the detection of bacteria such as gram+ and/or gram-bacteria in clinical samples are present and/or allows estimation of the inoculum from kinetic analyses of colour change. The base of this liquid culture medium is a general purpose liquid enrichment medium for example tryptic soy broth (Soybean-Casein Digest Medium) but could also be Mueller Hinton broth. This TSB media has excess concentration of a pH indicator such as phenol red and/or bromocresol purple and milk. Such culture media is then mixed with a clinical sample from human or animal such as raw milk, urine, faeces, blood, sputum or other types of swap samples. If the clinical sample is a milk sample then no additional milk is required. Colorimetric analyses can performed by the naked eye or by an optical reader for example via CCD camera chip or photo diode.

In the Tables which follow, an approximate inoculum of bacteria in the sample tested is given. For example, $10^{\wedge}6$, $10^{\wedge}7$ and $10^{\wedge}8$. The skilled person would recognise that an inoculum of $10^{\wedge}8$ is approximate, and may represent by way of non-limiting example $7.6 \times 10^{\wedge}7$ or $8.4 \times 10^{\wedge}8$.

TABLE 1

| 80 μl Composition 1 + 20 μl Bacteria sample 1a, 1c or 1e | | | | | | | | | | | | | | |
| --- | --- | --- | --- | --- | --- | --- | --- | --- | --- | --- | --- | --- | --- | --- |
| *E-Coli* | t = 0 h | | | t = 5 h | | | t = 16 h | | | t = 24 h | | | t = 48 h | | |
| Inoculum cfu/ml | $10^8$ | $10^6$ | $10^4$ | $10^8$ | $10^6$ | $10^4$ | $10^8$ | $10^6$ | $10^4$ | $10^8$ | $10^6$ | $10^4$ | $10^8$ | $10^6$ | $10^4$ |
| Composition 1 | red | red | red | Orange | red | red | yellow | yellow | yellow | yellow | yellow | yellow | yellow | yellow | yellow |

TABLE 2a

| 80 μl Composition 2a, 2b, 2c, 2d or 2e + 20 μl Bacteria sample 1b, 1d or 1f | | | | | | | | | | | | | | |
| --- | --- | --- | --- | --- | --- | --- | --- | --- | --- | --- | --- | --- | --- | --- |
| *E-Coli* | t = 0 h | | | t = 5 h | | | t = 7 h | | | t = 11.5 h | | | t = 23.5 h | | |
| Inoculum cfu/ml | $10^7$ | $10^5$ | $10^3$ | $10^7$ | $10^5$ | $10^3$ | $10^7$ | $10^5$ | $10^3$ | $10^7$ | $10^5$ | $10^3$ | $10^7$ | $10^5$ | $10^3$ |
| Composition 2a | pink | pink | pink | yellow | yellow | pink | yellow | yellow | pink | yellow | yellow | yellow | orange | orange | orange |
| Composition 2b | red | red | red | yellow | orange | red | yellow | yellow | red | yellow | yellow | yellow | pink | pink | pink |
| Composition 2c | red | red | red | yellow | orange | red | yellow | yellow | red | orange | orange | orange | red | red | red |
| Composition 2d | red | red | red | red | red | red | orange | red | red | orange | red | red | red | orange | red |
| Composition 2e | red | red | red | orange | red | red | orange | red | red | orange | orange | orange | red | red | red |

TABLE 2b

| 80 μl Composition 2a, 2b, 2c, 2d or 2e + 20 μl Bacteria sample 2h, 2d or 2f | | | | | | | | | | | | | | |
| --- | --- | --- | --- | --- | --- | --- | --- | --- | --- | --- | --- | --- | --- | --- |
| *Staph aureus* | t = 0 h | | | t = 5 h | | | t = 7 h | | | t = 11.5 h | | | t = 23.5 h | | |
| Inoculum cfu/ml | $10^7$ | $10^5$ | $10^3$ | $10^7$ | $10^5$ | $10^3$ | $10^7$ | $10^5$ | $10^3$ | $10^7$ | $10^5$ | $10^3$ | $10^7$ | $10^5$ | $10^3$ |
| Composition 2a | pink | pink | pink | yellow | pink | pink | yellow | orange | pink | yellow | yellow | yellow | yellow | yellow | yellow |
| Composition 2b | red | red | red | yellow | red | red | yellow | orange | red | yellow | yellow | yellow | yellow | yellow | yellow |

TABLE 2b-continued

| Staph aureus | 80 μl Composition 2a, 2b, 2c, 2d or 2e + 20 μl Bacteria sample 2h, 2d or 2f | | | | | | | | | | | | | | |
|---|---|---|---|---|---|---|---|---|---|---|---|---|---|---|---|
| | t = 0 h | | | t = 5 h | | | t = 7 h | | | t = 11.5 h | | | t = 23.5 h | | |
| Inoculum cfu/ml | 10^7 | 10^5 | 10^3 | 10^7 | 10^5 | 10^3 | 10^7 | 10^5 | 10^3 | 10^7 | 10^5 | 10^3 | 10^7 | 10^5 | 10^3 |
| Composition 2c | red | red | red | yellow | red | red | yellow | orange | red | yellow | yellow | red | yellow | yellow | yellow |
| Composition 2d | red | red | red | red | red | red | orange | red | red | orange | red | red | yellow | red | red |
| Composition 2e | red | red | red | red | red | red | orange | red | red | red | red | red | red | red | red |

TABLE 2c

| Strep uberis | 80 μl Composition 2a, 2b, 2c, 2d or 2e + 20 μl Bacteria sample 3b, 3d or 3f | | | | | | | | |
|---|---|---|---|---|---|---|---|---|---|
| | t = 0 h | | | t = 6.5 h | | | 18.5 h | | |
| Inoculum cfu/ml | 10^7 | 10^5 | 10^3 | 10^7 | 10^5 | 10^3 | 10^7 | 10^5 | 10^3 |
| Composition 2a | pink | Pink | pink | yellow | yellow | pink | yellow | yellow | yellow |
| Composition 2b | red | Red | red | yellow | yellow | red | yellow | yellow | yellow |
| Composition 2c | red | Red | red | yellow | yellow | red | yellow | yellow | yellow |
| Composition 2d | red | Red | red | red | red | red | yellow | red | red |
| Composition 2e | red | Red | red | red | red | red | red | red | red |

TABLE 3

| E. coli | E. coli in 80 ul McC/20 ul Milk; inoculum refers to cfu/ml in milk. | | | | | | | | | | | | | | |
|---|---|---|---|---|---|---|---|---|---|---|---|---|---|---|---|
| | t = 0 h | | | t = 5 h | | | t = 16 h | | | t = 24 h | | | t = 48 h | | |
| Inoculum cfu/ml | 10^8 | 10^6 | 10^4 | 10^8 | 10^6 | 10^4 | 10^8 | 10^6 | 10^4 | 10^8 | 10^6 | 10^4 | 10^8 | 10^6 | 10^4 |
| Composition 1 | red | red | red | yellow | red | red | yellow | yellow | yellow | yellow | yellow | yellow | yellow | yellow | yellow |

TABLE 4a

| E-Coli Inoculum | E. coli in 80 ul TSB/20 ul Milk; inoculum refers to cfu/ml in milk. | | | | | | | | | | | | | | |
|---|---|---|---|---|---|---|---|---|---|---|---|---|---|---|---|
| | t = 0 h | | | t = 5 h | | | t = 7 h | | | t = 11.5 h | | | t = 23.5 h | | |
| cfu/ml | 10^7 | 10^5 | 10^3 | 10^7 | 10^5 | 10^3 | 10^7 | 10^5 | 10^3 | 10^7 | 10^5 | 10^3 | 10^7 | 10^5 | 10^3 |
| Composition 2d | red | red | red | yellow | orange | red | yellow | yellow | orange | yellow | yellow | yellow | yellow | yellow | yellow |
| Composition 2e | red | red | red | yellow | orange | red | yellow | yellow | red | yellow | yellow | yellow | yellow | yellow | yellow |

TABLE 4b

| Staph aureus | Staphylococcus aureus in 80 ul TSB/20 ul Milk; inoculum refers to cfu/ml in milk. | | | | | | | | | | | | | | |
|---|---|---|---|---|---|---|---|---|---|---|---|---|---|---|---|
| | t = 0 h | | | t = 5 h | | | t = 7 h | | | t = 11.5 h | | | t = 23.5 h | | |
| Inoculum cfu/ml | 10^7 | 10^5 | 10^3 | 10^7 | 10^5 | 10^3 | 10^7 | 10^5 | 10^3 | 10^7 | 10^5 | 10^3 | 10^7 | 10^5 | 10^3 |
| Composition 2d | red | red | red | orange | red | red | orange | red | red | yellow | yellow | red | yellow | yellow | yellow |
| Composition 2e | red | red | red | orange | red | red | orange | red | red | yellow | yellow | red | yellow | yellow | yellow |

TABLE 4c

Strep uberis in 80 ul TSB/20 ul Milk; inoculum refers to cfu/ml in milk.

| | Strep uberis | | | | | | | | |
|---|---|---|---|---|---|---|---|---|---|
| | t = 0 h | | | t = 6.5 h | | | 18.5 h | | |
| Inoculum cfu/ml | 10^7 | 10^5 | 10^3 | 10^7 | 10^5 | 10^3 | 10^7 | 10^5 | 10^3 |
| Composition 2d | red | Red | red | yellow | yellow | orange | yellow | yellow | yellow |
| Composition 2e | red | Red | red | yellow | yellow | orange | yellow | yellow | yellow |

TABLE 4d

Staphylococci epidermidis (coagualase negative Staph - CNS) in 80 ul TSB/20 ul Milk: inoculum refers to cfu/ml in milk.

| | Staph epidermidis | | | | | | | | |
|---|---|---|---|---|---|---|---|---|---|
| | t = 0 h | | | t ~16 h | | | 24 h | | |
| Inoculum cfu/ml | 10^8 | 10^6 | 10^4 | 10^8 | 10^6 | 10^4 | 10^8 | 10^6 | 10^4 |
| Composition 2d | red | red | red | yellow | yellow | orange | yellow | yellow | yellow |

TABLE 4e

Strep uberis in 80 ul TSB/20 ul Milk with Bromocresol purple as pH indicator; inoculum refers to cfu/ml in milk.

| | Strep uberis | | | | | | |
|---|---|---|---|---|---|---|---|
| Inoculum cfu/ml | 10^8 | 10^7 | 10^6 | 10^5 | 10^4 | 10^3 | 10^2 |
| | t = 0 h | | | | | | |
| Composition 3 | Purple | purple | purple | purple | purple | purple | purple |
| | t ~16 h | | | | | | |
| Composition 3 | yellow | yellow | yellow | yellow | yellow | yellow | yellow |

If colour change occurs then this happens gradually which can be monitored. The starting point of colour change depends on inoculum. Thus a kinetic colour change curve can be determined over time and an estimated initial inoculum calculated.

In the presence of a stabilizing agent, phenol red may be included at a concentration of between 35 ug/ml and 3000 ug/ml, between 50 ug/ml and 1000 ug/ml, and in particular between 100 ug/ml and 500 ug/ml in combination with milk or milk powder as the stabilizing agent.

According to the antibiotic susceptibility testing examples outlined below, testing was performed using (clinical) samples for up to 24 hours.

The stabilizing agent included in the examples below was processed milk (dark blue top) and therefore possessed a white colour.

Table 3 shows E. coli in 80 ul McC/20 ul Milk; inoculum refers to cfu/ml in milk. As expected, the results in Table 3 align with Table 1.

Table 4a shows E. coli in 80 ul TSB/20 ul Milk; inoculum refers to cfu/ml in milk. Surprisingly, results in table 4a show practically no impact of phenol red concentration on colour change (except at 7 h and an inoculum of 10^3 cfu/ml). Colour change remained constant between 11.5 h and 23.5 h which is the crucial time period despite excess amount of phenol red. This is unexpected when compared against the data in Table 2a and points to the stabilizing effect of milk in suppressing the inhibitory effect of increased concentrations of phenol red.

Surprisingly, results in Table 4b show no inhibition of Staphylococcus aureus in presence of different phenol red concentrations at 23.5 h. Prior time points, a few cases of phenol red concentration of 0.25 mg/ml and above show a slight delay of colour response. Again these results are unexpected when compared against the data in Table 2b.

Similarly, Table 4c shows that growth of Streptococci uberis is independent of the different phenol red concentration. Again, these results are unexpected compared against the data in Table 2c.

As shown in Table 4d, the same result is also achieved for Staphylococcus epidermidis, a coagulase negative bacteria.

As shown in Table 4e, excess concentration bromocresol purple does not inhibit growth of Streptococcus uberis across all the inoculums investigated. Interestingly, typical concentrations of bromocresol purple in typical enrichment media such as MacConkey broth are in the order of ~40 times less.

Collectively and surprisingly, these data show that the growth inhibitory effect observed using increased concentrations of colour based pH indicators may be suppressed in the presence of a stabilizing agent, for example milk. Accordingly, increased concentrations of colour based pH indicators may be used to provide a robust colorimetric test for the purpose of assessing the susceptibility of bacteria to one or more antimicrobials.

Example 3: Streptococci Group D Identification in Clinical Samples

Esculin agar or esculin broth or other typical esuclin containing culture media contain esculin alone or in combination with ferric citrate. This media can be used for the cultivation and differentiation of bacteria based on their ability to hydrolyze esculin. Example compositions of esculin agar or broth according to the present invention include:

| Esculin Agar Composition per liter: | |
| --- | --- |
| Agar | 15.0 g |
| Pancreatic digest of casein | 13.0 g |
| NaCl | 5.0 g |
| Yeast extract | 5.0 g |
| Heart muscle, solids from infusion | 2.0 g |
| Esculin | 1.0 g |
| Ferric citrate | 0.5 g |
| Esculin Azide Broth Composition per liter: | |
| Peptic digest of animal tissue | 20.0 g |
| Yeast extract | 5.0 g |
| Bile salts | 10.0 g |
| Sodium citrate | 1.0 g |
| Esculin | 1.0 g |
| Ferric ammonium citrate | 0.5 g |
| Sodium azide | 0.25 g |

Final pH (at 25° C.) 7.2 ± 0.2

Group D Streptococci, for example Streptococcus uberis, hydrolyse esculin to esculetin and dextrose, which reacts with ferric citrate producing brown/blackening of the culture media. The typical esculin concentration present in enrichment media is 0.1% and 0.05% for ferric citrate. In the context of this Example, ferric citrate here means ammonium ferric citrate but other forms may be used.

However, higher concentrations of esculin and/or ferric citrate can lead to inhibition of bacteria growth. To illustrate this points, Group D Streptococci, and in particular Streptococcus uberis, were grown in Tryptic Soy Broth in the presence of (i) 0.1% esculin and 0.05% ferric citrate, (ii) 1.0% esculin and 0.5% ferric citrate (iii) 2.0% esculin and 1.0% ferric citrate and (iv) 5.0% esculin and 2.5% ferric citrate. Briefly, Streptococcus uberis was dispersed and grown in Trypic Soy Broth (TSB) and then 20 uL dilutions were mixed with 100 uL TSB containing esculin and ferric citrate concentrations as shown in Table 5 (at inoculums of ~10^6 and ~10^4 cfu/mL). The colour of the initial Streptococcus uberis esculin/ferric citrate media was transparent yellow. Colour was checked after ~16 h and ~48 h. The results are summarised in Table 5.

TABLE 5

Streptococcus uberis in 100 uL esculin/ferric citrate/TSB media; 80 uL TSB/esculin/ferric citrate + 20 uL bacteria in TSB(2); inoculum refers to cfu/mL in TSB(2)

| | 10^6 cfu/ml | 10^4 cfu/ml |
| --- | --- | --- |
| 0.1% esculin + 0.05% ferric citrate | black | black |
| 1% esculin + 0.5% ferric citrate | not black | not black |
| 2% esculin + 1% ferric citrate | not black | not black |
| 5% esculin + 2.5% ferric citrate | not black | not black |

These data show that inhibition of Streptococcus uberis growth is between 0.1% esculin and 0.05% ferric citrate, and between 1.0% esculin and 0.5% ferric citrate in enrichment media comprising TSB.

However, there is a limitation in using the same approach on clinical samples, since clinical samples can take on a strong background colour caused by the infection (e.g. infected by Group D Streptococci). In other words, detection of a black/brown precipitate produced by Group D Streptococci in the presence of esculin and ferric citrate may be masked by the background colour associated with the clinical sample.

Based on the results presented in Table 5, it is not possible to simply increase the concentration of esculin (i.e. >1.0%) and ferric citrate (i.e. >0.5%) in the sample to increase detection of a precipitate, owing to the growth inhibitory effect(s) of these analytes.

Surprisingly, Applicant has discovered that inclusion of a stabilizing agent (e.g. milk) can suppress the growth inhibitory effect of esculin and ferric citrate at significantly increased concentrations.

By way of illustration, the same experiment was conducted as above, only this time using clinical milk samples obtained from a bovine animal suspect of being infected with mastitis.

Even for clinical milk samples that appeared "white", Applicant observed that the colour response was weak compared to the same result achieved using TSB comprising reduced concentrations of esculin and ferric citrate (i.e. 0.1% esulin and 0.05% ferric citrate). Despite attempts to produce a useful result by spiking milk samples with Streptococcus uberis (data not shown).

However, Applicant has discovered that increased amounts of esculin and ferric citrate may be used in milk derived clinical samples. For example, at concentrations of at least 2% esculin and 1% ferric citrate, the growth of Streptococcus uberis is not inhibited. These data are presented in Table 6, by reference to the formation of a blackening of the culture media (refer to description of chemistry above). Contrast these data with the similar experiments conducted in the presence of TSB (Table 5).

Accordingly, Applicant has surprisingly discovered that a component of the milk suppresses the growth inhibitory properties of esculin and ferric citrate thereby stabilizing formation of a blackening of the culture media in the presence of Group D Streptococci. Identification of Group D Streptococci is therefore possible, even where the clinical sample has a significant background colour associated with it.

Note, in the experiments above, the clinical sample tested was milk obtained from a bovine animal suspected of being infected by mastitis. If a non-milk clinical sample were to be tested, then inclusion of a stabilizing agent (e.g. milk in the form of a liquid or powder) would be required in order to suppress the growth inhibitory effect of esculin and ferric citrate at the higher concentrations used according to this invention.

TABLE 6

Strep uberis in 100 uL esculin/ferric citrate/TSB media + 20 uL milk; inoculum refers to cfu/mL in milk

| | 10^6 cfu/ml | 10^4 cfu/ml |
| --- | --- | --- |
| 0.1% esculin + 0.05% ferric citrate | slightly grey | slightly grey |

TABLE 6-continued

*Strep uberis* in 100 uL esculin/ferric citrate/TSB media + 20 uL milk; inoculum refers to cfu/mL in milk

|  | 10^6 cfu/ml | 10^4 cfu/ml |
|---|---|---|
| 1% esculin + 0.5% ferric citrate | black | black |
| 2% esculin + 1% ferric citrate | black | black |
| 5% esculin + 2.5% ferric citrate | not black | not black |

Colour was checked after ~16 h and ~48 h.

Applicant further discovered that TSB containing 0.5% esculin and 0.25% ferric citrate and 80 uL of spiked *Streptococcus uberis* milk sample which also contained 100 ug/ml aztreonam concentration (antibiotic which has activity against many gram-bacteria such as *E. coli*) and/or in combination with 0.5 mg/mL phenol red led to easy detectable colour changes. No inhibition of *Streptococcus uberis* due to phenol red or aztreonam was detected.

Example 4: Staphylococci Identification (Differentiation and Selectivity) in Clinical Samples The differentiation of coagulase positive and coagulase negative Staphylococci is often desired. Knowing the type of coagulase Staphylococci can influence the treatment decision.

Traditionally, differentiation between coagulase positive and negative *staphylococci* has been performed with the tube coagulase test which detects extracellular staphylocoagulase or the slide coagulase test that detects the clumping factor (bound coagulase) present on the bacterial cell surface.

Alternatively, The BBL™ Staphyloslide™ Latex Test is a latex slide agglutination test for the differentiation of *staphylococci* which possess clumping factor and/or Protein A, usually present with *Staphylococcus aureus*, from *staphylococci* that do not possess these properties.

The BBL™ Staphyloslide™ Latex Test consists of blue latex particles coated with human fibrinogen and IgG. On mixing the latex reagent with colonies of *staphylococci* which have clumping factor or Protein A present, cross-linking will occur giving visible agglutination of the latex particles. Such agglutination will occur notably with *Staphylococcus aureus*. If neither clumping factor nor Protein A are present, no agglutination will occur and the result will be regarded as negative. The most frequent coagulase and Protein A negative isolates of *staphylococci* are *Staphylococcus epidermidis*.

These coagulase tests (slide, tube and latex particles) require culturing of samples on agar plates.

Mannitol Salt Broth (MSB; refer to an example in Example 1) is a selective medium for the isolation of presumptive pathogenic *staphylococci*. Most of the other bacteria are inhibited by the high concentration of Sodium chloride.

MSB comprises peptone which provide nitrogen, vitamins, minerals and amino acids essential for growth. MSB, as the name suggests, also comprises mannitol which is the carbohydrate energy source. Sodium chloride supplies essential electrolytes for transport and osmotic balance. The degradation of mannitol by bacteria produces acidification products that can be detected in the presence of a pH indicator. In the case of phenol red, production of acidification products causes a colour change from red to yellow.

This is demonstrated by the following growth inhibition assays performed at 35±2° C. over 18-24 hours and after 48 hours:

| Microorganism | Growth | Acid Production |
|---|---|---|
| *Escherichia coli* ATCC 25922 | Inhibited | |
| *Proteus vulgaris* ATCC 13315 | Inhibited | |
| *Staphylococcus aureus* ATCC 25923 | Good | + |
| *Staphylococcus epidermidis* ATCC 12228 | Good | Lightly +/− |

It is known that *Staphylococcus epidermidis* produce acid aerobically from glucose, fructose, maltose, sucrose, and glycerol, and 70 to 90% of the strains produce acid aerobically from galactose, mannose, and lactose. No acid is produced from mannitol, trehalose, rhamnose, xylose, or arabinose (Parisi (1985) *Microbiological Reviews* 49(2): 126-139).

It is also known that mannitol salt media can be used to selectively grow Staphylococci and can be used to differentiate between coagulase positive Staphylococci (*Staphylococcus aureus*) and coagulase negative Staphylococci (CNS) such as *Staphylococcus epidermidis*. The problem is in case of bovine mastitis that milk contains lactose (4-5% on average) and therefore CNS are able to produce acid in MSB as well which leads to yellow colour change. Thus differentiation between coagulase positive and negative Staphylococci fails with mannitol salt media for milk samples.

Alternatively, Baird Parker Agar (refer to Example 1 for an example formulation) is used for detection and enumeration of *Staphylococcus aureus* in foods. The selectivity of the medium is due to lithium chloride and 1% potassium tellurite, suppressing growth of organisms other than Staphylococci. The differentiation of coagulase-positive *staphylococci* is based on potassium tellurite and egg yolk emulsion. Staphylococci that contain lecithinase break down the egg yolk leading to the formation of clear zones around the colonies. An opaque zone of precipitation may form due to lipase activity. Reduction of potassium tellurite is a characteristic of coagulase-positive *staphylococci*, and causes blackening of colonies. Agar is the solidifying agent.

Baird Parker Agar contains ~1% tellurite in solution. Expected growth outcomes are as follows:

| Microorganism | ATCC | Growth | Characteristics |
|---|---|---|---|
| *Escherichia coli* | 25922 | inhibited | |
| *Bacillus subtilis* | 6633 | poor to fair | brown |
| *Proteus mirabilis* | 25933 | good | brown |
| *Staphylococcus aureus* | 25923 | good | black |
| *Staphylococcus epidermidis* | 14990 | poor to good | black |

These data demonstrates that differentiation of coagulase positive and negative Staphylococci is unreliable by using Baird Parker Agar.

Alternatively, Giolitti-Cantoni Broth Base is used for enriching *Staphylococcus aureus* from foods during isolation procedures. Lithium chloride inhibits gram-negative bacilli. Potassium tellurite in combination with glycine inhibits gram-positive bacteria other than *staphylococci*.

1.05 ml or 0.105 ml when testing meat products Tellurite solution of 1% is added to 19 ml of Giolitti Cantoni broth base (GC). Then typically 1 g or 1 ml of sample is added to 19 ml Giolitti Cantoni/Tellurite broth. Thus the tellurite solution concentration in GC is typically between 5% and 0.5%. Sample concentration is about 5% in Giolitti Cantoni broth.

| ORGANISM | ATCC ™ | INOCULUM CFU | RECOVERY | APPEARANCE |
|---|---|---|---|---|
| *Escherichia coli* | 25922 | $10^3$-$2 \times 10^3$ | Inhibition | No blackening |
| *Micrococcus luteus* | 10240 | $10^3$-$2 \times 10^3$ | Inhibition | No blackening |
| *Staphylococcus aureus* | 6538 | $10^2$-$10^3$ | Good | Black |
| *Staphylococcus aureus* | 25923 | $10^2$-$10^3$ | Good | Black |

Expected Results

Read tubes for blackening of the medium (a positive reaction) or no blackening (a negative reaction). If blackening occurs, subculture to Baird-Parker Agar to confirm the isolation of *S. aureus*.

There is no indication how *Staph epidermidis* behaves in Giolitti/Cantoni/Tellurite broth. It should be expected that this will not differ to Baird Parker broth since the recommendation is to subculture to Baird Parker Agar.

None of these above listed media for Staphylococci on its own gives a desired solution to receive a fast and easy differentiation of coagulase positive and negative Staphylococci (Staph *aureus* vs CNS).

1% potassium tellurite solution is usually added to Baird Parker media ~1%

Varies for Giolitti Cantoni between 0.5% and 5%.

Definitions for Staph Experiments:

black means black sediment accumulated at the bottom of a vial/well.

SA: Staph *aureus* (coagulase positive); SE: *Staph epidermidis* (coagulase negative)

1% tellurite Solution unless indicated

TABLE 7

81 µl Composition 5 + 20 µl Bacteria sample 5b, 5c, 5e, 5f, 5g or 5h or
20 µl Bacteria sample 7b, 7c, 7e, 7f, 7g or 7h or 20 µl Bacteria sample 8

| Inoculum cfu/ml | $10^7$ | $10^{6.5}$ | $10^6$ | $10^4$ | $10^3$ | $10^2$ | 0 (no bacteria) | $10^4$ (no tellurite) |
|---|---|---|---|---|---|---|---|---|
| | | | | t = 0 h | | | | |
| *Staph aureus* | white | white | white | white | white | white | white | white |
| *Staph epidermidis* | white | white | white | white | white | white | white | white |
| | | | | t~16 h | | | | |
| *Staph aureus* | black | black | black | black | black | black | white | white |
| *Staph epidermidis* | black | black | black | grey | grey | white | white | white |
| | | | | t~48 h | | | | |
| *Staph aureus* | black | black | black | black | black | black | white | white |
| *Staph epidermidis* | black | black | black | black | black | black | white | white |

TABLE 8

81 µl Composition 6 or 86 µl Composition 7 + 20 µl Bacteria
sample 5a, 5c, 5e or 5g or 20 µl Bacteria sample 7a, 7c, 7e or 7g

| Inoculum cfu/ml | $10^8$ Comp. 6 | $10^6$ Comp. 6 | $10^4$ Comp. 6 | $10^2$ Comp. 6 | $10^8$ Comp. 7 | $10^6$ Comp. 7 | $10^4$ Comp. 7 | $10^2$ Comp. 7 |
|---|---|---|---|---|---|---|---|---|
| | | | | t = 0 h | | | | |
| *Staph aureus* | white | white | white | white | white | white | white | white |
| *Staph epidermidis* | white | white | white | white | white | white | white | white |
| | | | | t~16 h | | | | |
| *Staph aureus* | black | black | black | black | black | black | black | black |
| *Staph epidermidis* | black | black | black | white | black | black | white | white |
| | | | | t~24 h | | | | |
| *Staph aureus* | black | black | black | black | black | black | black | black |
| *Staph epidermidis* | black | black | black | black | black | black | black | white |
| | | | | t~48 h | | | | |
| *Staph aureus* | black | black | black | black | black | black | black | black |
| *Staph epidermidis* | black | black | black | black | black | black | black | black |

The results from Table 7 demonstrates that coagulase positive and negative Staphylococci forms black sediments after incubation. This is not unexpected considering knowledge of the art.

The results from Table 8 shows effect of increasing Tellurite solution concentration (1% or 10%). Giolitti Cantoni (GC) broth and bacteria sample was mixed 50/50. Even 10% tellurite solution could not suppress blackening of the media from coagulase negative Staphylococci (SE).

Typically GC media is applied for food stuff and the application of this media to clinical samples to distinguish coagulase positive and negative is not obvious.

Despite the above knowledge it was surprisingly found that tellurite can be used to differentiate coagulase positive and negative Staphylococci.

Three media were identified which are able to differentiate of coagulase positive Staphylococci (*Staphylococcus aureus*) and coagulase negative Staphylococci (*Staphylococcus epidermidis*) if inoculum is not more than $10^7$ cfu/ml. An enrichment of *Staphylococcus aureus* was achieved and at the same time *Staphylococcus epidermidis* was suppressed:

1. Giolitti Cantoni+Tellurite solution+bacteria sample (80 ul+10 ul+20 ul)
2. Mannitol salt broth+Tellurite solution+bacteria sample (80 ul+1 ul+20 ul)
3. Tryptic Soy broth+excess amount of phenol red+3-6 ul Tellurite solution Enrichment of *Staph epidermidis* with colour change was achieved
4. Mannitol salt broth+bacteria milk sample (80 ul+20 ul), in principle any carbohydrate source such as lactose from which *Staph epidermidis* can produce acid Novel combinations (2 vials/wells)
1+4;
2+4;
3+4;

Specific Examples

Giolitti Cantoni Tellurite Broth

Surprisingly, it was found if Giolitti Cantoni broth, Tellurite solution and bacteria sample are mixed in parts 8:1:2 then differentiation of coagulase positive and negative Staph is possible (for inoculum of equal or less than $10^7$ cfu/ml in bacteria sample) (Table 9 and 10). Thus such or similar medium allows the identification of coagulase positive Staph (e.g. *Staph aureus*) and suppresses coagulase negative Staph (CNS). Clinical bacterial samples usually contain less than $10^8$ cfu/ml.

If blackening occurs then the amount of black sediment gradually increases with time and the starting time of noticeable black sediment depends on inoculum and together with a calibration (black sediment occurrence over time), an estimation of initial inoculum in clinical sample is possible.

TABLE 9

Staphylococci; Tellurite solution combined with GC; 80 ul media + 10 ul Tell Sol. + 20 ul Bacteria in milk

| Inoculum cfu/ml | $10^8$ | $10^7$ | $10^6$ | $10^4$ | $10^3$ | $10^2$ | 0 (no bacteria) |
|---|---|---|---|---|---|---|---|
| t = 0 h | | | | | | | |
| SA | white | white | white | white | white | white | white |
| SE | white | white | white | white | white | white | white |
| t~16 h | | | | | | | |
| SA | black | black | black | black | black | white | white |
| SE | black | white | white | white | white | white | white |
| t~24 h | | | | | | | |
| SA | black | black | black | black | black | white | white |
| SE | black | grey | white | white | white | white | white |

TABLE 10

Staphylococci; Tellurite solution combined with GC; 80 ul media + 10 ul Tell Sol. + 20 ul Bacteria in milk

| Inoculum cfu/ml | $10^7$ | $10^{6.5}$ | $10^6$ | $10^4$ | $10^3$ | $10^2$ | 0 (no bacteria) |
|---|---|---|---|---|---|---|---|
| t = 0 h | | | | | | | |
| SA | white | white | white | white | white | white | white |
| SE | white | white | white | white | white | white | white |
| t~16 h | | | | | | | |
| SA | black | black | black | black | black | grey | white |
| SE | white | white | white | white | white | white | white |
| t~48 h | | | | | | | |
| SA | black | black | black | black | black | black | white |
| SE | white | white | white | white | white | white | white |

Mannitol Salt/Tellurite Broth

TABLE 11

*Staphylococci*; Tellurite solution combined with MSB; 80 ul media + 6 ul Tell Sol. (0.1%) + 20 ul Bacteria in milk

| | $10^8$ | $10^7$ | $10^6$ | $10^4$ | $10^3$ | $10^2$ | 0 (no bacteria) |
|---|---|---|---|---|---|---|---|
| t = 0 h | | | | | | | |
| SA | pink | pink | pink | pink | pink | pink | pink |
| SE | pink | pink | pink | pink | pink | pink | pink |
| t~16 h | | | | | | | |
| SA | black/y | black/y | black/y | blacko | grey/p | pink | pink |
| SE | black/y | black/y | pink | pink | pink | pink | pink |
| t~24 h | | | | | | | |
| SA | black/y | black/y | black/y | black/y | black/o | black/p | pink |
| SE | black/y | black/y | grey/o | pink | pink | pink | pink |

TABLE 12

*Staphylococci*; Tellurite solution combined with MSB; 80 ul media + 1 ul Tell Sol. + 20 ul Bacteria in milk

| | $10^8$ | $10^6$ | $10^4$ | $10^3$ | $10^2$ | 0 (no bacteria) | no Tellurite $10^4$ |
|---|---|---|---|---|---|---|---|
| t = 0 h | | | | | | | |
| SA | pink | pink | pink | pink | pink | pink | pink |
| SE | pink | pink | pink | pink | pink | pink | pink |
| t~16 h | | | | | | | |
| SA | black/y | black/y | grey/o | pink | pink | pink | yellow |
| SE | black/y | pink | pink | pink | pink | pink | yellow |
| t~24 h | | | | | | | |
| SA | black/y | black/y | black/y | black/y | black/y | pink | yellow |
| SE | black/y | pink | pink | pink | pink | pink | yellow |

TABLE 13

*Staphylococci*; 1% Tellurite solution in MSB; 40 ul media + 40 ul H2O + 1 ul Tell Sol. + 20 ul Bacteria in milk

| | \multicolumn{6}{c}{Inoculum cfu/ml} | |
|---|---|---|---|---|---|---|---|
| | 10^8 | 10^6 | 10^4 | 10^3 | 10^2 | (no bacteria) | no Tellurite 10^4 |
| | | | | t = 0 h | | | |
| SA | pink | pink | pink | pink | pink | pink | pink |
| SE | pink | pink | pink | pink | pink | pink | pink |
| | | | | t~16 h | | | |
| SA | black/y | black/y | black/y | black/y | grey/p | pink | yellow |
| SE | black/y | pink | pink | pink | pink | pink | yellow |
| | | | | t~24 h | | | |
| SA | black/y | black/y | black/y | black/y | black/y | pink | yellow |
| SE | black/y | pink | pink | pink | pink | pink | yellow |

Black/y = black sediment with yellow media
Black/o = black sediment with orange media
Black/p = black sediment with pink media
Grey/o = grey sediment with orange media
Grey/y = grey sediment with yellow media

TABLE 14

*Staph epidermidis*; Mannitol salt broth +/− 1.25% Lactose

| | t = 0 h | | t~16 h | |
|---|---|---|---|---|
| Inoculum Cfu/ml | MSB | MSB + 1.25% Lactose | MSB | MSB + 1.25% Lactose |
| 10^6 | Pink | Pink | Pink | Yellow |

Surprisingly, it was found that even ~1 ul Tellurite in MSB or MSB/H2O mixture suppresses enrichment of *Staph epidermidis* if inoculum is between 10^8 and 10^6 cfu/ml or less over period of at least 24 h. If no Tellurite is present then *Staph epidermidis* enrichment occurs and thus colour change (lactose is present in milk) (control). *Staph aureus* enriched in presence of 1% tellurite solution and led to a black sediment. This is a novel way of identifying coagulase positive Staph.

Even 0.6 ul Tellurite solution delivers reasonable results but it is very much on borderline. ~1 ul Tellurite solution is preferred.

If milk, which contains lactose, or pure lactose or other carbohydrate sources, which enables *Staph epidermidis* to produce acid, are present then an enrichment with colour change occurs. This is desired in my case. Consequently, the claim should also include a well combination where well 1 contains at least MSB/Tellurite solution and bacteria sample and well 2 contains MSB/milk and/or lactose and/or other carbohydrate sources, which allows coagulase negative Staph producing acid, and bacteria sample. This well combination allows the identification of coagulase positive or negative of a clinical sample. An estimation of the initial inoculum is possible as well. Same principle as described in the GC section.

Tryptic Soy Broth/Phenol Red/Tellurite Broth

TABLE 15

*Staphylococci*; Tellurite solution combined with TSB/0.25 mg/ml phenol red; 80 ul media + 3 ul Tell Sol. + 20 ul Bacteria in milk

| | \multicolumn{7}{c}{Inoculum cfu/ml} |
|---|---|---|---|---|---|---|---|
| | 10^8 | 10^7 | 10^6 | 10^4 | 10^3 | 10^2 | 0 (no bacteria) |
| | | | | t = 0 h | | | |
| SA | red | red | red | red | red | red | red |
| SE | red | red | red | red | red | red | red |
| | | | | t~16 h | | | |
| SA | black/y | black/y | black/y | black/o | black/r | red | red |
| SE | black/o | grey/o | red | red | red | red | red |
| | | | | t~24 h | | | |
| SA | black/y | black/y | black/y | black/y | black/y | black/o | red |
| SE | black/y | black/y | red | red | red | red | red |

TABLE 16

*Staphylococci*; Tellurite solution combined with Tsb + 0.125 mg/ml phenol red; 80 ul media + 1 ul Tell Sol. + 20 ul Bacteria in milk

| | \multicolumn{7}{c}{Inoculum cfu/ml} | |
|---|---|---|---|---|---|---|---|
| | 10^8 | 10^6 | 10^4 | 10^3 | 10^2 | 0 (no bacteria) | no Tellurite 10^4 |
| | | | | t = 0 h | | | |
| SA | red | red | red | red | red | red | red |
| SE | red | red | red | red | red | red | red |
| | | | | t~16 h | | | |
| SA | black/y | black/y | black/o | red | red | red | yellow |
| SE | black/o | red | red | red | red | red | yellow |

TABLE 16-continued

Staphylococci; Tellurite solution combined with Tsb + 0.125 mg/ml phenol red; 80 ul media + 1 ul Tell Sol. + 20 ul Bacteria in milk

| | Inoculum cfu/ml | | | | | | |
|---|---|---|---|---|---|---|---|
| | $10^8$ | $10^6$ | $10^4$ | $10^3$ | $10^2$ | 0 (no bacteria) | no Tellurite $10^4$ |
| | | | | t~24 h | | | |
| SA | black/y | black/y | black/y | black/o red | black/r | red | yellow |
| SE | black/y | red | red | red | red | red | yellow |
| | | | | t~48 h | | | |
| SE | black/y | red | red | red | red | red | yellow |

TABLE 17

Staphylococci; Tellurite solution combined with TSB + 0.25 mg/ml phenol red; 80 ul media + 6 ul Tell Sol. + 20 ul Bacteria in milk

| | Inoculum cfu/ml | | | | | | |
|---|---|---|---|---|---|---|---|
| | $10^7$ | $10^{6.5}$ | $10^6$ | $10^4$ | $10^3$ | $10^2$ | 0 (no bacteria) | no Tellurite $10^4$ (control) |
| | | | | t = 0 h | | | | |
| SA | red | red | red | red | red | red | red | red |
| SE | red | red | red | red | red | red | red | red |
| | | | | t~16 h | | | | |
| SA | black/y | black/y | black/y | black/o red | black/r | red | red | yellow |
| SE | red | red | red | red | red | red | red | orange |
| | | | | t~48 h | | | | |
| SA | black/y | black/y | black/y | black/y | black/o | red | red | yellow |
| SE | red | red | red | red | red | red | red | white |

Surprisingly, it was found that the combination of TSB and excess amount of phenol red e.g. 0.125 mg/ml or more in combination with 3 ul or 6 ul Tellurite solution is able to suppress enrichment of Staph epidermidis (CNS) up to 48 h culture time but at the same time enriches Staph *aureus* which leads to a black sediment with colour change.
An estimation of the initial inoculum is possible as well.

Example 5: Bacteria Identification

Abbreviations for Tables 18 and 19:
GC10% T
  80 ul Giolitti Cantoni base broth+10 ul Tellurite solution+20 ul bacteria in milk
MSB
  80 ul Mannitol salt broth+20 ul bacteria in milk
TSB/Fer/FerCit
  80 ul Tryptic soy broth containing 0.25% Esculin and 0.125% Ammonium Ferric Citrate+20 ul bacteria in milk
McC/PR0.25 mg/ml
  80 ul MacConkey broth (single strength) containing 0.025% phenol red+20 ul bacteria in milk
TSB/PR0.25 mg/ml
  80 ul Tryptic soy broth containing 0.025% phenol red+20 ul bacteria in milk
TSB/PR0.125 mg/ml
  80 ul Tryptic soy broth containing 0.0125% phenol red+20 ul bacteria in milk
TSB/PR0.05 mg/ml
  80 ul Tryptic soy broth containing 0.005% phenol red+20 ul bacteria in milk
Black/w
  black sediment and white media
Black/y
  black sediment and yellow media
Greyp/p
  grey sediment and pink media Bacteria in milk was $10^4$ cfu/ml and $10^6$ cfu/ml. Table 18 and 19 shows the colour of each well at incubation t=0 hours and t=24 hours. GC10% T is the selective and differential media for coagulase positive Staphylococci (*Staphylococcus aureus*). Only *Staphylococcus aureus* at both bacteria concentrations showed black sediment. All other bacteria in GC10% T (*Staphylococcus epidermidis*, *Escherichia coli* and *Streptococcus uberis*) had no black sediment. MSB is the selective media for Staphylococci. Both *Staphylococcus aureus* and *Staphylococcus epidermidis* media had a colour change to yellow at t=24 hours. *E. Coli* and *Streptococcus uberis* media remained with a pink colour. The combination of GC10% T and MSB allows to distinguish between coagulase positive and negative *Staphylococcus* if one of the bacteria is present in the clinical sample. If GC10% T is white without black sediment but MSB is yellow then the clinical sample contains coagulase negative Staphylococci. If GC10% T has a black sediment and MSB is yellow then the clinical sample contains coagulase positive Staphylococci. TSB/Esc/FerCit is the selective media for Group D *Streptococci* to which *Streptococcus uberis* belong to. Only *Streptococcus uberis* turned this media black after 24 hours. All other investigated bacteria (*Staphylococcus aureus*, *Staphylococcus epidermidis*, *E. coli*) did not change the colour of the Group D *Streptococci* media at t=24 hours. McC/PR0.125 mg/ml is the selective media for coliform bacteria. Only *E. coli* changed the colour of the media at t=24 hours. All other investigated bacteria (*Staphylococcus aureus, Staphylococcus epidermidis, Streptococcus uberis*) did not change the colour of the coliform enrichment media at t=24 hours. The general enrichment media TSB/PR0.25 mg/ml, TSB/PR0.125 mg/ml and TSB/PF0.05 mg/ml changed colour at t=24 hours for all four investigated bacteria.

This combination of general, selective and differential media allows the identification of Group D bacteria *Streptococci*, coagulase positive and negative Staph and coliform bacteria as well as if any other bacteria (not identified).

80 ul MacConkey broth (single strength) containing 0.02% phenol red and 1% Cloxacillin as sodium+20 ul bacteria in milk
TSB/PR0.2 mg/ml

TABLE 18

80 μl Composition 2b, 2c, 2d, 8, 11 or 19 + 20 μl Bacteria sample 5c or 5e or 20 μl Bacteria sample 7c or 7e

|  | t = 0 h | | | | t = 24 h | | | |
|---|---|---|---|---|---|---|---|---|
|  | \multicolumn{8}{c}{Inoculum/cfu/ml} |
|  | $10^4$ | | $10^6$ | | $10^4$ | | $10^6$ | |
|  | 5e (SA) | 7e (SE) | 5c (SA) | 7e (SE) | 5e (SA) | 7e (SE) | 5c (SA) | 7e (SE) |
| Composition 8 | white | White | white | white | black/w | white | black/w | white |
| Composition 11 | Pink | Pink | Pink | Pink | yellow | yellow | yellow | yellow |
| Composition 18 | White | White | White | White | White | White | White | White |
| Composition 19 | red | Red | red | red | red | red | red | red |
| Composition 2d | red | Red | red | red | yellow | yellow | yellow | yellow |
| Composition 2c | — | — | red | red | — | — | yellow | yellow |
| Composition 2b | — | — | red | red | — | — | yellow | yellow |

TABLE 19

80 μl Composition 2b, 2c, 2d, 8, 11 or 19 + 20 μl Bacteria sample 4c or 4e or 20 μl Bacteria sample 6c or 6e

|  | t = 0 h | | | | t = 24 h | | | |
|---|---|---|---|---|---|---|---|---|
|  | \multicolumn{8}{c}{Inoculum/cfu/ml} |
|  | $10^4$ | | $10^6$ | | $10^4$ | | $10^6$ | |
|  | 6e (SU) | 4e (EC) | 6c (SU) | 4c (EC) | 6e (SU) | 4e (EC) | 6c (SU) | 4c (EC) |
| Composition 8 | white | white | white | white | white | white | white | white |
| Composition 11 | Pink | Pink | Pink | Pink | pink | pink | pink | pink |
| Composition 18 | White | White | White | White | black | white | black | white |
| Composition 19 | red | red | red | red | red | yellow | red | yellow |
| Composition 2d | red | red | red | red | yellow | yellow | yellow | yellow |
| Composition 2c | — | — | red | red | — | — | yellow | yellow |
| Composition 2b | — | — | red | red | — | — | yellow | yellow |

Abbreviations for Table 20:
GC5.25% T 80 ul Giolitti Cantoni base broth+5.25 ul Tellurite solution+20 ul bacteria in milk
MSB2-0.5% T 60 ul MSB+5.25 ul Tellurite (0.1%)+5 ul LiCl+1.2 ul Glycine+8.55 ul H2O+20 ul bacteria in milk
TSB/Fer/FerCit2

80 ul Tryptic soy broth containing 0.5% Esculin and 0.25% Ammonium Ferric Citrate+20 ul bacteria in milk
McCCLXPR0.2 mg/ml 80 ul Tryptic soy broth containing 0.02% phenol red+20 ul bacteria in milk Incubation of *Streptococci agalactiae* (Group B *Streptococci*) does not change the colour of the investigated selective or differential enrichment media (GC5.25% T, MSB2-0.5% T, TSB/Esc/FerCit2/McCCLXPR0.2 mg/ml) after 24 hours of incubation. Only the general enrichment medium (TSB/PR0.2 mg/ml) turned yellow after 24 hours incubation.

TABLE 20

80 μl Composition 20, 21, 22, 23 or 24 + 20 μl Bacteria sample 6c or 20 μl Bacteria sample 9a or 9b

| | t = 0 h | | | t~16 h | | |
|---|---|---|---|---|---|---|
| | | | Inoculum/cfu/ml | | | |
| | 10^3 | | 10^6 | 10^3 | | 10^6 |
| | 9a (SAg) | — | 9b (SAg) | 6c (SU) | 9a (SAg) | — | 9b (SAg) | 6c (SU) |
| Composition 20 | white | — | white | white | white | — | white | white |
| Composition 21 | Pink | — | Pink | Pink | pink | — | pink | pink |
| Composition 22 | white | — | white | white | White | — | White | black |
| Composition 23 | red | — | red | red | red | — | red | red |
| Composition 24 | red | — | red | red | yellow | — | yellow | yellow |

Example 6: Combined Bacteria Identification and Antimicrobial Susceptibility Testing Clinical bovine mastitis milk samples were collected by a vet clinic in South Island, New Zealand. Samples were stored in the freezer for several months and shipped frozen to the testing facility. In this Example, the term "clinical" means that dairy cows had clinical symptoms of an udder infection e.g. cow behaved unusual, milk clots, swollen udder among other typical symptoms. Testing was executed in microwell plate comprising of 24 wells (3×8 wells).

1. Plate Configuration #1

Liquid volume of enrichment media for each well is listed in Table 21. In addition, 20 ul of clinical mastitis sample was added to each well with a laboratory pipette.

TABLE 21

Plate configuration #1; Drugs: Benzylpenicillin as potassium; Cloxacillin as sodium; Ceftiofur as hydrochloride; Drug concentration in each well (A3 to C8) is based on 80 μl composition + 10 μl drug solution + 20 μl clinical mastitis milk sample and equivalent to listed drug concentration in μg/ml; 20 ul of clinical bovine mastitis milk sample was added to each well (A1 to C8).

| well | A | B | C | Drug concentration |
|---|---|---|---|---|
| 1 | 86 μl Composition 8 | 80 μl Composition 18 | 80 μl Composition 2c | μg/ml (free from) |
| 2 | 80 μl Composition 11 | 90 μl Composition 25 | 80 μl Composition 1 | |
| 3 | 80 μl Composition 2c + 10 μl drug solution | 80 μl Composition 2c + 10 μl drug solution | 80 μl Composition 2c + 10 μl drug solution | 4 μg/ml (wells: A3-C3) |
| 4 | 80 μl Composition 2c + 10 μl drug solution | 80 μl Composition 2c + 10 μl drug solution | 80 μl Composition 2c + 10 μl drug solution | 2 μg/ml (wells: A4-C4) |
| 5 | 80 μl Composition 2c + 10 μl drug solution | 80 μl Composition 2c + 10 μl drug solution | 80 μl Composition 2c + 10 μl drug solution | 1 μg/ml (wells: A5-C5) |
| 6 | 80 μl Composition 2c + 10 μl drug solution | 80 μl Composition 2c + 10 μl drug solution | 80 μl Composition 2c + 10 μl drug solution | 0.5 μg/ml (wells: A6-C6) |
| 7 | 80 μl Composition 2c + 10 μl drug solution | 80 μl Composition 2c + 10 μl drug solution | 80 μl Composition 2c + 10 μl drug solution | 0.1 μg/ml (wells: A7-C7) |
| 8 | 80 μl Composition 2c + 10 μl drug solution | 80 μl Composition 2c + 10 μl drug solution | 80 μl Composition 2c + 10 μl drug solution | 0.05 μg/ml (wells: A8-C8) |
| | Benzylpenicillin | Ceftiofur | Cloxacillin | |

TABLE 22

Colour of media in each well prior incubation at 0 hours (Table 21, Plate configuration #1) for clinical bovine mastitis sample identification numbers (ID) 1, 2, 3 and 4

| ID | T = 0 h | | |
|---|---|---|---|
| 1 to 4 | A | B | C |
| 1 | white | white | red |
| 2 | pink | white | red |
| 3 | red | red | red |
| 4 | red | red | red |
| 5 | red | red | red |
| 6 | red | red | red |
| 7 | red | red | red |
| 8 | red | red | red |

TABLE 24

Colour of media in each well after 22 hours incubation at 37° C. (Table 21, Plate configuration #1) for clinical bovine mastitis sample identification number: ID 2
T = 22 h

| ID 2 | A | B | C |
|---|---|---|---|
| 1 | white | black | yellow |
| 2 | pink | white | red |
| 3 | orange | red | red |
| 4 | orange | red | red |
| 5 | orange | red | red |
| 6 | yellow | orange | red |
| 7 | yellow | yellow | yellow |
| 8 | yellow | yellow | yellow |

TABLE 23

Colour of media in each well after 22 hours incubation at 37° C. (Table 21, Plate configuration #1) for clinical bovine mastitis sample identification number: ID 1
T = 22 h

| ID 1 | A | B | C |
|---|---|---|---|
| 1 | white | black | yellow |
| 2 | pink | black | red |
| 3 | red | red | red |
| 4 | red | red | red |
| 5 | red | red | red |
| 6 | red | red | red |
| 7 | red | yellow | yellow |
| 8 | orange | yellow | yellow |

TABLE 25

Colour of media in each well after 48 hours incubation at 37° C. (Table 21, Plate configuration #1) for clinical bovine mastitis sample identification number: ID 2
T = 48 h

| ID 2 | A | B | C |
|---|---|---|---|
| 1 | black/w | black | yellow |
| 2 | yellow | white | red |
| 3 | yellow | red | red |
| 4 | yellow | red | red |
| 5 | yellow | red | red |
| 6 | yellow | yellow | red |
| 7 | yellow | yellow | yellow |
| 8 | yellow | yellow | yellow |

TABLE 26

Colour of media in each well after 22 hours incubation at 37° C. (Table 21, Plate configuration #1) for clinical bovine mastitis sample identification number: ID 3
T = 22 h

| ID 3 | A | B | C |
|---|---|---|---|
| 1 | white | white | yellow |
| 2 | pink | white | yellow |
| 3 | yellow | red | yellow |
| 4 | yellow | red | yellow |
| 5 | yellow | red | red |
| 6 | yellow | yellow | red |
| 7 | yellow | yellow | yellow |
| 8 | yellow | red | yellow |

TABLE 27

Colour of media in each well after 22 hours incubation at 37° C. (Table 21, Plate configuration #1) for clinical bovine mastitis sample identification number: ID 4
T = 22 h

| ID 4 | A | B | C |
|---|---|---|---|
| 1 | black/w | white | yellow |
| 2 | yellow | white | red |
| 3 | yellow | red | red |
| 4 | orange | red | red |
| 5 | orange | red | red |
| 6 | yellow | orange | red |
| 7 | yellow | yellow | yellow |
| 8 | yellow | yellow | yellow |

Abbreviations
1. 80 ul GC+10 ul Tell: 80 ul Giolitti Cantoni base broth+10 ul Tellurite solution (1%);
2. 80 ul TSB/Esc/Fer Cit: 80 ul Tryptic soy broth containing 0.25% Esculin and 0.125% Ammonium Ferric Citrate;
3. 80 ul TSB/Esc/Fer Cit+10 ul Genta: 80 ul Tryptic soy broth containing 0.25% Esculin and 0.125% Ammonium Ferric Citrate+10 ul of Gentamycin solution 10 mg/ml;
4. 80 ul McC/PR25: 80 ul MacConkey broth (single strength) containing 0.0125% phenol red; and
5. 80 ul TSB/PR25: 80 ul Tryptic soy broth containing 0.0125% phenol red.

Bacteria Identification

Columns A to C and rows 1 and 2 were used for bacteria identification. A1: coagulase positive Staph; A2: Staphylococci; B1: Strep group D; B2: Strep group D; C1: general enrichment media (gram+ and gram-bacteria); C2: coliform bacteria.

Antimicrobial Susceptibility Test

Column A3 to A8: serial dilution of benzyl penicillin as potassium. Column B3 to B8: serial dilution of ceftiofur as hydrochloride. Column C3 to C8: serial dilution of cloxacillin as sodium. Antibiotic concentrations are listed as free form ranging between 4 ug/ml to 0.05 ug/ml.

Minimum inhibitory substance concentration (MIC) is here defined as the concentration if a colour change occurs between two wells (one well remains red with drug concentration 1, the other one yellow with drug concentration 2, whereas drug concentration 1 is larger than drug concentration 2) then the MIC is the value of drug concentration 1.

Table 21 indicates the microwell plate configuration #1; Drugs: Benzylpenicillin as potassium; Cloxacillin as sodium; Ceftiofur as hydrochloride; Drug concentration in each well (A3 to C8) is based on 80 μl composition+10 μl drug solution+20 μl clinical mastitis milk sample and equivalent to listed drug concentration in µg/ml; 20 ul of clinical bovine mastitis milk sample was added to each well (A1 to C8).

Table 22 indicates the colour of the enrichment media in each well after the addition of the clinical mastitis sample into each well prior incubation (t=0 hours) for sample IDs 1,2,3,4 (reference).

Table 23 shows the colours of each enrichment medium for sample ID 1 after incubation at 37° C. for 22 hours. Enrichment medium in well B1 and B2 turned black and C1 turned yellow. No colour change in well A1, A2, C2. Thus this clinical sample contains *streptococci* group D. Antimicrobial susceptibility testing shows the MIC for benzyl penicillin 0.1 ug/ml, ceftiofur and cloxacillin 0.5 ug/ml.

Table 24 shows the colours of each enrichment medium for sample ID 2 after incubation at 37° C. for 22 hours. Enrichment medium in well B1 turned black and C1 turned yellow. No colour change in well A1, A2, B2, C2. Thus this clinical sample contains *streptococci* group D. Antimicrobial susceptibility testing shows the MIC for benzyl penicillin >4 ug/ml, ceftiofur 1 ug/ml and cloxacillin 0.5 ug/ml.

Table 25 shows the colours of each enrichment medium for sample ID 2 after incubation at 37° C. for 48 hours. Well B2 remained black and well A1 had a black sediment and A2 turned yellow. Thus this sample has also coagulase positive Staph. There is a chance that this Staphylococci is a beta-lactamase producing Staphylococci since benzyl penicillin is not susceptible at drug concentrations at least up to 4 ug/ml.

Table 26 shows the colours of each enrichment medium for sample ID 3 after incubation at 37° C. for 22 hours. Enrichment medium in well C1 and C2 turned yellow. No colour change in well A1, A2, B1 B2. Thus this clinical sample contains coliform bacteria. Antimicrobial susceptibility testing shows the MIC for benzyl penicillin and cloxacillin >4 ug/ml and ceftiofur 1 ug/ml.

Table 27 shows the colours of each enrichment medium for sample ID 4 after incubation at 37° C. for 22 hours. Enrichment medium in well A1 had a black sediment and A2, C1 turned yellow. No colour change in well B1, B2, C2. Thus this clinical sample contains coagulase positive Staph. Antimicrobial susceptibility testing shows the MIC for benzyl penicillin >4 ug/ml, ceftiofur 1 ug/ml and cloxacillin 0.5 ug/ml. There is a chance that this Staphylococci is a beta-lactamase producing Staphylococci since benzyl penicillin is not susceptible at drug concentrations at least up to 4 ug/ml.

2. Plate Configuration #2

Liquid volume of enrichment media of each well is listed in Table 28. In addition, each well received one drop of clinical sample from a transfer pipette which was on average about 35 mg. This was determined through weighing the well plate prior and after the addition of clinical mastitis samples. This weight was then divided by 24.

Abbreviations 1. 80 ul GC+10 ul Tell: 80 ul Giolitti Cantoni base broth+10 ul Tellurite solution (1%);
2. 80 ul TSB/Esc/Fer Cit: 80 ul Tryptic soy broth containing 0.25% Esculin and 0.125% Ammonium Ferric Citrate;
3. 80 ul TSB/Esc/Fer Cit+10 ul Genta: 80 ul Tryptic soy broth containing 0.25% Esculin and 0.125% Ammonium Ferric Citrate+10 ul of Gentamycin solution 10 mg/ml;
4. 80 ul McC/PR25: 80 ul MacConkey broth (single strength) containing 0.0125% phenol red; and
5. 80 ul TSB/PR25: 80 ul Tryptic soy broth containing 0.0125% phenol red.

TABLE 28

Plate configuration #2; Drugs: Benzylpenicillin as potassium; Cloxacillin as sodium; Ceftiofur as hydrochloride; Drug concentration in each well (A3 to C8) is based on 80 µl composition + 10 µl drug solution + 20 µl clinical mastitis milk sample and equivalent to listed drug concentration in µg/ml; 20 ul of clinical bovine mastitis milk sample was added to each well (A1 to C8).

| well | A | B | C | Drug concentration |
|---|---|---|---|---|
| 1 | 110 µl Composition 8 | 100 µl Composition 18 | 100 µl Composition 2c | µg/ml (free from) |
| 2 | 100 µl Composition 11 + 10 µl drug solution | | 100 µl Composition 1 | |
| 3 | 80 µl Composition 2c + 10 µl drug solution | 80 µl Composition 2c + 10 µl drug solution | 80 µl Composition 2c + 10 µl drug solution | 4 µg/ml (wells: A3-C3) |
| 4 | 80 µl Composition 2c + 10 µl drug solution | 80 µl Composition 2c + 10 µl drug solution | 80 µl Composition 2c + 10 µl drug solution | 2 µg/ml (wells: A4-C4) |
| 5 | 80 µl Composition 2c + 10 µl drug solution | 80 µl Composition 2c + 10 µl drug solution | 80 µl Composition 2c + 10 µl drug solution | 1 µg/ml (wells: A5-C5) |
| 6 | 80 µl Composition 2c + 10 µl drug solution | 80 µl Composition 2c + 10 µl drug solution | 80 µl Composition 2c + 10 µl drug solution | 0.5 µg/ml (wells: A6-C6) |
| 7 | 80 µl Composition 2c + 10 µl drug solution | 80 µl Composition 2c + 10 µl drug solution | 80 µl Composition 2c + 10 µl drug solution | 0.1 µg/ml (wells: A7-C7) |
| 8 | 80 µl Composition 2c + 10 µl drug solution Benzylpenicillin | 80 µl Composition 2c + 10 µl drug solution Ceftiofur | 80 µl Composition 2c + 10 µl drug solution Cloxacillin | 0.05 µg/ml (wells: A8-C8) |

TABLE 29

Colour of media in each well prior incubation at 0 hours (Table 28, Plate configuration #2) for clinical bovine mastitis sample identification numbers (ID) 5, 6, 7 and 8

T = 0 h

| ID 5 to 8 | A | B | C |
|---|---|---|---|
| 1 | white | white | red |
| 2 | pink | — | red |
| 3 | red | red | red |
| 4 | red | red | red |
| 5 | red | red | red |
| 6 | red | red | red |
| 7 | red | red | red |
| 8 | red | red | red |

TABLE 30

Colour of media in each well after 23 hours incubation at 37° C. (Table 28, Plate configuration #2) for clinical bovine mastitis sample identification number: ID 5
T = 23 h

| ID 5 | A | B | C |
|---|---|---|---|
| 1 | white | black | yellow |
| 2 | pink | — | red |
| 3 | red | red | red |
| 4 | red | red | red |
| 5 | red | red | red |
| 6 | red | red | red |
| 7 | red | yellow | yellow |
| 8 | red | yellow | yellow |

TABLE 31

Colour of media in each well after 23 hours incubation at 37° C. (Table 28, Plate configuration #2) for clinical bovine mastitis sample identification number: ID 6
T = 23h

| ID 6 | A | B | C |
|---|---|---|---|
| 1 | white | white | yellow |
| 2 | pink | — | yellow |
| 3 | yellow | red | yellow |
| 4 | yellow | red | yellow |
| 5 | yellow | yellow | yellow |
| 6 | yellow | yellow | yellow |
| 7 | yellow | yellow | yellow |
| 8 | yellow | yellow | yellow |

TABLE 32

Colour of media in each well after 23 hours incubation at 37° C. (Table 28, Plate configuration #2) for clinical bovine mastitis sample identification number: ID 7
T = 23h

| ID 7 | A | B | C |
|---|---|---|---|
| 1 | black/w | white | yellow |
| 2 | yellow | — | red |
| 3 | red | red | red |
| 4 | red | red | red |
| 5 | red | red | red |
| 6 | red | yellow | red |
| 7 | yellow | yellow | yellow |
| 8 | yellow | yellow | yellow |

TABLE 33

Colour of media in each well after 23 hours incubation at 37° C. (Table 28, Plate configuration #2) for clinical bovine mastitis sample identification number: ID 8
T = 23 h

| ID 8 | A | B | C |
|---|---|---|---|
| 1 | white | black | yellow |
| 2 | yellow | — | red |
| 3 | red | red | red |
| 4 | red | red | red |
| 5 | red | red | red |
| 6 | red | red | red |
| 7 | red | yellow | yellow |
| 8 | red | yellow | yellow |

TABLE 34

Colour of media in each well after 7, 11 and 23 hours incubation at 37° C. (Table 28, Plate configuration #2) for clinical bovine mastitis sample identification number: ID 3

T~7 h

| ID 3 | A | B | C |
|---|---|---|---|
| 1 | white | white | yellow |
| 2 | pink | white | red |
| 3 | red | red | red |
| 4 | red | red | red |
| 5 | red | red | red |
| 6 | red | red | red |
| 7 | red | red | red |
| 8 | red | red | red |

T = 23 h

| ID 3 | A | B | C |
|---|---|---|---|
| 1 | white | white | yellow |
| 2 | pink | white | yellow |
| 3 | yellow | red | yellow |
| 4 | yellow | red | yellow |
| 5 | yellow | red | red |
| 6 | yellow | yellow | red |
| 7 | yellow | yellow | yellow |
| 8 | yellow | red | yellow |

T~11 h

| ID 3 | A | B | C |
|---|---|---|---|
| 1 | white | white | yellow |
| 2 | pink | white | red |
| 3 | red | red | red |
| 4 | red | red | red |
| 5 | red | red | red |
| 6 | red | red | red |
| 7 | red | red | red |
| 8 | red | red | red |

TABLE 35

Colour of media in each well after 7, 11 and 23 hours incubation at 37° C. (Table 28, Plate configuration #2) for clinical bovine mastitis sample identification number: ID 6

T~7 h

| ID 6 | A | B | C |
|---|---|---|---|
| 1 | white | white | yellow |
| 2 | pink | — | yellow |
| 3 | yellow | red | yellow |
| 4 | yellow | red | yellow |
| 5 | yellow | red | yellow |
| 6 | yellow | yellow | yellow |
| 7 | yellow | yellow | yellow |
| 8 | yellow | yellow | yellow |

TABLE 35-continued

Colour of media in each well after 7, 11 and 23 hours incubation at 37° C. (Table 28, Plate configuration #2) for clinical bovine mastitis sample identification number: ID 6

T~11 h

| ID 6 | A | B | C |
|---|---|---|---|
| 1 | white | white | yellow |
| 2 | pink | — | yellow |
| 3 | yellow | red | yellow |
| 4 | yellow | red | yellow |
| 5 | yellow | red | yellow |
| 6 | yellow | yellow | yellow |
| 7 | yellow | yellow | yellow |
| 8 | yellow | yellow | yellow |

T~23 h

| ID 6 | A | B | C |
|---|---|---|---|
| 1 | white | white | yellow |
| 2 | pink | — | yellow |
| 3 | yellow | red | yellow |
| 4 | yellow | red | yellow |
| 5 | yellow | yellow | yellow |
| 6 | yellow | yellow | yellow |
| 7 | yellow | yellow | yellow |
| 8 | yellow | yellow | yellow |

Bacteria Identification

Columns A to C and rows 1 and 2 were used for bacteria identification. A1: coagulase positive Staph; A2: Staphylococci; B1: Strep Group D; B2: -; C1: general enrichment media (gram+ and gram-); C2: coliform bacteria.

Antimicrobial Susceptibility Test

Column A3 to A8: serial dilution of benzyl penicillin as potassium. Drug concentrations given as free form ranging between 4 ug/ml to 0.05 ug/ml. Column B3 to B8: serial dilution of ceftiofur as hydrochloride. Drug concentrations given as free form ranging between 4 ug/ml to 0.05 ug/ml. Column C3 to C8: serial dilution of cloxacillin as sodium. Drug concentrations given as free form ranging between 4 ug/ml to 0.05 ug/ml.

Table 29 indicates the colour of the enrichment media in each well after the addition of the clinical mastitis sample into each well prior incubation (t=0 hours) for sample IDs 5,6,7,8 (reference). Table 30 shows the colours of each enrichment medium for sample ID 5 after incubation at 37° C. for 23 hours. Enrichment medium in well B1 turned black and C1 turned yellow. No colour change in well A1, A2, C2. Thus this clinical sample contains *streptococci* group D. Antimicrobial susceptibility testing shows the MIC for benzyl penicillin <0.05 ug/ml, ceftiofur and cloxacillin 0.5 ug/ml.

Table 31 shows the colours of each enrichment medium for sample ID 6 after incubation at 37° C. for 23 hours. Enrichment medium in well C1 and C2 turned yellow. No colour change in well A1, A2, B1. Thus this clinical sample contains coliform bacteria. Antimicrobial susceptibility testing shows the MIC for benzyl penicillin and Cloxacillin >4 ug/ml and ceftiofur 2 ug/ml.

Table 32 shows the colours of each enrichment medium for sample ID 7 after incubation at 37° C. for 23 hours. Enrichment medium in well A1 had black sediment and A2, C1 turned yellow. No colour change in well B1, C2. Thus this clinical sample contains coagulase positive Staph. Antimicrobial susceptibility testing shows the MIC for benzyl penicillin and Cloxacillin 0.5 ug/ml and ceftiofur 1 ug/ml.

Table 33 shows the colours of each enrichment medium for sample ID 8 after incubation at 37° C. for 23 hours. Enrichment medium in well B1 turned black and A2, C1 turned yellow. No colour change in well A1, C2. Thus this clinical sample contains coagulase neative Staph and *Streptococci* group D bacteria. Antimicrobial susceptibility testing shows the MIC for benzyl penicillin <0.05 ug/ml, ceftiofur and cloxacillin 0.5 ug/ml.

Table 34 and 35 shows the change of colour of each enrichment media after incubation at 37° C. for the time point t=7 hours, t=11 hours and t=22-23 hours for clinical sample ID 3 and 6. Both samples contain coliform bacteria. Reference colour of each well in given in table 22 and 29.

Table 34 shows for sample ID 3 that after 7 hours and 11 hours of incubation no colour change in any of the enrichment media occurs compared to the reference (t=0 hours). At 22 hours of incubation colour change occurred in enrichment media (see also table 26 and its description).

Table 35 shows for sample ID 6 that colour change of enrichment media occurs at 7 hours and then remains unchanged at 11 hours and 23 hours compared to 7 hours. Comparing colour change in table 34 and 35 indicates that sample ID 6 had a high inoculum and sample ID 3 a low inoculum. A serial examination of the colour in wells e.g. hourly or every 15 min would then allow to determine the starting point of colour change. A calibration curve of e.g. *E. coli* showing colour in enrichment media over time would then allow to estimate the inoculum of a clinical *E. coli* sample. This will be the same as for any other gram positive or gram negative bacteria.

Tables 36 to 38 which follow show further examples of antibiotic susceptibility testing performed in accordance with the present invention. Table 36, antibiotic susceptibility testing of *Staphylococcus aureus* in Mueller Hinton and Tryptic Soy Broth at pre-incubation and at between 15-24 h. Tables 37 and 38, antimicrobial susceptibility testing of *Streptococcus uberis* and *E. coli* with the addition of gram negative specific antibiotic aztreonam. Tables 38 to 49 show further examples of antibiotic susceptibility testing and the outcomes are aligned with the described inventions.

TABLES 36(1) and (2)

Antibiotic susceptibility testing; A1 to D10: 70 ul composition 26 + 10 ul drug solution + 20 ul bacteria sample 5c; E1 to G10: 70 ul composition 2c + 10 ul drug solution + 20 ul bacteria sample 5c; H1 to H10: 20 composition 2c + 10 ul drug solution + 20 ul bacteria sample 5c

| | | | Drug Conc. (free form) per well µg/ml | | | | | | | | | |
|---|---|---|---|---|---|---|---|---|---|---|---|---|
| Antibiotic | Broth | well | 500 1 | 100 2 | 50 3 | 10 4 | 5 5 | 1 6 | 0.5 7 | 0.1 8 | 0.05 9 | 0.01 10 |
| 1. T = 0 hours (pre incubation) | | | | | | | | | | | | |
| Benzyl penicillin | Mueller Hinton | A | red | red | red | red | red | red | red | red | red | red |
| Oxytetracycline | Mueller Hinton | B | red | red | red | red | red | red | red | red | red | red |
| Cephalexin | Mueller Hinton | C | red | red | red | red | red | red | red | red | red | red |
| Neomycin | Mueller Hinton | D | red | red | red | red | red | red | red | red | red | red |

TABLES 36(1) and (2)-continued

Antibiotic susceptibility testing; A1 to D10: 70 ul composition 26 + 10 ul drug solution + 20 ul bacteria sample 5c; E1 to G10: 70 ul composition 2c + 10 ul drug solution + 20 ul bacteria sample 5c; H1 to H10: 20 ul composition 2c + 10 ul drug solution + 20 ul bacteria sample 5c

| | | | Drug Conc. (free form) per well µg/ml | | | | | | | | | |
|---|---|---|---|---|---|---|---|---|---|---|---|---|
| | | | 500 | 100 | 50 | 10 | 5 | 1 | 0.5 | 0.1 | 0.05 | 0.01 |
| Antibiotic | Broth | well | 1 | 2 | 3 | 4 | 5 | 6 | 7 | 8 | 9 | 10 |
| Dihydrostreptomycin | Tryptic Soy | E | red | red | red | red | red | red | red | red | red | red |
| Aztreonam | Tryptic Soy | F | red | red | red | red | red | red | red | red | red | red |
| Benzyl penicillin | Tryptic Soy | G | red | red | red | red | red | red | red | red | red | red |
| Benzyl penicillin | Tryptic Soy | H | red | red | red | red | red | red | red | red | red | red |
| 2. T = 15-24 h (following incubation at 35° C.; note: change in colour between 15 and 24 hours) | | | | | | | | | | | | |
| Benzyl penicillin | Mueller Hinton | A | red | red | red | red | red | red | red | red | red | red |
| Oxytetracycline | Mueller Hinton | B | red | red | red | red | red | red | red | yellow | yellow | yellow |
| Cephalexin | Mueller Hinton | C | red | red | red | red | red | red | yellow | yellow | yellow | yellow |
| Neomycin | Mueller Hinton | D | red | red | red | red | red | yellow | yellow | yellow | yellow | yellow |
| Dihydrostreptomycin | Tryptic Soy | E | red | red | yellow | yellow | yellow | yellow | yellow | yellow | yellow | yellow |
| Aztreonam | Tryptic Soy | F | yellow | yellow | yellow | yellow | yellow | yellow | yellow | yellow | yellow | yellow |
| Benzyl penicillin | Tryptic Soy | G | red | red | red | red | red | red | red | red | red | yellow |
| Benzyl penicillin | Tryptic Soy | H | red | red | red | red | red | red | red | red | red | red |

TABLE 37

*Streptococcus uberis* in presence of Aztreonam, total liquid volume varied between 5 µl to 220 µl; Drug solution: 100 µg Aztreonam per ml water.

| Bacteria sample 6d/µl | 160 | 80 | 40 | 20 | 8 | 4 |
|---|---|---|---|---|---|---|
| Composition 27/µl | 40 | 20 | 10 | 5 | 2 | 1 |
| Drug solution/µl | 20 | 10 | 5 | 2.5 | 1 | 0.5 |
| Colour of media prior incubation | Red | Red | Red | Red | Red | Red |
| Colour of media after 24 hours incubation at 37° C. | Black | Black | Black | Black | Black | Black |

TABLE 38

*Escherichia coli* in presence of Aztreonam, total liquid volume varied between 5 µl to 220 µl; Drug solution: 100 µg Aztreonam per ml water.

| Bacteria sample 4d/µl | 160 | 80 | 40 | 20 | 8 | 4 |
|---|---|---|---|---|---|---|
| Composition 27/µl | 40 | 20 | 10 | 5 | 2 | 1 |
| Drug solution/µl | 20 | 10 | 5 | 2.5 | 1 | 0.5 |
| Colour of media prior incubation | Red | Red | Red | Red | Red | Red |
| Colour of media after 24 hours incubation at 37° C. | Red | Red | Red | Red | Red | Red |

TABLE 40

Colour of media in each well after 0 hours incubation at 37° C. (Table 39, plate configuration #3), for bacteria samples 4c, 4e, 5c, 5e, 6d
T~0 h

| | A | B | C |
|---|---|---|---|
| 1 | red | Red | red |
| 2 | red | Red | red |
| 3 | red | Red | red |
| 4 | red | Red | red |
| 5 | red | Red | red |
| 6 | red | Red | red |

TABLE 43

Colour of media in each well after ~16 hours incubation at 37° C. (Table 39, plate configuration #3), for bacteria samples 5c
T~16 h

| | A | B | C |
|---|---|---|---|
| 1 | yellow | red | red |
| 2 | yellow | red | red |
| 3 | yellow | red | red |

TABLE 39

Plate configuration #3; Drugs: Benzylpenicillin as potassium; Cloxacillin as sodium; Aztreonam as free form; Drug concentration in each well (A1 to C6) is based on 20 µl composition + 80 µl clinical mastitis milk sample collected in sampling device. Sampling device cavities A, B or C 1 to 6, 10 µl of drug solution was added into each cavity and then dried for 30 min at 75° C. 80 µl of bacteria sample was then added to each cavity; Domed cavity dimensions: ~4.5 mm, cavity height ~5 mm.

| well | A | B | C | Aztreonam concentration/ (free form) µg/ml | Benzyl Penicillin or Cloxacillin concentration (free form)/µg/ml |
|---|---|---|---|---|---|
| 1 | 20 µl Composition 2e | 20 µl Composition 2e | 20 µl Composition 2e | 10 | 10,000 |
| 2 | 20 µl Composition 2e | 20 µl Composition 2e | 20 µl Composition 2e | 1 | 1,000 |
| 3 | 20 µl Composition 2e | 20 µl Composition 2e | 20 µl Composition 2e | 0.1 | 100 |
| 4 | 20 µl Composition 2e | 20 µl Composition 2e | 20 µl Composition 2e | 0.01 | 10 |
| 5 | 20 µl Composition 2e | 20 µl Composition 2e | 20 µl Composition 2e | 0.001 | 1 |
| 6 | 20 µl Composition 2e | 20 µl Composition 2e | 20 µl Composition 2e | 0 | 0 |
| | Astreonam | Benzyl penicillin | Cloxacillin | | |

TABLE 43-continued

Colour of media in each well after ~16 hours incubation at 37° C. (Table 39, plate configuration #3), for bacteria samples 5c T~16 h

|   | A | B | C |
|---|---|---|---|
| 4 | yellow | red | red |
| 5 | red | red | red |
| 6 | yellow | yellow | yellow |

TABLE 41

Colour of media in each well after ~16 hours incubation at 37° C. (Table 39, plate configuration #3), for bacteria samples 4c T~16 h

|   | A | B | C |
|---|---|---|---|
| 1 | yellow | red | red |
| 2 | yellow | red | yellow |
| 3 | yellow | red | yellow |
| 4 | yellow | yellow | yellow |
| 5 | yellow | yellow | yellow |
| 6 | yellow | yellow | yellow |

TABLE 44

Colour of media in each well after ~16 hours incubation at 37° C. (Table 39, plate configuration #3), for bacteria samples 5e T~16 h

|   | A | B | C |
|---|---|---|---|
| 1 | yellow | red | red |
| 2 | yellow | red | red |
| 3 | yellow | red | red |
| 4 | yellow | red | red |
| 5 | yellow | red | red |
| 6 | yellow | yellow | yellow |

TABLE 42

Colour of media in each well after ~16 hours incubation at 37° C. (Table 39, plate configuration #3), for bacteria samples 4e t~16 h

|   | A | B | C |
|---|---|---|---|
| 1 | red | Red | red |
| 2 | red | Red | red |
| 3 | yellow | Red | yellow |
| 4 | yellow | yellow | yellow |
| 5 | yellow | yellow | yellow |
| 6 | yellow | yellow | yellow |

TABLE 45

Colour of media in each well after ~16 hours incubation at 37° C. (Table 39, plate configuration #3), for bacteria samples 6d T~16 h

|   | A | B | C |
|---|---|---|---|
| 1 | yellow | red | red |
| 2 | yellow | red | red |
| 3 | yellow | red | red |
| 4 | yellow | red | red |
| 5 | yellow | red | red |
| 6 | yellow | yellow | yellow |

TABLE 46

80 µl Bacteria sample 5c + 20 µl composition 28a, b, c or d; incubation at 37° C.; Table shows colour of media in each well

|   | 0 h | 15 h |
|---|---|---|
| Composition 28a | Red | Yellow |
| Composition 28b | Red | Yellow |
| Composition 28c | Red | Yellow |
| Composition 28d | Red | Yellow |

TABLE 47

Plate configuration #4: well A1 to A8: 40 µl Composition 26 + 10 ul oxytetracylcine solution + 10 ul neomycin solution + 40 ul bacteria sample 5e; well B1 to B8: 45 µl Composition 26 + 10 ul oxytetracylcine solution + 15 ul neomycin solution + 40 ul bacteria sample 5e; well C1 to C8: 40 µl Composition 26 + 10 ul benzyl penicillin solution + 10 ul cloxacillin solution + 40 ul bacteria sample 5e; well D1 to D8: 46.7 µl Composition 26 + 10 ul benzyl penicillin solution + 3.3 ul cloxacillin solution + 40 ul bacteria sample 5e.

| well | A | B | C | D |
|---|---|---|---|---|
| 1 | 50 µg/ml oxytetracycline + 50 µg/ml neomycin | 50 µg/ml oxytetracycline + 25 µg/ml neomycin | 50 µg/ml benzyl penicillin + 50 µg/ml cloxacillin | 50 µg/ml benzyl penicillin + 16.7 µg/ml cloxacillin |
| 2 | 10 µg/ml oxytetracycline + 10 µg/ml neomycin | 10 µg/ml oxytetracycline + 5 µg/ml neomycin | 10 µg/ml benzyl penicillin + 10 µg/ml cloxacillin | 10 µg/ml benzyl penicillin + 3.3 µg/ml cloxacillin |
| 3 | 5 µg/ml oxytetracycline + 5 µg/ml neomycin | 5 µg/ml oxytetracycline + 2.5 µg/ml neomycin | 5 µg/ml benzyl penicillin + 5 µg/ml cloxacillin | 5 µg/ml benzyl penicillin + 1.7 µg/ml cloxacillin |
| 4 | 1 µg/ml oxytetracycline + 1 µg/ml neomycin | 1 µg/ml oxytetracycline + 0.5 µg/ml neomycin | 1 µg/ml benzyl penicillin + 1 µg/ml cloxacillin | 1 µg/ml benzyl penicillin + 0.33 µg/ml cloxacillin |
| 5 | 0.5 µg/ml oxytetracycline + 0.5 µg/ml neomycin | 0.5 µg/ml oxytetracycline + 0.25 µg/ml neomycin | 0.5 µg/ml benzyl penicillin + 0.5 µg/ml cloxacillin | 0.5 µg/ml benzyl penicillin + 0.17 µg/ml cloxacillin |
| 6 | 0.1 µg/ml oxytetracycline + 0.1 µg/ml neomycin | 0.1 µg/ml oxytetracycline + 0.05 µg/ml neomycin | 0.1 µg/ml benzyl penicillin + 0.1 µg/ml cloxacillin | 0.1 µg/ml benzyl penicillin + 0.033 µg/ml cloxacillin |
| 7 | 0.05 µg/ml oxytetracycline + 0.05 µg/ml neomycin | 0.05 µg/ml oxytetracycline + 0.025 µg/ml neomycin | 0.05 µg/ml benzyl penicillin + 0.05 µg/ml cloxacillin | 0.05 µg/ml benzyl penicillin + 0.017 µg/ml cloxacillin |
| 8 | 0.01 µg/ml oxytetracycline + 0.01 µg/ml neomycin Oxytetracylcine/Neomycin Ratio 1:1 (free form) | 0.01 µg/ml oxytetracycline + 0.005 µg/ml neomycin Oxytetracylcine/Neomycin Ratio 2:1 (free form) | 0.01 µg/ml benzyl penicillin + 0.01 µg/ml cloxacillin Benzyl Penicillin/Cloxacillin Ratio 1:1 (free form) | 0.01 µg/ml benzyl penicillin + 0.0033 µg/ml cloxacillin Benzyl Penicillin/Cloxacillin Ratio 3:1 (free form) |

TABLE 48

Colour of media in each well after 0 hours and 24 hours incubation at 35° C. (Table 47; plate configuration #4), for bacteria samples 5e

|   | A | B | C | D |
|---|---|---|---|---|
|   | T = 0 h | | | |
| 1 | red | red | red | red |
| 2 | red | red | red | red |
| 3 | red | red | red | red |
| 4 | red | red | red | red |
| 5 | red | red | red | red |
| 6 | red | red | red | red |
| 7 | red | red | red | red |
| 8 | red | red | red | red |
|   | T = 24 h | | | |
| 1 | red | red | red | red |
| 2 | red | red | red | red |
| 3 | red | red | red | red |
| 4 | red | red | red | red |
| 5 | red | red | red | red |
| 6 | red | red | red | red |
| 7 | red | red | red | red |
| 8 | red | red | red | yellow |

Example 7: Stabilizing Agents

The present invention is largely predicated on the surprising and unexpected discovery that bacteria may be cultured in growth media comprising growth inhibiting amounts of identification media and/or pH indicator in the presence of one or more stabilizing agents. Increasing the concentration of the identification media and/or pH indicator leads to increased sensitivity in the test since a phenotypic change in the reaction mix may be more readily and reliably observed.

Initial experiments according to the present invention were conducted in the presence of milk in respect of both gram positive and gram negative bacteria. Applicant observed that the identification media and/or pH indicator media could be increased to concentrations that would otherwise inhibit bacteria growth. For example, refer to the results in Tables 49-52 (*Staphylococcus aureus, Streptococcus uberis, Staphylococcus epidermidis* and *Escherichia coli* cultured in tryptic soy broth and phenol red (at a growth inhibiting concentration)) compared with Tables 53-56 (same experiment only in the presence of milk powder). The results demonstrate that milk powder had a stabilizing effect against the growth inhibiting effect of phenol red in the control experiment (i.e. Tables 49-52). Further, the results in Tables 5, 6, 79-86 (*Streptococcus uberis, Staphylococcus epidermidis* and *Staphylococcus aureus*) demonstrate the stabilizing effect of milk when the bacteria are cultured in concentrations of identification media that would otherwise be growth inhibiting.

The major components of milk (including milk powder) include casein proteins and carbohydrates. Applicant then tested growth inhibition effect of phenol red on the same bacteria in the presence of casein sodium (comprising α-casein, β-casein and κ-casein) and lactose. The data presented in Tables 53-64 provide preliminary proof-of-concept that the stabilizing effect is provided by the casein protein in the case of gram positive bacteria (i.e. *Staphylococcus aureus, Streptococcus uberis, Staphylococcus epidermidis*) whereas the stabilizing effect is provided by the carbohydrate in the case of gram negative bacteria (*Escherichia coli*).

Applicant then sought to investigate the stabilizing effect of different milk proteins and milk protein extracts (e.g. α-casein, β-casein (including one or more of A1, A2, A3, B, C, D, E and F variants), κ-casein, (β-lactoglobulin, whey protein, lactalbumin, lactoferrin and milk or milk powder), as well as different carbohydrates (e.g. dextrose, mannitol, lactose, trehalose and sucrose) on the observed growth inhibition effect. These data are presented in Tables 65-86, when read in conjunction with Table 90 (i.e. compositions). These data show that a stabilizing effect against growth inhibition in respect of gram negative bacteria is provided by dextrose, mannitol, lactose, trehalose and (to a lesser extent) sucrose, whereas a stabilizing effect against growth inhibition in respect of gram positive bacteria is provided by α-casein, β-casein (including one or more of A1, A2, A3, B, C, D, E and F variants), κ-casein, β-lactoglobulin, whey protein, lactalbumin, lactoferrin and milk or milk powder, depending on the bacteria being cultured.

Example 8: Urine Samples

The results presented in Tables 87-89 demonstrate the effectiveness of the methods of the present invention in a non-milk sample, namely urine spiked with *Escherichia coli* and *Streptococci uberis*. Tables 87, 88 show that gram negative bacteria (e.g. *E. coli*) with sugar present (i.e. lactose and/or trehalose) will grow in the presence of growth inhibiting amounts of phenol red in a quasi clinical sample. Further, Table 89 shows that gram positive bacteria (e.g. *Streptococci uberis*) with milk protein(s) present (i.e bovine whey, lactalbumin, casein sodium etc) will grow in the presence of growth inhibiting amounts of phenol red in a quasi clinical sample.

TABLE 49

Bacteria: *Staph aureus*
Media: tryptic soy broth + phenol red
Composition in wells: 80 ul media + 20 ul bacteria in TSB

| | cfu/ml | | | | | | | |
|---|---|---|---|---|---|---|---|---|
| Inoculum | $10^8$ | $10^7$ | $10^6$ | $10^5$ | $10^4$ | $10^3$ | $10^2$ | Control 0 (no bacteria) |
| | t = 0 h | | | | | | | |
| composition 2d | red | red | red | red | red | red | red | red |
| composition 2e | red | red | red | red | red | red | red | red |
| compsoition 2f | red | red | red | red | red | red | red | red |

TABLE 49-continued

Bacteria: *Staph aureus*
Media: tryptic soy broth + phenol red
Composition in wells: 80 ul media + 20 ul bacteria in TSB

| | cfu/ml | | | | | | | |
|---|---|---|---|---|---|---|---|---|
| Inoculum | 10^8 | 10^7 | 10^6 | 10^5 | 10^4 | 10^3 | 10^2 | Control 0 (no bacteria) |
| | | | | t = 12 h | | | | |
| composition 2d | yellow | red | red | red | red | red | red | red |
| composition 2e | red | red | red | red | red | red | red | red |
| compsoition 2f | red | red | red | red | red | red | red | red |
| | | | | t = 24 h | | | | |
| composition 2d | yellow | yellow | red | red | red | red | red | red |
| composition 2e | red | red | red | red | red | red | red | red |
| compsoition 2f | red | red | red | red | red | red | red | red |

TABLE 50

Bacteria: *Strep uberis*
Media: tryptic soy broth + phenol red
Composition in wells: 80 ul media + 20 ul bacteria in TSB

| | cfu/ml | | | | | | | |
|---|---|---|---|---|---|---|---|---|
| Inoculum | 10^8 | 10^7 | 10^6 | 10^5 | 10^4 | 10^3 | 10^2 | Control 0 (no bacteria) |
| | | | | t = 0 h | | | | |
| composition 2d | red | red | red | red | red | red | red | red |
| composition 2e | red | red | red | red | red | red | red | red |
| compsoition 2f | red | red | red | red | red | red | red | red |
| | | | | t = 12 h | | | | |
| composition 2d | red | red | red | red | red | red | red | red |
| composition 2e | red | red | red | red | red | red | red | red |
| compsoition 2f | red | red | red | red | red | red | red | red |
| | | | | t = 24 h | | | | |
| composition 2d | red | red | red | red | red | red | red | red |
| composition 2e | red | red | red | red | red | red | red | red |
| compsoition 2f | red | red | red | red | red | red | red | red |

TABLE 51

Bacteria: *Staph epidermidis* (Coagulase negative *Staph* - CNS)
Media: tryptic soy broth + phenol red
Composition in wells: 80 ul media + 20 ul bacteria in TSB

| | cfu/ml | | | | | | | |
|---|---|---|---|---|---|---|---|---|
| Inoculum | 10^8 | 10^7 | 10^6 | 10^5 | 10^4 | 10^3 | 10^2 | Control 0 (no bacteria) |
| | | | | t = 0 h | | | | |
| composition 2d | | red | red | red | red | red | red | red |
| composition 2e | | red | red | red | red | red | red | red |
| compsoition 2f | | red | red | red | red | red | red | red |
| | | | | t = 12 h | | | | |
| composition 2d | | yellow | red | red | red | red | red | red |
| composition 2e | | red | red | red | red | red | red | red |
| compsoition 2f | | red | red | red | red | red | red | red |

TABLE 51-continued

Bacteria: *Staph epidermidis* (Coagulase negative *Staph* - CNS)
Media: tryptic soy broth + phenol red
Composition in wells: 80 ul media + 20 ul bacteria in TSB

| | cfu/ml | | | | | | | |
|---|---|---|---|---|---|---|---|---|
| Inoculum | 10^8 | 10^7 | 10^6 | 10^5 | 10^4 | 10^3 | 10^2 | Control 0 (no bacteria) |
| | | | | t = 24 h | | | | |
| composition 2d | | yellow | red | red | red | red | red | red |
| composition 2e | | red | red | red | red | red | red | red |
| compsoition 2f | | red | red | red | red | red | red | red |

TABLE 52

Bacteria: *E-Coli*
Media: tryptic soy broth + phenol red
Composition in wells: 80 ul media + 20 ul bacteria in TSB

| | cfu/ml | | | | | | | |
|---|---|---|---|---|---|---|---|---|
| Inoculum | 10^8 | 10^7 | 10^6 | 10^5 | 10^4 | 10^3 | 10^2 | Control 0 (no bacteria) |
| | | | | t = 0 h | | | | |
| composition 2d | red | red | red | red | red | red | red | red |
| composition 2e | red | red | red | red | red | red | red | red |
| compsoition 2f | red | red | red | red | red | red | red | red |
| | | | | t = 12 h | | | | |
| composition 2d | orange | orange | orange | orange | orange | orange | orange | red |
| composition 2e | orange | orange | orange | orange | orange | orange | orange | red |
| compsoition 2f | orange/red | orange/red | orange/red | orange/ red | orange/red | orange/red | red | red |
| | | | | t = 24 h | | | | |
| composition 2d | orange/red | orange/red | orange/ red | orange/red | orange/ red | orange/red | orange/red | red |
| composition 2e | red | red | red | red | red | orange/red | orange/ red | red |
| compsoition 2f | red | red | red | red | red | red | red | red |

TABLE 53

Bacteria: *Staph aureus*
Media: tryptic soy broth + phenol red + 10% sterilised whole milk powder
Composition in wells: 80 ul media + 20 ul bacteria in TSB

| | cfu/ml | | | | | | | |
|---|---|---|---|---|---|---|---|---|
| Inoculum | 10^8 | 10^7 | 10^6 | 10^5 | 10^4 | 10^3 | 10^2 | Control 0 (no bacteria) |
| | | | | t = 0 h | | | | |
| composition 30a | red | red | red | red | red | red | red | red |
| composition 30b | red | red | red | red | red | red | red | red |
| composition 30c | red | red | red | red | red | red | red | red |
| | | | | t = 12 h | | | | |
| composition 30a | yellow | yellow | yellow | yellow | yellow | yellow | yellow | red |
| composition 30b | yellow | yellow | yellow | yellow | yellow | yellow | orange | red |
| composition 30c | yellow | yellow | yellow | yellow | yellow | yellow | red | red |
| | | | | t = 24 h | | | | |
| composition 30a | yellow | yellow | yellow | yellow | yellow | yellow | yellow | red |
| composition 30b | yellow | yellow | yellow | yellow | yellow | yellow | yellow | red |
| composition 30c | yellow | yellow | yellow | yellow | yellow | yellow | yellow | red |

TABLE 54

Bacteria: *Strep uberis*
Media: tryptic soy broth + phenol red + 10% sterilised whole milk powder
Composition in wells: 80 ul media + 20 ul bacteria in TSB

| Inoculum | cfu/ml | | | | | | | Control 0 (no bacteria) |
|---|---|---|---|---|---|---|---|---|
| | 10^8 | 10^7 | 10^6 | 10^5 | 10^4 | 10^3 | 10^2 | |
| t = 0 h | | | | | | | | |
| composition 30a | red | red | red | red | red | red | red | red |
| composition 30b | red | red | red | red | red | red | red | red |
| composition 30c | red | red | red | red | red | red | red | red |
| t = 12 h | | | | | | | | |
| composition 30a | yellow | yellow | yellow | yellow | yellow | red | red | red |
| composition 30b | yellow | yellow | yellow | yellow | yellow | red | red | red |
| composition 30c | yellow | yellow | yellow | yellow | red | red | red | red |
| t = 24 h | | | | | | | | |
| composition 30a | yellow | yellow | yellow | yellow | yellow | yellow | yellow | red |
| composition 30b | yellow | yellow | yellow | yellow | yellow | yellow | red | red |
| composition 30c | yellow | yellow | yellow | yellow | yellow | yellow | red | red |

TABLE 55

Bacteria: *Staph epidermidis* (Coagulase negative *Staph* - CNS)
Media: tryptic soy broth + phenol red + 10% sterilised whole milk powder
Composition in wells: 80 ul media + 20 ul bacteria in TSB

| Inoculum | cfu/ml | | | | | | | Control 0 (no bacteria) |
|---|---|---|---|---|---|---|---|---|
| | 10^8 | 10^7 | 10^6 | 10^5 | 10^4 | 10^3 | 10^2 | |
| t = 0 h | | | | | | | | |
| composition 30a | | red | red | red | red | red | red | red |
| composition 30b | | red | red | red | red | red | red | red |
| composition 30c | | red | red | red | red | red | red | red |
| t = 12 h | | | | | | | | |
| composition 30a | | yellow | yellow | yellow | red | red | red | red |
| composition 30b | | yellow | yellow | red | red | red | red | red |
| composition 30c | | yellow | yellow | red | red | red | red | red |
| t = 24 h | | | | | | | | |
| composition 30a | | yellow | yellow | yellow | yellow | yellow | red | red |
| composition 30b | | yellow | yellow | yellow | yellow | yellow | red | red |
| composition 30c | | yellow | yellow | yellow | yellow | yellow | red | red |

TABLE 56

Bacteria: *E-Coli*
Media: tryptic soy broth + phenol red + 10% sterilised whole milk powder
Composition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| t = 0 h | | | | | | | | |
| composition 30a | red | red | red | red | red | red | red | red |
| composition 30b | red | red | red | red | red | red | red | red |
| composition 30c | red | red | red | red | red | red | red | red |
| t = 12 h | | | | | | | | |
| composition 30a | yellow | yellow | yellow | yellow | yellow | yellow | yellow | red |
| composition 30b | yellow | yellow | yellow | yellow | yellow | yellow | yellow | red |
| composition 30c | yellow | yellow | yellow | yellow | yellow | yellow | yellow | red |

TABLE 56-continued

Bacteria: *E-Coli*
Media: tryptic soy broth + phenol red + 10% sterilised whole milk powder
Composition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | | t = 24 h | | | |
| composition 30a | yellow | yellow | yellow | yellow | yellow | yellow | yellow | red |
| composition 30b | yellow | yellow | yellow | yellow | yellow | yellow | yellow | red |
| composition 30c | yellow | yellow | yellow | yellow | yellow | yellow | yellow | red |

TABLE 57

Bacteria: *Staph aureus*
Media: tryptic soy broth + phenol red + 3% bovine casein sodium
Composition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | | t = 0 h | | | |
| composition 31a | red | red | red | red | red | red | red | red |
| composition 31b | red | red | red | red | red | red | red | red |
| composition 31c | red | red | red | red | red | red | red | red |
| | | | | | t = 12 h | | | |
| composition 31a | yellow | yellow | yellow | yellow | yellow | yellow | red | red |
| composition 31b | yellow | yellow | yellow | yellow | yellow | yellow | red | red |
| composition 31c | orange | orange | orange | orange | orange | orange | red | red |
| | | | | | t = 24 h | | | |
| composition 31a | yellow | yellow | yellow | yellow | yellow | yellow | yellow | red |
| composition 31b | yellow | yellow | yellow | yellow | yellow | yellow | yellow | red |
| composition 31c | orange | orange | orange | orange | orange | orange | orange | red |

TABLE 58

Bacteria: *Strep uberis*
Media: tryptic soy broth + phenol red + 3% bovine casein sodium
Composition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | | t = 0 h | | | |
| composition 31a | red | red | red | red | red | red | red | red |
| composition 31b | red | red | red | red | red | red | red | red |
| composition 31c | red | red | red | red | red | red | red | red |
| | | | | | t = 12 h | | | |
| composition 31a | yellow | yellow | yellow | yellow | red | red | red | red |
| composition 31b | yellow | yellow | yellow | red | red | red | red | red |
| composition 31c | yellow | yellow | yellow | red | red | red | red | red |
| | | | | | t = 24 h | | | |
| composition 31a | yellow | yellow | yellow | yellow | yellow | red | red | red |
| composition 31b | yellow | yellow | yellow | yellow | yellow | yellow | yellow | red |
| composition 31c | yellow | yellow | yellow | yellow | yellow | yellow | yellow | red |

TABLE 59

Bacteria: *Staph epidermidis* (Coagulase negative Staph - CNS)
Media: tryptic soy broth + phenol red + 3% bovine casein sodium
Composition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | t = 0 h | | | | |
| composition 31a | red | red | red | red | red | red | red | |
| composition 31b | red | red | red | red | red | red | red | |
| composition 31c | red | red | red | red | red | red | red | |
| | | | | t = 12 h | | | | |
| composition 31a | yellow | yellow | yellow | red | red | red | red | |
| composition 31b | yellow | yellow | red | red | red | red | red | |
| composition 31c | orange | orange | red | red | red | red | red | |
| | | | | t = 24 h | | | | |
| composition 31a | yellow | yellow | yellow | yellow | yellow | yellow | red | |
| composition 31b | yellow | yellow | yellow | yellow | yellow | yellow | red | |
| composition 31c | orange | orange | orange | orange | orange | orange | red | |

TABLE 60

Bacteria: *E-Coli*
Media: tryptic soy broth + phenol red + 3% bovine casein sodium
Composition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | | t = 0 h | | | |
| composition 31a | red | red | red | red | red | red | red | red |
| composition 31b | red | red | red | red | red | red | red | red |
| composition 31c | red | red | red | red | red | red | red | red |
| | | | | | t = 12 h | | | |
| composition 31a | yellow/orange | yellow/orange | yellow/orange | yellow/orange | yellow/orange | yellow/orange | yellow/orange | red |
| composition 31b | orange | orange | orange | orange | orange | orange | orange | red |
| composition 31c | red | red | red | red | red | red | red | red |
| | | | | | t = 24 h | | | |
| composition 31a | orange/red | orange/red | orange/red | orange/red | orange/red | orange/red | orange/red | red |
| composition 31b | red | red | red | red | red | red | red | red |
| composition 31c | red | red | red | red | red | red | red | red |

TABLE 61

Bacteria: *Staph aureus*
Media: tryptic soy broth + phenol red + 5% lactose
Composition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | t = 0 h | | | | |
| composition 32a | red | red | red | red | red | red | red | |
| composition 32b | red | red | red | red | red | red | red | |
| composition 33c | red | red | red | red | red | red | red | |
| | | | | t = 12 h | | | | |
| composition 32a | yellow | yellow | red | red | red | red | red | |
| composition 32b | red | red | red | red | red | red | red | |
| composition 33c | red | red | red | red | red | red | red | |

TABLE 61-continued

Bacteria: *Staph aureus*
Media: tryptic soy broth + phenol red + 5% lactose
Composition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| t = 24 h | | | | | | | | |
| composition 32a | yellow | yellow | yellow | red | red | red | red | red |
| composition 32b | yellow | red | red | red | red | red | red | red |
| composition 33c | red | red | red | red | red | red | red | red |

TABLE 62

Bacteria: *Strep uberis*
Media: tryptic soy broth + phenol red + 5% lactose
Composition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| t = 0 h | | | | | | | | |
| composition 32a | red | red | red | red | red | red | red | red |
| composition 32b | red | red | red | red | red | red | red | red |
| composition 33c | red | red | red | red | red | red | red | red |
| t = 12 h | | | | | | | | |
| composition 32a | red | red | red | red | red | red | red | red |
| composition 32b | red | red | red | red | red | red | red | red |
| composition 33c | red | red | red | red | red | red | red | red |
| t = 24 h | | | | | | | | |
| composition 32a | red | red | red | red | red | red | red | red |
| composition 32b | red | red | red | red | red | red | red | red |
| composition 33c | red | red | red | red | red | red | red | red |

TABLE 63

Bacteria: *Staph epidermidis* (Coagulase negative Staph - CNS)
Media: tryptic soy broth + phenol red + 5% lactose
Comopsition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| t = 0 h | | | | | | | | |
| composition 32a | | red | red | red | red | red | red | red |
| composition 32b | | red | red | red | red | red | red | red |
| composition 33c | | red | red | red | red | red | red | red |
| t = 12 h | | | | | | | | |
| composition 32a | | yellow | red | red | red | red | red | red |
| composition 32b | | yellow | red | red | red | red | red | red |
| composition 33c | | red | red | red | red | red | red | red |
| t = 24 h | | | | | | | | |
| composition 32a | | yellow | orange | red | red | red | red | red |
| composition 32b | | yellow | yellow | yellow | red | red | red | red |
| composition 33c | | red | red | red | red | red | red | red |

TABLE 64

Bacteria: *E-Coli*
Media: tryptic soy broth + phenol red + 5% lactose
Composition in wells: 80 ul media + 20 ul bacteria in TSB

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | | t = 0 h | | | |
| composition 32a | red | red | red | red | red | red | red | red |
| composition 32b | red | red | red | red | red | red | red | red |
| composition 33c | red | red | red | red | red | red | red | red |
| | | | | | t = 12 h | | | |
| composition 32a | yellow | yellow | yellow | yellow | yellow | yellow | yellow | red |
| composition 32b | yellow | yellow | yellow | yellow | yellow | yellow | yellow | red |
| composition 33c | yellow | yellow | yellow | yellow | yellow | yellow | yellow | red |
| | | | | | t = 24 h | | | |
| composition 32a | yellow | yellow | yellow | yellow | yellow | yellow | yellow | red |
| composition 32b | yellow | yellow | yellow | yellow | yellow | yellow | yellow | red |
| composition 33c | yellow | yellow | yellow | yellow | yellow | yellow | yellow | red |

TABLE 65

Bacteria: *Staph aureus*
80 ul composition 2d, 46 or 47 + 20 ul bacteria sample 2a, 2b, 2c, 2d, 2e, 2f or 2g

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | | t = 0 h | | | |
| composition 2d | red | red | red | red | red | red | red | red |
| composition 46 | red | red | red | red | red | red | red | red |
| composition 47 | red | red | red | red | red | red | red | red |
| | | | | | t = 12 h | | | |
| composition 2d | yellow | yellow | red | red | red | red | red | red |
| composition 46 | yellow | yellow | yellow | yellow | red | red | red | red |
| composition 47 | yellow | yellow | yellow | yellow | yellow | yellow | red | red |
| | | | | | t = 16 h | | | |
| composition 2d | yellow | yellow | orange | red | red | red | red | red |
| composition 46 | yellow | yellow | yellow | yellow | yellow | orange | red | red |
| composition 47 | yellow | yellow | yellow | yellow | yellow | yellow | yellow | red |
| | | | | | t = 24 h | | | |
| composition 2d | yellow | yellow | yellow | red | red | red | red | red |
| composition 46 | yellow | yellow | yellow | yellow | yellow | yellow | yellow | red |
| composition 47 | yellow | yellow | yellow | yellow | yellow | yellow | yellow | red |

TABLE 66

Bacteria: *E-Coli*
80 ul composition 2d, 31a or 32a + 20 ul bacteria sample 1a, 1b, 1c, 1d, 1e, 1f or 1g

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | | t = 0 h | | | |
| composition 32a | red | red | red | red | red | red | red | red |
| composition 31a | red | red | red | red | red | red | red | red |
| compsosition 2d | red | red | red | red | red | red | red | red |
| | | | | | t = 12 h | | | |
| composition 32a | yellow | yellow | yellow | yellow | yellow | yellow | yellow | red |
| composition 31a | orange | orange | orange | orange | orange | orange | orange | red |
| compsosition 2d | orange | orange | orange | orange | orange | orange | orange | red |

TABLE 66-continued

Bacteria: *E-Coli*
80 ul composition 2d, 31a or 32a + 20 ul bacteria sample 1a, 1b, 1c, 1d, 1e, 1f or 1g

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | | t = 24 h | | | |
| composition 32a | yellow | yellow | yellow | yellow | yellow | yellow | yellow | red |
| composition 31a | orange/red | orange/red | orange/red | orange/red | orange/red | orange/red | orange/red | red |
| compsosition 2d | orange/red | orange/red | orange/red | orange/red | orange/red | orange/red | orange/red | red |

TABLE 67

Bacteria: *E-Coli*
80 ul composition 43, 44 or 45 + 20 ul bacteria sample 1a, 1b, 1c, 1d, 1e, 1f or 1g

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | | t = 0 h | | | |
| composition 45 | red | red | red | red | red | red | red | red |
| composition 44 | red | red | red | red | red | red | red | red |
| composition 43 | red | red | red | red | red | red | red | red |
| | | | | | t = 12 h | | | |
| composition 45 | yellow | yellow | yellow | yellow | yellow | yellow | yellow | red |
| composition 44 | yellow | yellow | yellow | yellow | yellow | yellow | yellow | red |
| composition 43 | yellow | yellow | yellow | yellow | yellow | yellow | yellow | red |
| | | | | | t = 24 h | | | |
| composition 45 | yellow | yellow | yellow | yellow | yellow | yellow | yellow | red |
| composition 44 | orange | orange | orange | orange | orange | orange | orange | red |
| composition 43 | yellow | yellow | yellow | yellow | yellow | yellow | yellow | red |

TABLE 68

Bacteria: *E-Coli*
80 ul composition 40, 41 or 42 + 20 ul bacteria sample 1a, 1b, 1c, 1d, 1e, 1f or 1g

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | | t = 0 h | | | |
| composition 42 | red | red | red | red | red | red | red | red |
| composition 41 | red | red | red | red | red | red | red | red |
| composition 40 | red | red | red | red | red | red | red | red |
| | | | | | t = 12 h | | | |
| composition 42 | yellow | yellow | yellow | yellow | yellow | yellow | yellow | red |
| composition 41 | orange | orange | orange | orange | orange | orange | orange | red |
| composition 40 | Yellow | yellow | yellow | yellow | yellow | yellow | yellow | red |
| | | | | | t = 24 h | | | |
| composition 42 | Yellow | yellow | yellow | yellow | yellow | yellow | yellow | red |
| composition 41 | Orange | orange | orange | orange | orange | orange | orange | red |
| composition 40 | Yellow | yellow | yellow | yellow | yellow | yellow | yellow | red |

TABLE 69

Bacteria: *Staph aureus*
80 ul composition 48 + 20 ul bacteria sample 2a, 2b, 2c, 2d, 2e, 2f or 2g

| Inoculum cfu/ml | 10^8 | 10^7 | 10^6 | 10^5 | 10^4 | 10^3 | 10^2 | Control 0 (no bacteria) |
|---|---|---|---|---|---|---|---|---|
| | | | | t = 0 h | | | | |
| composition 48 | Red | red | red | red | red | red | red | red |
| | | | | t = 24 h | | | | |
| composition 48 | Yellow | yellow | red | red | red | red | red | red |

TABLE 70

Bacteria: *E-Coli*
80 ul composition 2e, 33, 34, 38, 39 + 20 ul bacteria sample 1b, 1d or 1f

| Inoculum cfu/ml | 10^7 | 10^5 | 10^3 | Control 0 (no bacteria) |
|---|---|---|---|---|
| | t = 0 h | | | |
| composition 2e | Red | red | red | red |
| composition 33 | Red | red | red | red |
| composition 34 | Red | red | red | red |
| composition 38 | Red | red | red | red |
| composition 39 | Red | red | red | red |
| | t = 12 h | | | |
| composition 2e | orange/red | orange/red | orange/red | red |
| composition 33 | orange/red | orange/red | orange/red | red |
| composition 34 | Yellow | yellow | yellow | red |
| composition 38 | orange/red | orange/red | orange/red | red |
| composition 39 | orange/red | orange/red | orange/red | red |
| | t = 24 h | | | |
| composition 2e | Red | red | red | red |
| composition 33 | Red | red | red | red |
| composition 34 | Yellow | yellow | yellow | red |
| composition 38 | Red | red | red | red |
| composition 39 | Red | red | red | red |

TABLE 71

Bacteria: *Staph aureus*
80 ul composition 2e, 33, 34, 35, 36, 37, 38, 39 + 20 ul bacteria sample 2b, 2d, or 2f

| Inoculum cfu/ml | 10^7 | 10^5 | 10^3 | Control 0 (no bacteria) |
|---|---|---|---|---|
| | t = 0 h | | | |
| composition 2e | Red | red | red | red |
| composition 33 | Red | red | red | red |
| composition 34 | Red | red | red | — |
| composition 35 | — | red | — | red |
| composition 36 | Red | red | red | red |
| composition 37 | Red | red | red | red |
| composition 38 | Red | red | red | red |
| composition 39 | Red | red | red | red |
| | t = 12 h | | | |
| composition 2e | Orange | red | red | red |
| composition 33 | Yellow | yellow | red | red |
| composition 34 | Yellow | yellow | orange | — |
| composition 35 | — | red | — | red |
| composition 36 | Yellow | yellow | red | red |
| composition 37 | Yellow | yellow | yellow | red |
| composition 38 | Orange | orange | red | red |
| composition 39 | Yellow | yellow | red | red |
| | t = 16 h | | | |
| composition 2e | Orange | red | red | red |
| composition 33 | Yellow | yellow | yellow | red |
| composition 34 | Yellow | yellow | yellow | — |
| composition 35 | — | red | — | red |
| composition 36 | Yellow | yellow | orange | red |
| composition 37 | Yellow | yellow | yellow | red |
| composition 38 | Orange | orange | orange | red |
| composition 39 | Yellow | yellow | yellow | red |
| | t = 24 h | | | |
| composition 2e | Yellow | red | red | red |
| composition 33 | Yellow | yellow | yellow | red |
| composition 34 | Yellow | yellow | yellow | — |
| composition 35 | — | red | — | red |
| composition 36 | Yellow | yellow | yellow | red |
| composition 37 | Yellow | yellow | yellow | red |
| composition 38 | orange/red | orange/red | orange/red | red |
| composition 39 | Yellow | yellow | yellow | red |

TABLE 72

Bacteria: *Strep uberis*
80 ul composition 2e, 33, 34, 35, 36, 37, 38, 39 + 20 ul bacteria sample 3b, 3d, or 3f

| Inoculum cfu/ml | 10^7 | 10^5 | 10^3 | Control 0 (no bacteria) |
|---|---|---|---|---|
| | t = 0 h | | | |
| composition 2e | Red | red | red | red |
| composition 33 | Red | red | red | red |
| composition 34 | Red | red | red | — |
| composition 35 | — | red | — | red |
| composition 36 | Red | red | red | red |
| composition 37 | Red | red | red | red |
| composition 38 | Red | red | red | red |
| composition 39 | Red | red | red | red |
| | t = 12 h | | | |
| composition 2e | Red | red | red | red |
| composition 33 | Yellow | yellow | yellow | red |
| composition 34 | Yellow | yellow | yellow | — |
| composition 35 | — | red | — | red |
| composition 36 | Yellow | yellow | yellow | red |
| composition 37 | Yellow | yellow | yellow | red |
| composition 38 | Yellow | yellow | yellow | red |
| composition 39 | Yellow | yellow | yellow | red |

TABLE 72-continued

Bacteria: *Strep uberis*
80 ul composition 2e, 33, 34, 35, 36, 37, 38, 39 + 20 ul bacteria sample 3b, 3d, or 3f

| Inoculum cfu/ml | 10^7 | 10^5 | 10^3 | Control 0 (no bacteria) |
|---|---|---|---|---|
| | | t = 16 h | | |
| composition 2e | Red | red | red | red |
| composition 33 | Yellow | yellow | yellow | red |
| composition 34 | Yellow | yellow | yellow | — |
| composition 35 | — | yellow | — | red |
| composition 36 | Yellow | yellow | yellow | red |
| composition 37 | Yellow | yellow | yellow | red |
| composition 38 | Yellow | yellow | yellow | red |
| composition 39 | Yellow | yellow | yellow | red |
| | | t = 24 h | | |
| composition 2e | Red | red | red | red |
| composition 33 | Yellow | yellow | yellow | red |
| composition 34 | Yellow | yellow | yellow | — |
| composition 35 | — | yellow | — | red |
| composition 36 | Yellow | yellow | yellow | red |
| composition 37 | Yellow | yellow | yellow | red |
| composition 38 | Yellow | yellow | yellow | red |
| composition 39 | Yellow | yellow | yellow | red |

TABLE 73

Bacteria: *E-Coli*
80 ul composition 40, 43 or 45 + 20 ul bacteria sample 1b, 1d or 1f

| Inoculum cfu/ml | 10^7 | 10^5 | 10^3 | Control 0 (no bacteria) |
|---|---|---|---|---|
| | | t = 0 h | | |
| composition 49 | Red | red | red | red |
| composition 50 | Red | red | red | red |
| composition 51 | Red | red | red | red |
| | | t = 12 h | | |
| composition 49 | Yellow | yellow | yellow | red |
| composition 50 | Yellow | yellow | yellow | red |
| composition 51 | Yellow | yellow | yellow | red |
| | | t = 24 h | | |
| composition 49 | Yellow | yellow | yellow | red |
| composition 50 | Yellow | yellow | yellow | red |
| composition 51 | Yellow | yellow | yellow | red |

TABLE 74

Bacteria: *Staph aureus*
80 ul composition 40, 43 or 45 + 20 ul bacteria sample 2b, 2d, or 2f

| Inoculum cfu/ml | 10^7 | 10^5 | 10^3 | Control 0 (no bacteria) |
|---|---|---|---|---|
| | | t = 0 h | | |
| composition 49 | Red | red | red | red |
| composition 50 | Red | red | red | red |
| composition 51 | Red | red | red | red |
| | | t = 24 h | | |
| composition 49 | Red | red | red | red |
| composition 50 | Red | red | red | red |
| composition 51 | Red | red | red | red |

TABLE 75

Bacteria: *Strep uberis*
80 ul composition 40, 43 or 45 + 20 ul bacteria sample 3b, 3d, or 3f

| Inoculum cfu/ml | 10^7 | 10^5 | 10^3 | Control 0 (no bacteria) |
|---|---|---|---|---|
| | | t = 0 h | | |
| composition 49 | Red | red | red | red |
| composition 50 | Red | red | red | red |
| composition 51 | Red | red | red | red |
| | | t = 24 h | | |
| composition 49 | Red | red | red | red |
| composition 50 | Red | red | red | red |
| composition 51 | Red | red | red | red |

TABLE 76

Bacteria: *E-Coli*
80 ul composition 2e, 53 or 54 + 20 ul bacteria sample 1b, 1d or 1f

| Inoculum | 10^7 | 10^5 | 10^3 |
|---|---|---|---|
| | | t = 0 h | |
| composition 2e | Red | red | red |
| composition 53 | Red | red | red |
| composition 54 | Red | red | red |
| | | t = 24 h | |
| composition 2e | Red | red | red |
| composition 53 | Red | red | red |
| composition 54 | Red | red | red |

TABLE 77

Bacteria: *Strep uberis*
80 ul composition 2e, 53 or 54 + 20 ul bacteria sample 3b, 3d or 3f

| Inoculum | 10^7 | 10^5 | 10^3 |
|---|---|---|---|
| | | t = 0 h | |
| composition 2e | Red | red | red |
| composition 53 | Red | red | red |
| composition 54 | Red | red | red |
| | | t = 24 h | |
| composition 2e | Red | red | red |
| composition 53 | Yellow | yellow | yellow |
| composition 54 | Yellow | yellow | yellow |

TABLE 78

Bacteria: *Staph aureus*
80 ul composition 2e, 53 or 54 + 20 ul bacteria sample 2b, 2d, or 2f

| Inoculum | 10^7 | 10^5 | 10^3 |
|---|---|---|---|
| | | t = 0 h | |
| composition 2e | Red | red | red |
| composition 53 | Red | red | red |
| composition 54 | Red | red | red |

TABLE 78-continued

Bacteria: *Staph aureus*
80 ul composition 2e, 53 or 54 + 20 ul bacteria sample 2b, 2d, or 2f

| | cfu/ml | | |
|---|---|---|---|
| Inoculum | 10^7 | 10^5 | 10^3 |
| | | t = 24 h | |
| composition 2e | Red | red | red |
| composition 53 | Yellow | yellow | yellow |
| composition 54 | Yellow | yellow | yellow |

TABLE 79

Bacteria: *Staph epidermidis*
80 ul composition 55 + 20 ul bacteria sample 12a or 12b

| | cfu/ml | |
|---|---|---|
| Inoculum | 10^7 | 10^5 |
| composition 55 | t = 0 h<br>Red | t = 0 h<br>red |
| composition 55 | t = 19 h<br>Red | t = 19 h<br>red |

TABLE 80

Bacteria: *Staph epidermidis*
80 ul composition 55 + 20 ul bacteria sample 7b or 7d

| | cfu/ml | |
|---|---|---|
| Inoculum | 10^7 | 10^5 |
| composition 55 | t = 0 h<br>Red | t = 0 h<br>red |
| composition 55 | t = 19 h<br>Yellow | t = 19 h<br>yellow |

TABLE 81

Bacteria: *Staph aureus*
80 ul composition 55 + 20 ul bacteria sample 2d, or 2f

| | cfu/ml | |
|---|---|---|
| Inoculum | 10^5 | 10^3 |
| composition 55 | t = 0 h<br>Red | t = 0 h<br>red |
| composition 55 | t = 19 h<br>Red | t = 19 h<br>red |

TABLE 82

Bacteria: *Staph aureus*
80 ul composition 55 + 20 ul bacteria sample 5d, or 5f

| | cfu/ml | |
|---|---|---|
| Inoculum | 10^5 | 10^3 |
| composition 55 | t = 0 h<br>Red | t = 0 h<br>red |
| composition 55 | t = 19 h<br>Yellow | t = 19 h<br>yellow |

TABLE 83

Bacteria: *Staph aureus*
80 ul composition 57 + 20 ul bacteria sample 2d, or 2f

| | cfu/ml | |
|---|---|---|
| Inoculum | 10^5 | 10^3 |
| composition 57 | t = 0 h<br>light yellow | t = 0 h<br>light yellow |
| composition 57 | t = 19 h<br>light yellow | t = 19 h<br>light yellow |

TABLE 84

Bacteria: *Staph aureus*
80 ul composition 57 + 20 ul bacteria sample 5d, or 5f

| | cfu/ml | |
|---|---|---|
| Inoculum | 10^5 | 10^3 |
| composition 57 | t = 0 h<br>White | t = 0 h<br>white |
| composition 57 | t = 19 h<br>Black | t = 19 h<br>black |

TABLE 85

Bacteria: *Staph aureus*
80 ul freeze dried composition 59 +
80 ul bacteria sample 2c, 2d, 2e, 2f or 2g

| | cfu/ml | | | | |
|---|---|---|---|---|---|
| Inoculum | 10^6 | 10^5 | 10^4 | 10^3 | 10^2 |
| | t = 0 h | | | | |
| composition 59 | light yellow | light yellow | light yellow | light yellow | light yellow |
| | t = 16 h | | | | |
| composition 59 | light brown | light brown | light yellow | light yellow | light yellow |

TABLE 86

Bacteria: *Staph aureus*
80 ul freeze dried composition 59 +
80 ul bacteria sample 5c, 5d, 5e, 5f or 5g

| | cfu/ml | | | | |
|---|---|---|---|---|---|
| Inoculum | 10^6 | 10^5 | 10^4 | 10^3 | 10^2 |
| | t = 0 h | | | | |
| composition 59 | White | white | white | white | white |
| | t = 16 h | | | | |
| composition 59 | Black | black | black | black | black |

TABLE 87

Bacteria: *E-Coli*
80 ul composition 2e, 33 or 49 + 20 ul bacteria sample 10a, 10b or 10c

| | cfu/ml | | | |
|---|---|---|---|---|
| Inoculum | 10^7 | 10^5 | 10^3 | Control 0 (no bacteria) |
| t = 0 h | | | | |
| composition 2e | Red | red | red | red |
| composition 39 | Red | red | red | red |
| composition 52 | Red | red | red | red |
| t = 24 h | | | | |
| composition 2e | Red | red | red | red |
| composition 39 | Red | red | red | red |
| composition 52 | Yellow | yellow | yellow | red |

TABLE 88

Bacteria: *E-Coli*
80 ul composition 2e, 36 or 37 + 20 ul bacteria sample 10a, 10b, 10c

| | cfu/ml | | | |
|---|---|---|---|---|
| Inoculum | 10^7 | 10^5 | 10^3 | Control 0 (no bacteria) |
| t = 0 h | | | | |
| composition 2e | red | red | red | red |
| composition 36 | red | red | red | red |
| composition 37 | red | red | red | red |
| t = 24 h | | | | |
| composition 2e | red | red | red | red |
| composition 36 | red | red | red | red |
| composition 37 | red | red | red | red |

TABLE 89

Bacteria: *Strep uberis*
80 ul composition 2e, 36, 40, 49, 33 or 52 + 20 ul bacteria sample 11a, 11b or 11c

| | cfu/ml | | | |
|---|---|---|---|---|
| Inoculum | 10^7 | 10^5 | 10^3 | Control 0 (no bacteria) |
| t = 0 h | | | | |
| composition 2e | red | red | red | red |
| composition 39 | red | red | red | red |
| composition 52 | red | red | red | red |
| composition 49 | red | red | red | red |
| composition 36 | red | red | red | red |
| composition 37 | red | red | red | red |
| t = 24 h | | | | |
| composition 2e | red | red | red | red |
| composition 39 | yellow | yellow | yellow | red |
| composition 52 | yellow | yellow | yellow | red |
| composition 49 | red | red | red | red |
| composition 36 | yellow | yellow | yellow | red |
| composition 37 | yellow | yellow | yellow | red |

TABLE 90

| | Compositions | | | | | | | |
|---|---|---|---|---|---|---|---|---|
| Composition | Tryptic Soy Broth | Phenol red | whole milk powder | casein sodium (Bovine milk) | α Casein | β Casein | κ casein | β-lactoglobulin | Bovine Whey |
| composition 2f | 99.90% | 0.10% | | | | | | | |
| composition 30a | 89.975% | 0.025% | 10% | | | | | | |
| composition 30b | 89.95% | 0.05% | 10% | | | | | | |
| composition 30c | 89.90% | 0.10% | 10% | | | | | | |
| composition 31a | 96.975% | 0.025% | | 3% | | | | | |
| composition 31b | 96.95% | 0.05% | | 3% | | | | | |
| composition 31c | 96.90% | 0.10% | | 3% | | | | | |
| composition 32a | 94.975% | 0.025% | | | | | | | |
| composition 32b | 94.95% | 0.05% | | | | | | | |
| composition 32c | 94.90% | 0.10% | | | | | | | |
| composition 33 | 98.95% | 0.05% | | 1.0% | | | | | |
| composition 34 | 91.95% | 0.05% | | 5.0% | | | | | |
| composition 35 | 98.95% | 0.05% | | | | | | | |
| composition 36 | 98.95% | 0.05% | | | | | | | 1.0% |
| composition 37 | 98.95% | 0.05% | | | | | | | |
| composition 38 | 98.95% | 0.05% | | | 1.0% | | | | |
| composition 39 | 98.95% | 0.05% | | | | 1.0% | | | |
| composition 40 | 98.95% | 0.05% | | | | | | | |
| composition 41 | 98.975% | 0.025% | | | | | | | |
| composition 42 | 98.975% | 0.025% | | | | | | | |
| composition 43 | 98.975% | 0.025% | | | | | | | |
| composition 44 | 99.875% | 0.025% | | | | | | | |
| composition 45 | 98.975% | 0.025% | | | | | | | |
| composition 46 | 99.875% | 0.025% | | 0.1% | | | | | |
| composition 47 | 99.575% | 0.025% | | 0.4% | | | | | |
| composition 48 | 94.975% | 0.025% | | | | | | | |

TABLE 90-continued

| Compositions | | | | | |
|---|---|---|---|---|---|
| composition 49 | 98.95% | 0.05% | | | |
| composition 50 | 98.95% | 0.05% | | | |
| composition 51 | 98.95% | 0.05% | | | |
| composition 52 | 97.95% | 0.05% | 1.0% | | |
| composition 53 | 98.95% | 0.05% | | 1.0% | |
| composition 54 | 98.95% | 0.05% | | | 1.0% |

| Composition | Lactalbumin | Lactoferrin | Lactose | Dextrose | Mannitol | Sucrose | Trehalose | Comment |
|---|---|---|---|---|---|---|---|---|
| composition 2f | | | | | | | | |
| composition 30a | | | | | | | | |
| composition 30b | | | | | | | | |
| composition 30c | | | | | | | | |
| composition 31a | | | | | | | | |
| composition 31b | | | | | | | | |
| composition 31c | | | | | | | | |
| composition 32a | | | 5.0% | | | | | |
| composition 32b | | | 5.0% | | | | | |
| composition 32c | | | 5.0% | | | | | |
| composition 33 | | | | | | | | |
| composition 34 | | | 3.0% | | | | | |
| composition 35 | | 1.0% | | | | | | |
| composition 36 | | | | | | | | Centrifuged, sediment dicarded, supernatant used only |
| composition 37 | 1.0% | | | | | | | Centrifuged, sediment dicarded, supernatant used only |
| composition 38 | | | | | | | | |
| composition 39 | | | | | | | | |
| composition 40 | 1.0% | | | | | | | Centrifuged, sediment dicarded, supernatant used only |
| composition 41 | | | | | | 1.0% | | |
| composition 42 | | | | | 1.0% | | | |
| composition 43 | | | | | | | 1.0% | |
| composition 44 | | | 0.1% | | | | | |
| composition 45 | | | 1.0% | | | | | |
| composition 46 | | | | | | | | |
| composition 47 | | | | | | | | |
| composition 48 | | | | 5.0% | | | | |
| composition 49 | | | 1.0% | | | | | |
| composition 50 | | | | 1.0% | | | | |
| composition 51 | | | | | | | 1.0% | |
| composition 52 | | | 1.0% | | | | 1.0% | |
| composition 53 | | | | | | | 1.0% | |
| composition 54 | | | | | | | 1.0% | |

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification. The specific assays and methods described herein are representative of preferred embodiments and are exemplary and not intended as limitations on the scope of the invention. Other aspects and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed as essential. Thus, for example, in each instance described or used herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The assays and methods illustratively described herein suitably may be practiced in differing orders of steps, and that they are not necessarily restricted to the orders of steps indicated herein or in the claims. Further, as used or described herein and in the appended claims, the singular forms "a," "an," and "the" include plural reference unless the context clearly dictates otherwise. Under no circumstances may the patent be interpreted to be limited to the specific examples or embodiments or methods specifically disclosed herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts disclosed herein may be resorted to by those skilled in the art, and that such modifications and variations are considered to be within the scope of this invention as described herein, and as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method for performing an antimicrobial susceptibility test on a biological sample obtained from a human or non-human animal, wherein the human or non-human animal may be infected by, or at risk of infection by, one or more infection causing bacteria, the method comprising,
   (i) providing a reaction mix comprising a biological sample obtained from a human or non-human animal and susceptibility media comprising growth media, an antimicrobial agent, a colour based pH indicator and a stabilizing agent comprising a milk derived protein or milk derived protein extract; and
   (ii) determining the susceptibility of the one or more bacteria in the sample to the antimicrobial agent by observing a colour change when the sample is mixed with the susceptibility media,
   wherein, the pH indicator is present in the reaction mix in an amount greater than or equal to 0.0035% and sufficient to inhibit growth of the one or more infection causing bacteria if not for the presence of the stabilizing agent.

2. The method according to claim 1, wherein the milk derived protein or milk derived protein extract comprises one or more selected from the group consisting of α-casein, β-casein, casein sodium, κ-casein, β-lactoglobulin, whey protein, lactalbumin, lactoferrin, milk or milk powder, and combinations thereof.

3. The method according to claim 1, wherein when the bacteria is a gram negative bacteria, the stabilizing agent comprises a carbohydrate.

4. The method according to claim 3, wherein the carbohydrate is selected from the group consisting of dextrose, mannitol, lactose, trehalose and sucrose.

5. The method according to claim 1, wherein the biological sample is selected from the group consisting of milk, fluid sample from the uterus, whole blood sample, plasma, serum, ovarian follicular fluid sample, seminal fluid sample, cerebrospinal fluid, saliva, sputum, urine, pleural effusions, interstitial fluid, synovial fluid, lymph and tears.

6. The method according to claim 1, wherein when the biological sample is milk there is no requirement for the reaction mix to comprise a stabilizing agent.

7. The method according to claim 1, wherein the colour based pH indicator is selected from the group consisting of phenol red, bromocresol purple and bromothymol blue.

8. The method according to claim 1, wherein the colour based pH indicator is phenol red.

9. The method according to claim 8, wherein the phenol red is present at between 0.0035 and 0.30% of the reaction mix.

10. The method according to claim 1, wherein the susceptibility media comprises one or more growth media selected from the group consisting of Tryptic Soy Broth and Mueller Hinton Broth.

11. The method according to claim 1, wherein the infection is mastitis or metritis, and wherein the bacteria causing mastitis or metritis is selected from one or more of the genus *Streptococcus*, the genus *Staphylococcus* or gram negative bacteria.

* * * * *